US009366673B2

(12) United States Patent
McCluskey et al.

(10) Patent No.: US 9,366,673 B2
(45) Date of Patent: Jun. 14, 2016

(54) PORPHYROMONAS GINGIVALIS POLYPEPTIDES

(75) Inventors: Jacqueline McCluskey, Boston, MA (US); Robert Charlebois, Toronto (CA); Laurence Quemeneur, Marcy l'Etoile (FR); Jeremy Yethon, Boston, MA (US); Michael Leach, Toronto (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 765 days.

(21) Appl. No.: 13/388,042

(22) PCT Filed: Jul. 30, 2010

(86) PCT No.: PCT/CA2010/001177
§ 371 (c)(1),
(2), (4) Date: Mar. 7, 2012

(87) PCT Pub. No.: WO2011/014947
PCT Pub. Date: Feb. 10, 2011

(65) Prior Publication Data
US 2012/0156211 A1      Jun. 21, 2012

Related U.S. Application Data

(60) Provisional application No. 61/230,717, filed on Aug. 2, 2009.

(51) Int. Cl.
| | |
|---|---|
| *A61K 39/02* | (2006.01) |
| *A61P 31/04* | (2006.01) |
| *C07K 14/195* | (2006.01) |
| *C07K 16/12* | (2006.01) |
| *A61K 39/395* | (2006.01) |
| *A61P 37/04* | (2006.01) |
| *G01N 33/569* | (2006.01) |
| *A61K 39/00* | (2006.01) |

(52) U.S. Cl.
CPC ...... *G01N 33/56955* (2013.01); *A61K 39/0216* (2013.01); *C07K 16/1257* (2013.01); *A61K 39/00* (2013.01); *A61K 2039/55505* (2013.01); *A61K 2039/55566* (2013.01); *G01N 2333/21* (2013.01)

(58) Field of Classification Search
None
See application file for complete search history.

(56) References Cited

U.S. PATENT DOCUMENTS

2010/0092471 A1   4/2010 Daspher et al.

OTHER PUBLICATIONS

Naito et al. (DNA Research, 2008, vol. 15, pp. 215-225).*
Nelson et al. (Journal of Bacteriology, 2003, vol. 185 No. 18, pp. 5591-5601).*
Colman (Res. Immunology, Jan. 1994, vol. 145, pp. 33-36).*
Greenspan et al. (Nature Biotechnology 7: 936-937, 1999).*
Bowie et al (Science, 1990, 257:1306-1310).*
Booth, et al., Passive immunization with monoclonal antibodies against Porphyromonas gingivalis in patients with periodontitis. Infect. Immun. 64(2): 422-427 (1996).
Frazer, et al. Vaccination with recombinant adhesins from the RgpA-Kgp proteinase-adhesin complex protects against Porphyromonas gingivalis infection. Vaccine 24 (42-43): 6542-6554 (2006).
Holt, et al. Virulence factors of P gingivalis. Periodontology 2000. 20: 168-238 (2004).
Naito, et al. Determination of the Genome Sequence of Porphyromonas gingivalis Strain ATCC 33277 and Genomic Comparison with Strain W83 Revealed Extensive Genome Rearrangements in P. gingivalis DNA Res. 15(4): 215-225 (2008).
Nelson, et al, complete genome sequence of the oral pathogenic bacterium P. gingivalis strain W83. J. Bacteriol. 185(18): 5591-5601 (2003).
O'Brien-Simpson, et al. Serum immunoglobulin G (IgG) and IgG subclass responses to the RgpA-Kgp proteinase-ashesin complex of Porphyromonas gingivalis in adult periodontitis, Inf. Immun. 68(5): 2704-2712 (2000).
O'Brien-Simpson, et al. RgpA-Kgp peptide-based immunogens provide protection against Porphyromonas gingivalis challenge in a murine lesion model. Infection & Immunity 68(7): 4055-4063 (2000).
O'Brien-Simpson, et al. Role of RgpA, RgpB and Kgp proteinases in virulence of Porphyromonas gingivalis W50 in a murine lesion model. Inf. Immun. 69(12): 7527-7534 (2001).
O'Brien-Simpson, et al. An immune response directed to proteinase and adhesin functional epiptopes protects against Porphyromonas gingivalis-induced periotontal bone loss. J. Immunol. 175(6): 3980-3989 (2005).
O'Brien-Simpson, et al., Porphyromonas gingivalis RgpA-Kgp proteinase-adhesin complexes penetrate gingival tissue and induce pro-inflammatory cytokines or apoptosis in a concentration-dependant manner. Infect Immun. 77(3): 1246-1261 (2008).
O'Brien-Simpson, et al. Antigens of bacteria associated with periodontitis Periodontology 2000, 35: 101-134 (2004).
Tam, et al. Characterization of T Cell Responses to the RgpA-Kgp Proteinase-Adhesin Complexedens of Porphyromonas gingivalis in BALB/c Mice. J. Immunol. 181(6): 4150-4158 (2008).
Yokoyama, et al. Effects of egg yolk antibody against P. gingivalis gingipains in periodontitis patients. J Oral Sci. 49(3): 201-206 (2007).

* cited by examiner

*Primary Examiner* — Robert A Zeman
(74) *Attorney, Agent, or Firm* — Patrick J. Halloran

(57) ABSTRACT

Provided herein are compositions and methods for eliciting an immune response against *Porphyromonas gingivalis*. The compositions and methods relate to *P. gingivalis* polypeptides and fragments and variants thereof and the corresponding polynucleotides which are useful in the diagnosis, prevention and therapy of *P. gingivalis* infections (e.g. periodontitis). Antibodies against the polypeptides and compositions and methods including these antibodies are also disclosed. The disclosure also describes methods for the detection, prevention and treatment of *P. gingivalis* infection (e.g. periodontitis).

15 Claims, 6 Drawing Sheets

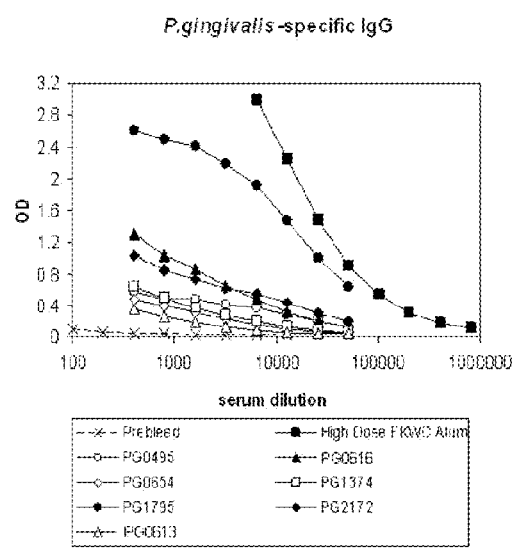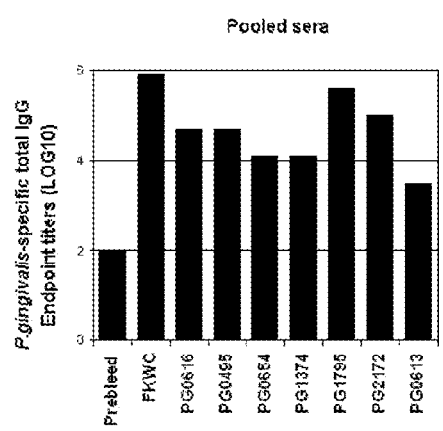
Figure 1(a)
Figure 1(b)

US 9,366,673 B2

PORPHYROMONAS GINGIVALIS POLYPEPTIDES

CROSS-REFERENCE TO RELATED APPLICATION

This application claims the benefit of U.S. Provisional Application No. 61/230,717, filed on Aug. 2, 2009, which is hereby incorporated herein by reference in its entirety.

SEQUENCE LISTING

The instant application contains a Sequence Listing which has been submitted as an ASCII text file in the instant application via EFS-Web on May 16, 2013 and is hereby incorporated by reference in its entirety. The ASCII copy was created on May 16, 2013, is named APL0901PCTUS-SEQLIST.txt and is 189 KB in size.

FIELD OF THE INVENTION

The present invention relates to the field of immunology and in particular to P. gingivalis antigens and their use in immunization and therapy.

BACKGROUND

Periodontitis (or periodontal disease) is an inflammatory disease of the supporting tissues of the teeth. Disease progression is characterized by formation of a periodontal pocket (harbouring bacterial plaque), progressive destruction of supporting connective tissue and loss of alveolar bone, leading to progressive loosening and eventual loss of teeth. Periodontal disease is associated with specific bacteria in subgingival dental plaque. Porphyromonas gingivalis is considered one of the most etiologically important pathogens associated with periodontitis and its progression. This black-pigmented, asaccharolytic, Gram-negative anaerobe, relies on the metabolism of specific amino acids for energy. P. gingivalis has an absolute requirement for iron, preferentially in the form of heme or its Fe(III) oxidation product hemin and when grown under conditions of excess hemin is highly virulent in experimental animals.

A number of virulence factors have been implicated in the pathogenicity of P. gingivalis including the capsule, adhesins, cytotoxins and extracellular hydrolytic enzymes. A major virulence factor and vaccine candidate of the P. gingivalis are the extracellular cysteine proteinases or gingipains (RgpA, RgpB and Kgp). These have been extensively studied (1-8). The gingipain complex alone has been shown to protect against periodontal bone loss in prophylactic animal models and antibodies specific to this complex have demonstrated protective efficacy in human studies (9,10). Despite this, virulence and the disease-causing capacity of P. gingivalis may likely be multifactoral, involving a number of determinants (11).

The genome of P. gingivalis strains W83 and ATCC 33277 have each been sequenced (12,13), but these references do not provide any teaching on which P. gingivalis antigens are immunogenic and otherwise useful.

Consequently, there remains a need for effective treatments of P. gingivalis infections.

SUMMARY OF THE INVENTION

The present invention provides compositions and methods for eliciting an immune response against P. gingivalis. Also provided are methods for the prevention or treatment of a P. gingivalis infection (e.g., periodontitis). In one example, the composition comprises at least one polypeptide selected from the group consisting of PG0495, PG0654, PG1374, PG1795, PG2172, PG0613, PG1326, PG1798, PG0186 and PG0616. Antibodies that bind specifically to these polypeptides and compositions comprising, and methods of using, such antibodies are also provided.

Compositions, such as pharmaceutical compositions (e.g., vaccine compositions) including one or more polypeptides are provided. Optionally, the compositions can include an adjuvant.

The invention provides several advantages. For example, administration of the compositions of the present invention to a subject elicits an immune response against infections by P. gingivalis.

Other features and advantages of the invention will be apparent from the following Detailed Description, the Drawings and the Claims.

BRIEF DESCRIPTION OF THE FIGURES

The present invention will be further understood from the following description with reference to the drawings, in which:

FIG. 1 Consisting of panels A and B, illustrates P. gingivalis specific IgG responses. FIG. 1a depicts the serum anti-protein IgG antibody responses of Example 3 and FIG. 1B depicts the serum total IgG antibody responses of Example 3

DETAILED DESCRIPTION OF THE INVENTION

Figure 2:
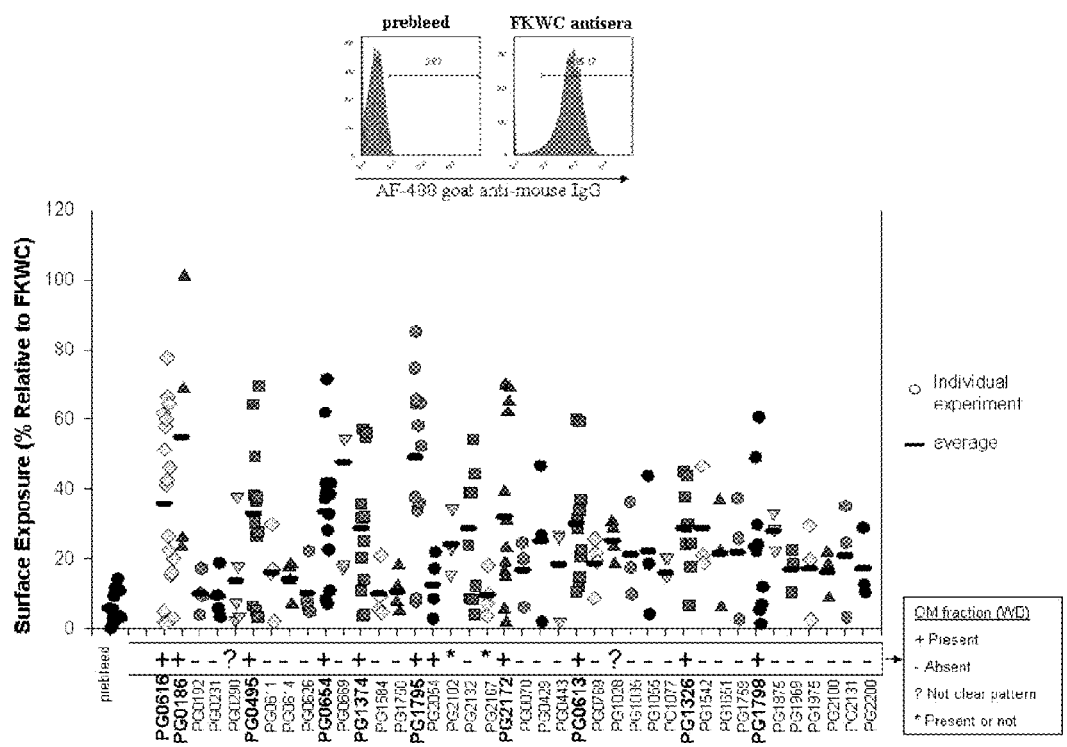
FIG. 2 Depicts accessibility of proteins on cell surface of P. gingivalis (W50 strain), at stationary phase, as measured by a flow cytometry based assay. Each dot on Y-axis represents result obtained. Average of results represented by a horizontal dash (-). Name of each protein identified on X-axis. Presence of proteins in outer membrane fractions of P. gingivalis was also assessed (as discussed in Example 4) and results provided on X-axis (e.g., + indicates protein was detected in OM fraction; - indicates protein was absent from OM fraction; * indicates that the protein was detected in the OM in some experiments but not in others.

The present invention provides P. gingivalis polypeptides and their corresponding encoding nucleic acids which elicit an immune response when administered to a subject. Provided for example, are polypeptides of PG0495, PG0654, PG1374, PG1795, PG2172, PG0613, PG1326, PG1798, PG0186 and PG0616, nucleic acid sequences that encode these polypeptides and antibodies that bind specifically to these polypeptides. Immunogenic compositions comprising at least one *P. gingivalis* polypeptide and methods for preventing, treating and reducing the risk of a *P. gingivalis* infection, and for eliciting or inducing an immune response in a subject using these compositions are also provided as are methods for making the compositions. The polypeptide and nucleic acid sequences of the present invention include, but are not limited to, the specific nucleic acid and amino acid sequences set forth in the Sequence Listing that forms part of the present specification. These polypeptides, compositions and methods are described further below.

DEFINITIONS

The term "antigen" as used herein refers to a substance that is capable of stimulating immune responses. The immune responses stimulated by antigens may be one or both of humoral or cellular, and generally are specific for the antigen. An antigen is capable of initiating and mediating the formation of a corresponding immune body (antibody) when introduced into a subject. An antigen may possess multiple antigenic determinants such that the exposure of the subject to an antigen may produce a plurality of corresponding antibodies with differing specificities. Antigens may include, but are not limited to proteins, peptides, polypeptides, nucleic acids and fragments, variants and combinations thereof.

The terms peptides, proteins and polypeptides are used interchangeably herein.

An "isolated" polypeptide is one that has been removed from its natural environment. For instance, an isolated polypeptide is a polypeptide that has been removed from the cytoplasm or from the membrane of a cell, and many of the polypeptides, nucleic acids, and other cellular material of its natural environment are no longer present. An "isolatable" polypeptide is a polypeptide that could be isolated from a particular source. A "purified" polypeptide is one that is at least 60% free, preferably at least 75% free, and most preferably at least 90% free from other components with which they are naturally associated. Polypeptides that are produced outside the organism in which they naturally occur, e.g. through chemical or recombinant means, are considered to be isolated and purified by definition, since they were never present in a natural environment.

The term "surface accessible protein" refers to all surface exposed proteins, including for example, inner and outer membrane proteins, proteins adhering to the cell wall and secreted proteins.

As used herein, a "fragment" of a polypeptide preferably has at least about 40 residues, or 60 residues, and preferably at least about 100 residues in length. Fragments of *P. gingivalis* polypeptides can be generated by methods known to those skilled in the art.

The term "antibody" or "antibodies" refers to monoclonal and polyclonal antibodies and includes whole or fragmented antibodies in unpurified or partially purified form (i.e., hybridoma supernatant, ascites, polyclonal antisera) or in purified form. In some embodiments, antigen-binding portions of antibodies include Fab, Fab', F(ab')2, Fd, Fv, dAb and complementary determining region (CDR) variants, single chain antibodies (scFv), chimeric antibodies such as humanized antibodies, diabodies and polypeptides that contain at least a portion of an antibody that is sufficient to confer specific antigen binding to the polypeptide.

A "purified" antibody is one that is separated from at least about 50% of the proteins with which it is initially found (i.e., as part of a hybridoma supernatant or ascites preparation).

As used in the specification and the appended claims, the singular forms "a", "an", and "the" include plural referents unless the context clearly dictates otherwise. Thus, for example, reference to a fragment may include mixtures of fragments and reference to a pharmaceutical carrier or adjuvant may include mixtures of two or more such carriers or adjuvants.

As used herein, a subject or a host is meant to be an individual. The subject can include domesticated animals, such as cats and dogs, livestock (e.g., cattle, horses, pigs, sheep, and goats), and laboratory animals (e.g., mice, rabbits, rats, guinea pigs). In one aspect, the subject is a mammal such as a primate or a human.

Optional or optionally means that the subsequently described event or circumstance can or cannot occur, and that the description includes instances where the event or circumstance occurs and instances where it does not. For example, the phrase, "optionally the composition can comprise a combination" means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint.

When the terms prevent, preventing, and prevention are used herein in connection with a given prophylactic treatment for a given condition (e.g., preventing infection by *P. gingivalis*), it is meant to convey that the treated subject either does not develop a clinically observable level of the condition at all, or develops it more slowly and/or to a lesser degree than he/she would have absent the treatment. These terms are not limited solely to a situation in which the subject experiences no aspect of the condition whatsoever. For example, a treatment will be said to have prevented the condition if it is given during exposure of a patient to a stimulus that would have been expected to produce a given manifestation of the condition, and results in the subject's experiencing fewer and/or milder symptoms of the condition than otherwise expected. A treatment can "prevent" infection by resulting in the subject's displaying only mild overt symptoms of the infection; it does not imply that there must have been no penetration of any cell by the infecting microorganism.

Similarly, reduce, reducing, and reduction as used herein in connection with the risk of infection with a given treatment (e.g., reducing the risk of a *P. gingivalis* infection) refers to a subject developing an infection more slowly or to a lesser degree as compared to a control or basal level of developing an infection in the absence of a treatment. A reduction in the risk of infection may result in the subject displaying only mild overt symptoms of the infection or delayed symptoms of infection; it does not imply that there must have been no penetration of any cell by the infecting microorganism (i.e., *P. gingivalis*).

When the terms treat and treating are used herein in connection with a given treatment for a given condition (e.g., treating an infection, or a disease (symptomatic infection) caused by *P. gingivalis*), it is meant to convey that the treated subject displays either no clinically observable level of the condition or displays it to a lesser degree than he did before the treatment. A treatment can "treat" an infection or disease by resulting in the subject displaying milder overt symptoms of the infection; it does not imply that there must have been a complete eradication of the infecting microorganism (i.e., *P. gingivalis*).

P. gingivalis Polypeptides and Nucleic Acids

The present invention provides isolated polypeptides and nucleic acids derived from *P. gingivalis* which are useful inter alia as components in immunogenic compositions, and/or as reagents for diagnosing *P. gingivalis* infections (e.g. as probes). Preferred embodiments of the present invention include one or more polypeptides of PG0495, PG0654, PG1374, PG1795, PG2172, PG0613, PG1326, PG1798, PG0186 and PG0616 and isolated nucleic acids encoding these polypeptides. Each of PG0495, PG0654, PG1374, PG1795, PG2172, PG0613, PG1326, PG1798, PG0186 and PG0616 were identified by mining the genome of the *P. gingivalis* W83 strain for candidates which were then isolated from the *P. gingivalis* W50 strain (ATCC 53978) using parameters and procedures described in more detail in Example 1.

Compositions of the present invention comprise at least one polypeptide of PG0495, PG0654, PG1374, PG1795, PG2172, PG0613, PG1326, PG1798, PG0186 and PG0616. For each of PG0495, PG0654, PG1374, PG1795, PG2172, PG0613, PG1326, PG1798, PG0186 and PG0616, polypeptides suitable for use comprise the full length amino acid sequence (in the presence or absence of signal sequence), and immunogenic fragments, variants (naturally occurring or otherwise, e.g., synthetically derived), and fusion proteins thereof.

PG0495 polypeptides suitable for use in the compositions described herein may be isolated or derived from the *P. gingivalis* strains W83, W50 and ATCC33277, and any other strain expressing PG0495. PG0495 is also known as PGN_1476. The amino acid sequence of full length P0495 in the *P. gingivalis* W83 genome is accessible via GenBank Accession No. AAQ65689.1 and is provided in the Sequence Listing herein as SEQ ID NO.1. Preferred P0495 polypeptides for use with the invention comprise an amino acid sequence having 50% or more identity (e.g., 60, 65, 70, 75, 80, 85, 90, 91, 92, 93, 94, 95, 96, 97, 98, 99, 99.5% or more) to SEQ ID NO:1. Preferred polypeptides for use with the invention comprise a fragment of at least 8, 9, 10, 12, 13, 16, 18, 20, 25, 30, 35, 40, 50, 60, 70, 80, 90, 100, 150, 200, 250 or more consecutive amino acids of SEQ ID NO.1. Preferred fragments comprise an epitope from SEQ ID NO:1. Other preferred fragments lack one or more acids from the N-terminus of SEQ ID NO:1 (e.g., 1, 2, 3, 4, 5, 6, 7, 8, 9, 10, 15, 20, 25 or more) and/or one or more amino acids from the C-terminus of SEQ ID NO:1 while retaining at least one epitope of SEQ ID NO:1. Further preferred polypeptides lack the signal sequence from the N-terminus of SEQ ID NO:1.

PG0654 polypeptides suitable for use in the compositions described herein may be isolated or derived from the *P. gingivalis* strains W83, W50 and ATCC33277, and any other strain expressing PG0654. PG0654 is also known as PGN_0693. The amino acid sequence of full length P0654 in the *P. gingivalis* W83 genome is accessible via GenBank Accession No. AAQ656833.1 and is also set out in the Sequence listing herein as SEQ ID NO.9. Preferred P0654 polypeptides for use with the invention comprise an amino acid sequence having 50% or more identity (e.g., 60, 65, 70, 75, 80, 85, 90, 91, 92, 93, 94, 95, 96, 97, 98, 99, 99.5% or more) to SEQ ID NO:9. Preferred polypeptides for use with the invention comprise a fragment of at least 8, 9, 10, 12, 13, 16, 18, 20, 25, 30, 35, 40, 50, 60, 70, 80, 90, 100, 150, 200, 250 or more consecutive amino acids of SEQ ID NO.9. Preferred fragments comprise an epitope from SEQ ID NO:9 Other preferred fragments lack one or more acids from the N-terminus of SEQ ID NO:9 (e.g., 1, 2, 3, 4, 5, 6, 7, 8, 9, 10, 15, 20, 25 or more) and/or one or more amino acids from the C-terminus of SEQ ID NO:9 while retaining at least one epitope of SEQ ID NO:9. Further preferred polypeptides lack the signal sequence from the N-terminus of SEQ ID NO:9.

PG1374 polypeptides suitable for use in the compositions described herein may be isolated or derived from the *P. gingivalis* strains W83, W50 and ATCC33277, and any other strain expressing PG1374. PG1374 is also known as PGN_0852. The amino acid sequence of full length P1374 in the *P. gingivalis* W83 genome is accessible via GenBank Accession No. AAQ66438.1 and is also set out in the Sequence Listing herein as SEQ ID NO.7. Preferred P1374 polypeptides for use with the invention comprise an amino acid sequence having 50% or more identity (e.g., 60, 65, 70, 75, 80, 85, 90, 91, 92, 93, 94, 95, 96, 97, 98, 99, 99.5% or more) to SEQ ID NO:7. Preferred polypeptides for use with the invention comprise a fragment of at least 8, 9, 10, 12, 13, 16, 18, 20, 25, 30, 35, 40, 50, 60, 70, 80, 90, 100, 150, 200, 250 or more consecutive amino acids of SEQ ID NO.7. Preferred fragments comprise an epitope from SEQ ID NO:7 Other preferred fragments lack one or more acids from the N-terminus of SEQ ID NO:7 (e.g., 1, 2, 3, 4, 5, 6, 7, 8, 9, 10, 15, 20, 25 or more) and/or one or more amino acids from the C-terminus of SEQ ID NO:7 while retaining at least one epitope of SEQ ID NO:7. Further preferred polypeptides lack the signal sequence from the N-terminus of SEQ ID NO:7.

PG1795 polypeptides suitable for use in the compositions described herein may be isolated or derived from the *P. gingivalis* strains W83, W50 and ATCC33277, and any other strain expressing PG1795. PG1795 is also known as PGN_1770. The amino acid sequence of full length P1795 in the *P. gingivalis* W83 genome is accessible via GenBank Accession No. AAQ66795.1 and is also set out in the Sequence Listing herein as SEQ ID NO.17. Preferred P1795 polypeptides for use with the invention comprise an amino acid sequence having 50% or more identity (e.g., 60, 65, 70, 75, 80, 85, 90, 91, 92, 93, 94, 95, 96, 97, 98, 99, 99.5% or more) to SEQ ID NO:17. Preferred polypeptides for use with the invention comprise a fragment of at least 8, 9, 10, 12, 13, 16, 18, 20, 25, 30, 35, 40, 50, 60, 70, 80, 90, 100, 150, 200, 250 or more consecutive amino acids of SEQ ID NO.17. Preferred fragments comprise an epitope from SEQ ID NO:17 Other preferred fragments lack one or more acids from the N-terminus of SEQ ID NO:17 (e.g., 1, 2, 3, 4, 5, 6, 7, 8, 9, 10, 15, 20, 25 or more) and/or one or more amino acids from the C-terminus of SEQ ID NO:17 while retaining at least one epitope of SEQ ID NO:17. Further preferred polypeptides lack the signal sequence from the N-terminus of SEQ ID NO:17.

PG2172 polypeptides suitable for use in the compositions described herein may be isolated or derived from the *P. gingivalis* strains W83, W50 and ATCC33277, and any other strain expressing PG2172. PG2172 is also known as PGN_0123. The amino acid sequence of full length P2172 in the *P. gingivalis* W83 genome is accessible via GenBank Accession No. AAQ67121.1 and is also set out in the Sequence Listing herein as SEQ ID NO.3. Preferred P2172 polypeptides for use with the invention comprise an amino acid sequence having 50% or more identity (e.g., 60, 65, 70, 75, 80, 85, 90, 91, 92, 93, 94, 95, 96, 97, 98, 99, 99.5% or more) to SEQ ID NO:3. Preferred polypeptides for use with the invention comprise a fragment of at least 8, 9, 10, 12, 13, 16, 18, 20, 25, 30, 35, 40, 50, 60, 70, 80, 90, 100, 150, 200, 250 or more consecutive amino acids of SEQ ID NO.3. Preferred fragments comprise an epitope from SEQ ID NO:3 Other preferred fragments lack one or more acids from the N-terminus of SEQ ID NO:3 (e.g., 1, 2, 3, 4, 5, 6, 7, 8, 9, 10, 15, 20, 25 or more) and/or one or more amino acids from the C-terminus of SEQ ID NO:3 while retaining at least one epitope of SEQ ID NO:3. Further preferred polypeptides lack the signal sequence from the N-terminus of SEQ ID NO:3.

PG0613 polypeptides suitable for use in the compositions described herein may be isolated or derived from the *P. gingivalis* strains W83, W50 and ATCC33277, and any other strain expressing PG0613. PG0613 is also known as PGN_0656. The amino acid sequence of full length P0613 in the *P. gingivalis* W83 genome is available via GenBank Accession No. AAQ65797.1 and is also set out in the Sequence Listing herein as SEQ ID NO.11. Preferred P0613 polypeptides for use with the invention comprise an amino acid sequence having 50% or more identity (e.g., 60, 65, 70, 75, 80, 85, 90, 91, 92, 93, 94, 95, 96, 97, 98, 99, 99.5% or more) to SEQ ID NO:11. Preferred polypeptides for use with the invention comprise a fragment of at least 8, 9, 10, 12, 13, 16, 18, 20, 25, 30, 35, 40, 50, 60, 70, 80, 90, 100, 150, 200, 250 or more consecutive amino acids of SEQ ID NO.11. Preferred fragments comprise an epitope from SEQ ID NO:11 Other preferred fragments lack one or more acids from the N-terminus of SEQ ID NO:11 (e.g., 1, 2, 3, 4, 5, 6, 7, 8, 9, 10, 15, 20, 25 or more) and/or one or more amino acids from the C-terminus of SEQ ID NO:11 while retaining at least one epitope of SEQ ID NO:11. Further preferred polypeptides lack the signal sequence from the N-terminus of SEQ ID NO:11.

PG1326 polypeptides suitable for use in the compositions described herein may be isolated or derived from the *P. gingivalis* strains W83, W50, and ATCC33277, and any other strain expressing PG1326. PG1326 is also known as PGN_1115. The amino acid sequence of full length P1326 in the *P. gingivalis* W83 genome is accessible via GenBank Accession No. AAQ66396.1 and is also set out herein as SEQ ID NO.5. Preferred P1326 polypeptides for use with the invention comprise an amino acid sequence having 50% or more identity (e.g., 60, 65, 70, 75, 80, 85, 90, 91, 92, 93, 94, 95, 96, 97, 98, 99, 99.5% or more) to SEQ ID NO:5. Preferred polypeptides for use with the invention comprise a fragment of at least 8, 9, 10, 12, 13, 16, 18, 20, 25, 30, 35, 40, 50, 60, 70, 80, 90, 100, 150, 200, 250 or more consecutive amino acids of SEQ ID NO.5. Preferred fragments comprise an epitope from SEQ ID NO:5 Other preferred fragments lack one or more acids from the N-terminus of SEQ ID NO:5 (e.g., 1, 2, 3, 4, 5, 6, 7, 8, 9, 10, 15, 20, 25 or more) and/or one or more amino acids from the C-terminus of SEQ ID NO:5 while retaining at least one epitope of SEQ ID NO:5. Further preferred polypeptides lack the signal sequence from the N-terminus of SEQ ID NO:5.

PG1798 polypeptides suitable for use in the compositions described herein may be isolated or derived from the *P. gingivalis* strains W83, W50 and ATCC33277, and any other strain expressing PG1798. PG1798 is also known as PGN_1767. The amino acid sequence of full length P1798 in the *P. gingivalis* W83 genome is accessible via GenBank Accession No. AAQ66797.1 and is set out in the Sequence Listing herein as SEQ ID NO.13. Preferred P1798 polypeptides for use with the invention comprise an amino acid sequence having 50% or more identity (e.g., 60, 65, 70, 75, 80, 85, 90, 91, 92, 93, 94, 95, 96, 97, 98, 99, 99.5% or more) to SEQ ID NO:13. Preferred polypeptides for use with the invention comprise a fragment of at least 8, 9, 10, 12, 13, 16, 18, 20, 25, 30, 35, 40, 50, 60, 70, 80, 90, 100, 150, 200, 250 or more consecutive amino acids of SEQ ID NO:13. Preferred fragments comprise an epitope from SEQ ID NO:13. Other preferred fragments lack one or more acids from the N-terminus of SEQ ID NO:13 (e.g., 1, 2, 3, 4, 5, 6, 7, 8, 9, 10, 15, 20, 25 or more) and/or one or more amino acids from the C-terminus of SEQ ID NO:13 while retaining at least one epitope of SEQ ID NO:13. Further preferred polypeptides lack the signal sequence from the N-terminus of SEQ ID NO:13.

PG0186 polypeptides suitable for use in the compositions described herein may be isolated or derived from the *P. gingivalis* strains W83, W50 and ATCC33277, and any other strain expressing PG0186. PG0186 is also known as PGN_0294. The amino acid sequence of full length P0186 in the *P. gingivalis* W83 genome is accessible via GenBank Accession No. AAQ65421.1 and is also set out in the Sequence Listing herein as SEQ ID NO.15. Preferred P0186 polypeptides for use with the invention comprise an amino acid sequence having 50% or more identity (e.g., 60, 65, 70, 75, 80, 85, 90, 91, 92, 93, 94, 95, 96, 97, 98, 99, 99.5% or more) to SEQ ID NO:15. Preferred polypeptides for use with the invention comprise a fragment of at least 8, 9, 10, 12, 13, 16, 18, 20, 25, 30, 35, 40, 50, 60, 70, 80, 90, 100, 150, 200, 250 or more consecutive amino acids of SEQ ID NO.?. Preferred fragments comprise an epitope from SEQ ID NO:15. Other preferred fragments lack one or more acids from the N-terminus of SEQ ID NO:15 (e.g., 1, 2, 3, 4, 5, 6, 7, 8, 9, 10, 15, 20, 25 or more) and/or one or more amino acids from the C-terminus of SEQ ID NO:15 while retaining at least one epitope of SEQ ID NO:15. Further preferred polypeptides lack the signal sequence from the N-terminus of SEQ ID NO:15.

PG0616 polypeptides suitable for use in the compositions described herein may be isolated or derived from the *P. gingivalis* strains W83, W50 and ATCC33277, and any other strain expressing PG0616. PG0616 is also known as PGN_0659. The amino acid sequence of full length P0616 in the *P. gingivalis* W83 genome is accessible via GenBank Accession No. AAQ65800.1 and is also set out in the Sequence Listing herein as SEQ ID NO.19. Preferred P0616 polypeptides for use with the invention comprise an amino acid sequence having 50% or more identity (e.g., 60, 65, 70, 75, 80, 85, 90, 91, 92, 93, 94, 95, 96, 97, 98, 99, 99.5% or more) to SEQ ID NO:19. Preferred polypeptides for use with the invention comprise a fragment of at least 8, 9, 10, 12, 13, 16, 18, 20, 25, 30, 35, 40, 50, 60, 70, 80, 90, 100, 150, 200, 250 or more consecutive amino acids of SEQ ID NO.19. Preferred fragments comprise an epitope from SEQ ID NO:19 Other preferred fragments lack one or more acids from the N-terminus of SEQ ID NO:19 (e.g., 1, 2, 3, 4, 5, 6, 7, 8, 9, 10, 15, 20, 25 or more) and/or one or more amino acids from the C-terminus of SEQ ID NO:19 while retaining at least one epitope of SEQ ID NO:19. Further preferred polypeptides lack the signal sequence from the N-terminus of SEQ ID NO:19.

The invention includes polynucleotides that encode a polypeptide of the invention and polynucleotides which hybridize, under standard hybridization conditions, to a polynucleotide that encodes a polypeptide of the invention, and the complements of such polynucleotide sequence. Also included in the present invention are polynucleotides having sequence identity of at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, sequence identity to an identified reference nucleic acid sequence, such as with any of SEQ ID NOs: 2, 4, 6, 8, 10, 12, 14, 16, 18, 20, 22, 24, 26, 28, 30, 32, 34, 36, 38, and 40. The nucleic acids of the present invention, isolated or synthesized in accordance with the sequences disclosed herein are useful in the recombinant production of *P. gingivalis* peptides or polypeptides.

The nucleic acids of this invention may be obtained directly from the DNA of a *P. gingivalis* strain (such as for example, but not limited to, *P. gingivalis* strains W83, W50 and ATCC33277) and any other *P. gingivalis* strain carrying the applicable DNA gene sequence by using the polymerase chain reaction (PCR) (as described in PCR, A Practical Approach" (McPherson, Quirke, and Taylor, eds. IRL Press Oxford, UK, 1991) or by using alternative standard techniques that are recognized by one skilled in the art. One embodiment of the invention provides isolated nucleic acids molecules having a sequence corresponding to any of SEQ ID NOs: 2, 4, 6, 8, 10, 12, 14, 16, 18, 22, 24, 26, 28, 30, 32, 34, 36, 38, and 40. The invention encompasses sequence-conservative variants and function-conservative variants of these sequences.

The polypeptides of the present invention encompass those encoded by the disclosed isolated nucleic acids including the polypeptides of SEQ ID NOs. 1, 3, 5, 7, 9, 11, 13, 15, 17, 19, 21, 23, 25, 27, 29, 31, 35, 37, and 39 and their variants. The polypeptides of the present invention, including function-conservative variants, preferably correspond to proteins which are surface accessible on *P. gingivalis*.

The polypeptides of the present invention can be produced using standard molecular biology techniques and expression systems (see for example, *Molecular Cloning: A Laboratory Manual*, Third Edition by Sambrook et. al., Cold Spring Harbor Press, 2001). For example, the gene (or the fragment of a gene) that encodes an immunogenic polypeptide may be isolated and the polynucleotides encoding the immunogenic polypeptide may be cloned into any commercially available expression vector (such as, e.g., pBR322 and pUC vectors (New England Biolabs, Inc., Ipswich, Mass.) or expression/purification vectors (such as e.g., GST fusion vectors (Pfizer, Inc., Piscataway, N.J., or those described in the Examples herein) and then expressed in a suitable prokaryotic, viral or eukaryotic host. Purification may then be achieved by conventional means, or in the case of a commercial expression/purification system, in accordance with manufacturer's instructions.

Alternatively, the polypeptides of the present invention, including variants, may be isolated for example, but without limitation, from wild-type or mutant *P. gingivalis* cells, or through chemical synthetization using commercially automated procedures, such as for example, exclusive solid phase synthesis, partial solid phase methods, fragment condensation or solution synthesis.

Polypeptides of the present invention preferably have immunogenic activity. "Immunogenic activity" refers to the ability of a polypeptide to elicit an immunological response in a subject. An immunological response to a polypeptide is the development in a subject of a cellular and/or antibody-mediated immune response to the polypeptide. Usually, an immunological response includes but is not limited to one or more of the following effects: the product of antibodies, B cells, helper T cells, suppressor T cells and/or cytotoxic T cells, directed to an epitope or epitopes of the polypeptide. The term "Epitope" refers to the site on an antigen to which specific B cells and/or T cells respond so that antibody is produced. The immunogenic activity may be protective. The term "protective immunogenic activity" refers to the ability of a polypeptide to elicit an immunological response in a subject that prevents or inhibits infection by *P. gingivalis*.

A polypeptide of the present invention may be characterized by molecular weight, mass fingerprint, amino acid sequence, nucleic acid sequence that encodes the polypeptide, immunological activity, or any combination of two or more such characteristics. The molecular weight of a polypeptide, typically expressed in kilodaltons (kDa), can be determined using routine methods including, for instance, gel filtration, gel electrophoresis including sodium dodecyl sulfate (SDS) polyacrylamide gel electrophoresis (PAGE), capillary electrophoresis, mass spectrometry, liquid chromatography (including HPLC), and calculating the molecular weight from an observed or predicted amino acid sequence.

In one embodiment, nucleic acids encoding a polypeptide such as any of SEQ ID NOs. 1, 3, 5, 7, 9, 11, 13, 15, 17, 19, 21, 23, 25, 27, 29, 31, 35, 37, and 39 or variants thereof are provided. Also provided are variants of such sequences, including degenerate variants thereof. In certain embodiments, a nucleic acid molecule encoding the polypeptide and/or fragment thereof may be inserted into one or more expression vectors, as discussed below in greater detail. In such embodiments, the polypeptide and/or fragment is/are encoded by nucleotides corresponding to the amino acid sequence. The particular combinations of nucleotides that encode the various amino acids are well known in the art, as described in various references used by those skilled in the art (.e.g., Lewin, B. Genes V, Oxford University Press, 1994, and later editions), as shown in Table 1 below. Nucleic acid variants may use any combination of nucleotides that encode the polypeptide of interest.

TABLE 1

| Phe (F) | TTT | Ser (S) | TCT | Tyr (Y) | TAT | Cys (C) | TGT |
|---|---|---|---|---|---|---|---|
| | TTC | | TCC | | TAC | | TGC |
| Leu (L) | TTA | | TCA | TERM | TAA | TERM | TGA |
| | TTG | | TCG | | TAG | Trp (W) | TGG |
| | CTT | Pro (P) | CCT | His (H) | CAT | Arg (R) | CGT |
| | CTC | | CCC | | CAC | | CGC |
| | CTA | | CCA | Gln (Q) | CAA | | CGA |
| | CTG | | CCG | | CAG | | CGG |
| Ile (I) | ATT | Thr (T) | ACT | Asn (N) | AAT | Ser (S) | AGT |
| | ATC | | ACC | | AAC | | AGC |
| | ATA | | ACA | Lys (K) | AAA | Arg (R) | AGA |
| Met (M) | ATG | | ACG | | AAG | | AGG |
| Val (V) | GTT | Ala (A) | GCT | Asp (D) | GAT | Gly (G) | GGT |
| | GTC | | GCC | | GAC | | GGC |
| | GTA | | GCA | Glu (E) | GAA | | GGA |
| | GTG | | GCG | | GAG | | GGG |

The immunogenic polypeptides of PG0495, PG0654, PG1374, PG1795, PG2172, PG0613, PG1326, PG1798, PG0186 and PG0616 described herein include immunogenic fragments and variants of such polypeptides and/or fragments. Variants may comprise amino acid modifications. For example, amino acid sequence modifications include substitutional, insertional or deletion changes. Substitutions, deletions, insertions or any combination thereof may be combined in a single variant so long as the variant is immunogenic. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal or one or more amino acid residues from the protein sequence. Typically no more than about from 2 to 6 residues are deleted at any one site within the protein molecule. These variants ordinarily are prepared by site specific mutagenesis of nucleotides in the DNA encoding the protein, thereby producing DNA encoding the variant and thereafter expressing the DNA in a recombinant cell culture.

Techniques for making substitutional mutations at predetermined sites in DNA having a known sequence are well known and include, but are not limited to, M13 primer mutagenesis and PCT mutagenesis. Amino acid substitutions are typically single residues but can occur at a number of different locations. Substitutional variants are those in which at least one residue has been removed and a different residue inserted in its place. Such substitutions generally are made in accordance with the following Table 2 and are referred to as conservative substitutions (although non-conservative substitutions are also possible). Others are well known to those of skill in the art.

Conservative amino acid substitutions may involve a substitution of a native amino acid residue with a non-native residue such that there is little or no effect on the size, polarity, charge, hydrophobicity, or hydrophilicity of the amino acid residue at that position and, in particular, does not result in decreased immunogenicity. Suitable conservative amino acid substitutions are shown in Table 2.

TABLE 2

| Original Residues | Exemplary Conservative Substitutions | Preferred Conservative Substitution |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The specific amino acid substitution selected may depend on the location of the site selected. In certain embodiments, nucleotides encoding polypeptides and/or fragments substituted based on the degeneracy of the genetic code (i.e, consistent with the "Wobble" hypothesis). Where the nucleic acid is a recombinant DNA molecule useful for expressing a polypeptide in a cell (e.g., an expression vector), a Wobble-type substitution will result in the expression of a polypeptide with the same amino acid sequence as that originally encoded by the DNA molecule. As described above, however, substitutions may be conservative, or non-conservative, or any combination thereof.

A skilled artisan will be able to determine suitable variants of the polypeptides and/or fragments provided herein using well-known techniques. For identifying suitable areas of the molecule that may be changed without destroying biological activity (e.g. immunogenicity, MHC binding, red blood cell (RBC) agglutination, RBC hemolysis), one skilled in the art may target areas not believed to be important for that activity. For example, when derivatives with similar activities from the same species or from other species are known, one skilled in the art may compare the amino acid sequence of a polypeptide to such similar polypeptides. By performing such analyses, one can identify residues and portions of the molecules that are conserved. It will be appreciated that changes in areas of the molecule that are not conserved relative to such similar derivatives would be less likely to adversely affect the biological activity and/or structure of a polypeptide. However, modifications resulting in decreased binding to MHC will not be appropriate in most situations. One skilled in the art would also know that, even in relatively conserved regions, one may substitute chemically similar amino acids for the naturally occurring residues while retaining the desired characteristics of the polypeptide and/or fragment. Therefore, even areas that may be important for biological activity or for structure may be subject to conservative amino acid substitutions without destroying the biological activity or without adversely affecting the structure of the derivative.

Analogs can differ from naturally occurring *P. gingivalis* polypeptides in amino acid sequence and/or by virtue of non-sequence modifications. Non-sequence modifications include changes in acetylation, methylation, phosphyorylation, carboxylation, or glycosylation. A "modification" of a polypeptide of the present invention includes polypeptides (or analogs thereof, such as, e.g. fragments thereof) that are chemically or enzymatically derivatized at one or more constituent amino acid. Such modifications can include, for example, side chain modifications, backbone modifications, and N- and C-terminal modifications such as, for example, acetylation, hydroxylation, methylation, amidation, and the attachment of carbohydrate or lipid moieties, cofactors, and the like, and combinations thereof. Modified polypeptides of the invention may retain the biological activity of the unmodified polypeptides or may exhibit a reduced or increased biological activity.

Polypeptide Sequence Similarity and Polypeptide Sequence Identity

Structural similarity of two polypeptides can be determined by aligning the residues of the two polypeptides (for example, a candidate polypeptide and the polypeptide of, for example, SEQ ID NO: 1) to optimize the number of identical amino acids along the length of their sequences; gaps in either or both sequences are permitted in making the alignment in order to optimize the number of identical amino acids, although the amino acids in each sequence must nonetheless remain in their proper order. A candidate polypeptide is the polypeptide being compared to the reference polypeptide. A candidate polypeptide can be isolated, for example, from a microbe (e.g., *P. gingivalis*), or can be produced using a recombinant techniques, or chemically or enzymatically synthesized.

A pair-wise comparison analysis of amino acids sequences can be carried out using a global algorithm for example Needleman-Wunsch. Alternatively, polypeptides may be compared using a local alignment algorithm such as the Blastp program of the BLAST 2 search algorithm, as described by Tatiana et al., (*FEMS Microbiol. Lett,* 174:247-250 (1999), and available on the National Centre for Biotechnology Information (NCBI) website. The default values for all BLAST 2 search parameters may be used, including matrix=BLOSUM62; open gap penalty=11, extension gap penalty=1, gap×dropoff=50, expect 10, wordsize=3, and filter on. The Smith and Waterman algorithm is another local alignment tool that can be used (1988).

In comparison of two amino acid sequences, structural similarly may be referred to by percent "identity" or may be referred to by percent "similarity." "Identity" refers to the presence of identical amino acids. Unless otherwise stated, the term "percent identity" means that a pair-wise comparison analysis of two amino acids was carried out using a global algorithm. "Similarity" refers to the presence of not only identical amino acids but also the presence of conservative substitutions. A conservative substitution for an amino acid in a polypeptide of the invention may be selected from other members of the class to which the amino acid belongs, as shown on Table 2.

A polypeptide of the present invention can include a polypeptide with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or least 99%, amino acid sequence identity to the reference amino acid sequence.

Fusions

In other embodiments, the polypeptides and/or fragments described herein may include fusion polypeptide segments that assist in purification or detection of the polypeptides. Fusions can be made either at the amino terminus or at the carboxy terminus of the subject polypeptide variant thereof. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derived according to the methods described herein. Suitable fusion segments include, among others, metal binding domains (e.g., a poly histidine segment), immunoglobulin binding domains (i.e., Protein A, Protein G, T cell, B cell, Fc receptor, or complement protein antibody binding domains), sugar binding domains (e.g., a maltose binding domain), and/or a "tag" domain (i.e., at least a portion of galactosidase, a strep tag peptide, a T7 tag peptide, a FLAG peptide, or other domains that can be purified using compounds that bind to the domain, such as monoclonal antibodies). This tag is typically fused to the polypeptide upon expression of the polypeptide, and can serve as a means for affinity purification of the sequence of interest polypeptide from the host cell. Affinity purification can be accomplished, for example, by column chromatography using antibodies against the tag as an affinity matrix. Optionally, the tag can subsequently be removed from the purified sequence of interest polypeptide by various means such as using certain peptidases for cleavage. Examples of fusion proteins with a segment/domain attached at the N-terminus to aid in purification are provided here (see e.g., SEQ ID NOs: 21, 23, 25, 27, 29, 31, 35, 37, and 39).

In certain embodiments, the polypeptides and/or fragments may be directly or indirectly (i.e., using an antibody) labeled or tagged in a manner which enables it to be detected. Labels include fluorochromes such as fluorescein, rhodamine, phycoerythrin, Europium and Texas Red, chromogenic dyes such as diaminobenzidine, radioisotopes, macromolecular colloidal particles or particulate material such as latex beads that are coloured, magnetic or paramagnetic, binding agents such as biotin and digoxigenin, and biologically or chemically active agents that can directly or indirectly cause detectable signals to be visually observed, electronically detected or otherwise recorded, for example in a FACS, ELISA, Western blot, TRFIA, immunohistochemistry, evanescence, Luminex bead array, or dipstick or other lateral flow assay format. Suitable antibody-binding molecules for use in such methods may include immunoglobulin-binding antibodies, for example anti-human Ig antibodies, anti-human Ig antibodies, anti-human antibodies specific for Ig isotypes or for subclasses of IgG, or specific for *P. gingivalis* proteins.

Preferred fluorescent tag proteins include those derived from the jelly fish protein known as green fluorescent protein (GFP). Further information on GFP and other fluorophores is given in the following publications: Tsien R Y, "The Green Fluorescent Protein" Annual Reviews of Biochemistry 1998; 67:509-544 Verkhusha, V. and Lukyanov, K. "The Molecular Properties and Applications of Anthoza Fluorescent Proteins and Chromophores" Nature Biotechnology 2004; 22:289-296. Plasmid vectors encoding a wide range of fluorescent tag proteins are commercially available from various suppliers including an array of "Living Colours™ Fluorescent Proteins" available commercially from Clontech Laboratories, Inc. Similar vectors can also be obtained from other suppliers including Invitrogen and Amersham Biosciences. Suitable fluorescent proteins derived from GFP are the red-shifted variant EGFP, the cyan shifted variant ECFP and the yellow shifted variant EYFP. EGFP is preferred as the fluorescent marker because it gives bright fluorescence combined with minimal effect on the antigenic properties of the target antigen. Alternative fluorescent marker proteins are commercially available. Biologically or chemically active agents include enzymes, which catalyse reactions that develop or change colours or cause changes in electrical properties, for example, and may also be utilized. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. Further examples include horseradish peroxidase and chemiluminescence. In some embodiments, the non-immobilised antibody-binding molecule or polypeptide may be detected using an antibody which binds to said non-immobilised antibody-binding molecule or polypeptide. A suitable detection antibody may be labeled by means of fluorescence. The label may be a fluorescent marker (tag) which is used to label the target antigen directly such that the antigen and the fluorescent marker form a fusion protein.

If antibodies against the target antigen are present in a biological sample, the antigen may be labeled with the tag bound to those antibodies, and the complex formed thereby detected using immunoprecipitation. The fluorescence associated with the tag may then be used to determine that protein has been precipitated (qualitative determination) or to determine the amount of protein precipitated (quantitative determination). For example, soluble extracts of a fluorescence-tagged antigen may be incubated with patient sera for an appropriate period of time such as overnight at 4° C. (typically 10-15 µl of serum to 300-500 µl of extract or less) to allow antibodies to bind to the antigen. Protein A or Protein G Sepharose beads, preincubated with low IgG fetal calf serum (Sigma) to block non-specific binding, are then added to the extract/serum mix containing the tagged protein/antibody complexes, and mixed with gentle rotation for 1 to 2 hours at room temperature. The antibodies within the serum, including those that specifically bind the tagged protein, are bound by the protein A/G beads. The protein A/G Sepharose beads are then washed in a suitable buffer (typically 10 mM Tris-HCl pH 7.4, 100 mM NaCl/1mM EDTA/1% Triton X-100) to remove any unbound tagged protein. This may be achieved by three rounds of centrifugation, removal of the supernatant, and resuspension in buffer. The beads, some with tagged protein attached, are then collected and placed in a fluorescence reader, for example a Spectra Max Gemini XS plate reader from Molecular Devices Inc. The presence of specific autoantibodies/antibodies in the original serum sample is quantitated. In the case of GFP this uses excitation at wavelength 472 nm and emission at 512 nm. The fluorescence excitation will depend upon the fluorophore/tag that is used but it would be possible to combine several different tagged proteins in the same time. For example, different *P. gingivalis* polypeptides (and/or fragments thereof) may be separately tagged and separately or simultaneously assayed. The sensitivity of the method is dependent on the detection device and can be considerably enhanced by using more sensitive detection devices. Various modifications of these methods could also be utilized.

The assays described herein for detecting antibodies immunoreactive with *P. gingivalis* antigens may also be combined with other assays useful for detecting *P. gingivalis* infection. For instance, these assays (i.e., ELISA) may be combined with polymerase chain reaction (PCR) assays for detecting *P. gingivalis* nucleic acid in a biological sample. Alternatively, an ELISA assay may be combined with an immunoprecipitation assay, or a PCR-based assay may be combined with an immunoprecipitation assay. Combining the various assays described herein may serve to even further increase the sensitivity of detection and further decrease the negative predictive value of the data.

Expression Vectors

The present invention further provides for the use of expression vectors. Expression vectors are typically comprised of a flanking sequence operably linked to a heterologous nucleic acid sequence encoding a polypeptide (the "coding sequence"). In other embodiments, or in combination with such embodiments, a flanking sequence is preferably capable of effecting the replication, transcription and/or translation of the coding sequence and is operably linked to a coding sequence. To be "operably linked" indicates that the nucleic acid sequences are configured so as to perform their usual function. For example, a promoter is operably linked to a coding sequence when the promoter is capable of directing transcription of that coding sequence. The promoter elements that may be present include those naturally associated with the nucleotide sequence encoding the polypeptide and exogenous elements not associated with the nucleotide sequence.

A flanking sequence need not be contiguous with the coding sequence, so long as it functions correctly. Thus, for example, intervening untranslated yet transcribed sequences can be present between a promoter sequence and the coding sequence and the promoter sequence can still be considered operably linked to the coding sequence. Flanking sequences may be homologous (i.e., from the same species and/or strain as the host cell), heterologous (i.e., from a species other than the host cell species or strain), hybrid (i.e., a combination of flanking sequences from more than one source), or synthetic. A flanking sequence may also be a sequence that normally functions to regulate expression of the nucleotide sequence encoding the polypeptide in the genome of the host may also be utilized.

A cultured cell comprising the vector is also provided. The cultured cell may be a cultured cell transfected with the vector or a progeny of the cell, wherein the cell expresses the immunogenic polypeptide. Suitable cell lines are known to those of skill in the art and are commercially available, for example, through the American Type Culture Collection (ATCC). The *P. gingivalis* nucleotide sequences can be expressed in a variety of expression systems, such as for example, those used with mammalian cells, baculoviruses, plants, bacteria and yeast. The transfected cells can be used in a method of producing an immunogenic polypeptide. The method comprises culturing a cell comprising the vector under conditions that allow expression of the polypeptide, optionally under the control of an expression sequence. The polypeptide can be isolated from the cell or the culture medium using standard protein purification methods.

Delivery Techniques

In certain embodiments, it is preferred that the flanking sequence is a transcriptional regulatory region that drives high-level gene expression in the target cell. The transcriptional regulatory region may comprise, for example, a promoter, enhancer, silencer, repressor element, or combinations thereof. The transcriptional regulatory region may be either constitutive or tissue- or cell-type specific (i.e., the region drives higher levels of transcription in one type of tissue or cell as compared to another). As such, the source of a transcriptional regulatory region may be any prokaryotic or eukaryotic organism, any vertebrate or invertebrate organism, or any plant, provided that the flanking sequence is functional in, and can be activated by, the host cell machinery. A wide variety of transcriptional regulatory regions may be utilized.

Suitable transcriptional regulatory regions include, among others, the CMV promoter (i.e., the CMV-immediate early promoter); promoters from eukaryotic genes (i.e., the estrogen-inducible chicken ovalbumin gene, the interferon genes, the gluco-corticoid-inducible tyrosine aminotransferase gene, and the thymidine kinase gene); and the major early and late adenovirus gene promoters; the SV40 early promoter region (Bernoist and Chambon, 1981, Nature 290:304-10); the promoter contained in the 3' long terminal repeat (LTR) of Rous sarcoma virus (RSV) (Yamamoto, et al., 1980, Cell 22:787-97); the herpes simplex virus thymidine kinase (HSV-TK) promoter (Wagner et al., 1981, Proc. Natl. Acad. Sci. U.S.A. 78:1444-45); the regulatory sequences of the metallothionine gene (Brinster et al., 1982, Nature 296:39-42); prokaryotic expression vectors such as the beta-lactamase promoter (Villa-Kamaroff et al., 1978, Proc. Natl. Acad. Sci. U.S.A., 75:3727-31); or the tac promoter (DeBoer et al., 1983, Proc. Natl. Acad. Sci. U.S.A., 80:21-25). Tissue- and/or cell-type specific transcriptional control regions include, for example, the elastase I gene control region which is active in pancreatic acinar cells (Swift et al., 1984, Cell 38:639-46; Ornitz et al., 1986, Cold Spring Harbor Symp. Quant. Biol. 50:399-409 (1986); MacDonald, 1987, Hepatology 7:425-515); the insulin gene control region which is active in pancreatic beta cells (Hanahan, 1985, Nature 315:115-22); the immunoglobulin gene control region which is active in lymphoid cells (Grosschedl et al., 1984, Cell 38:647-58; Adames et al., 1985, Nature 318:533-38; Alexander et al., 1987, Mol. Cell. Biol., 7:1436-44); the mouse mammary tumor virus control region in testicular, breast, lymphoid and mast cells (Leder et al., 1986, Cell 45:485-95); the albumin gene control region in liver (Pinkert et al., 1987, Genes and Devel. 1:268-76); the alpha-feto-protein gene control region in liver (Krumlauf et al., 1985, Mol. Cell. Biol., 5:1639-48; Hammer et al., 1987, Science 235:53-58); the alpha 1-antitrypsin gene control region in liver (Kelsey et al., 1987, Genes and Devel. 1:161-71); the beta-globin gene control region in myeloid cells (Mogram et al., 1985, Nature 315:338-40; Kollias et al., 1986, Cell 46:89-94); the myelin basic protein gene control region in oligodendrocyte cells in the brain (Readhead et al., 1987, Cell 48:703-12); the myosin light chain-2 gene control region in skeletal muscle (Sani, 1985, Nature 314:283-86); and the gonadotropic releasing hormone gene control region in the hypothalamus (Mason et al., 1986, Science 234:1372-78), and the tyrosinase promoter in melanoma cells (Hart, I. Semin Oncol 1996 February; 23(1):154-8; Siders, et al. Cancer Gene Ther 1998 September-October; 5(5):281-91). Other suitable promoters are known in the art.

The nucleic acid molecule may be administered as part of a viral and non-viral vector. In one embodiment, a DNA vector is utilized to deliver nucleic acids encoding the targeted immunogen and/or associated molecules (i.e., co-stimulatory molecules, cytokines or chemokines) to the patient. In doing so, various strategies may be utilized to improve the efficiency of such mechanisms including, for example, the use of self-replicating viral replicons (Caley, et al. 1999. Vaccine, 17: 3124-2135; Dubensky, et al. 2000. Mol. Med. 6: 723-732; Leitner, et al. 2000. Cancer Res. 60: 51-55), codon optimization (Liu, et al. 2000. Mol. Ther., 1: 497-500; Dubensky, supra; Huang, et al. 2001. J. Virol. 75: 4947-4951), in vivo electroporation (Widera, et al. 2000. J. Immunol. 164: 4635-3640), incorporation of nucleic acids encoding co-stimulatory molecules, cytokines and/or chemokines (Xiang, et al. 1995. Immunity, 2: 129-135; Kim, et al. 1998. Eur. J. Immunol., 28: 1089-1103; Iwasaki, et al. 1997. J. Immunol. 158: 4591-3601; Sheerlinck, et al. 2001. Vaccine, 19: 2647-2656), incorporation of stimulatory motifs such as CpG (Gurunathan, supra; Leitner, supra), sequences for targeting of the endocytic or ubiquitin-processing pathways (Thomson, et al. 1998. J. Virol. 72: 2246-2252; Velders, et al. 2001. J. Immunol. 166: 5366-5373), prime-boost regimens (Gurunathan, supra; Sullivan, et al. 2000. Nature, 408: 605-609; Hanke, et al. 1998. Vaccine, 16: 439-445; Amara, et al. 2001. Science, 292: 69-74), proteasome-sensitive cleavage sites, and the use of mucosal delivery vectors such as *Salmonella* (Darji, et al. 1997. Cell, 91: 765-775; Woo, et al. 2001. Vaccine, 19: 2945-2954). Other methods are known in the art, some of which are described below.

Various viral vectors that have been successfully utilized for introducing a nucleic acid to a host include retrovirus, adenovirus, adeno-associated virus (AAV), herpes virus, and poxvirus, among others. It is understood in the art that many such viral vectors are available in the art. The vectors may be constructed using standard recombinant techniques widely available to one skilled in the art. Such techniques may be found in common molecular biology references such as Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), and PCR Protocols: A Guide to Methods and Applications (Innis, et al. 1990. Academic Press, San Diego, Calif.).

Preferred retroviral vectors are derivatives of lentivirus as well as derivatives of murine or avian retroviruses. Examples of suitable retroviral vectors include, for example, Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of retroviral vectors can incorporate multiple exogenous nucleic acid sequences. As recombinant retroviruses are defective, they require assistance in order to produce infectious vector particles. This assistance can be provided by, for example, helper cell lines encoding retrovirus structural genes. Suitable helper cell lines include PA317 and PA12, among others. The vector virions produced using such cell lines may then be used to infect a tissue cell line, such as NIH 3T3 cells, to produce large quantities of chimeric retroviral virions. Retroviral vectors may be administered by traditional methods (i.e., injection) or by implantation of a "producer cell line" in proximity to the target cell population (Culver, K., et al., 1994, Hum. Gene Ther., 5 (3): 343-79; Culver, K., et al., Cold Spring Harb. Symp. Quant. Biol., 59: 685-90); Oldfield, E., 1993, Hum. Gene Ther., 4 (1): 39-69). The producer cell line is engineered to produce a viral vector and releases viral particles in the vicinity of the target cell. A portion of the released viral particles contact the target cells and infect those cells, thus delivering a nucleic acid to the target cell. Following infection of the target cell, expression of the nucleic acid of the vector occurs.

Adenoviral vectors have proven especially useful for gene transfer into eukaryotic cells (Rosenfeld, M., et al., 1991, Science, 252 (5004): 431-3; Crystal, R., et al., 1994, Nat. Genet., 8 (1): 42-51), the study of eukaryotic gene expression (Levrero, M., et al., 1991, Gene, 101 (2): 195-202), vaccine development (Graham, F. and Prevec, L., 1992, Biotechnology, 20: 363-90), and in animal models (Stratford-Perricaudet, L., et al., 1992, Bone Marrow Transplant., 9 (Suppl. 1): 151-2; Rich, D., et al., 1993, Hum. Gene Ther., 4 (4): 461-76). Experimental routes for administering recombinant Ad to different tissues in vivo have included intratracheal instillation (Rosenfeld, M., et al., 1992, Cell, 68 (1): 143-55) injection into muscle (Quantin, B., et al., 1992, Proc. Natl. Acad. Sci. U.S.A., 89 (7): 2581-3), peripheral intravenous injection (Herz, J., and Gerard, R., 1993, Proc. Natl. Acad. Sci. U.S.A., 90 (7): 2812-6) and stereotactic inoculation to brain (Le Gal La Salle, G., et al., 1993, Science, 259 (5097): 988-90), among others.

Adeno-associated virus (AAV) demonstrates high-level infectivity, broad host range and specificity in integrating into the host cell genome (Hermonat, P., et al., 1984, Proc. Natl. Acad. Sci. U.S.A., 81 (20): 6466-70). And Herpes Simplex Virus type-1 (HSV-1) is yet another attractive vector system, especially for use in the nervous system because of its neurotropic property (Geller, A., et al., 1991, Trends Neurosci., 14 (10): 428-32; Glorioso, et al., 1995, Mol. Biotechnol., 4 (1): 87-99; Glorioso, et al., 1995, Annu. Rev. Microbiol., 49: 675-710).

Poxvirus is another useful expression vector (Smith, et al. 1983, Gene, 25 (1): 21-8; Moss, et al, 1992, Biotechnology, 20: 345-62; Moss, et al, 1992, Curr. Top. Microbiol. Immunol., 158: 25-38; Moss, et al. 1991. Science, 252: 1662-1667). Poxviruses shown to be useful include vaccinia, NYVAC™, avipox, fowlpox, canarypox, ALVAC™, and ALVAC(2), among others.

NYVAC™ (vP866) was derived from the Copenhagen vaccine strain of vaccinia virus by deleting six nonessential regions of the genome encoding known or potential virulence factors (see, for example, U.S. Pat. Nos. 5,364,773 and 5,494,807). The deletion loci were also engineered as recipient loci for the insertion of foreign genes. The deleted regions are: thymidine kinase gene (TK; J2R) vP410; hemorrhagic region (u; B13R+B14R) vP553; A type inclusion body region (ATI; A26L) vP618; hemagglutinin gene (HA; A56R) vP723; host range gene region (C7L-K1L) vP804; and, large subunit, ribonucleotide reductase (14L) vP866. NYVAC™ is a genetically engineered vaccinia virus strain that was generated by the specific deletion of eighteen open reading frames encoding gene products associated with virulence and host range. NYVAC™ has been show to be useful for expressing TAs (see, for example, U.S. Pat. No. 6,265,189). NYVAC™ (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATCC-97913, ATCC-97912, and ATCC-97914, respectively.

ALVAC-based recombinant viruses (i.e., ALVAC-1 and ALVAC-2) are also suitable for use (see, for example, U.S. Pat. No. 5,756,103). ALVAC(2) is identical to ALVAC(1) except that ALVAC(2) genome comprises the vaccinia E3L and K3L genes under the control of vaccinia promoters (U.S.

Pat. No. 6,130,066; Beattie et al., 1995a, 1995b, 1991; Chang et al., 1992; Davies et al., 1993). Both ALVAC(1) and ALVAC (2) have been demonstrated to be useful in expressing foreign DNA sequences, such as TAs (Tartaglia et al., 1993 a,b; U.S. Pat. No. 5,833,975). ALVAC was deposited under the terms of the Budapest Treaty with the American Type Culture Collection (ATCC), 10801 University Boulevard, Manassas, Va. 20110-2209, USA, ATCC accession number VR-2547.

Another useful poxvirus vector is the TROVAC™ vector. TROVAC™ refers to an attenuated fowlpox that was a plaque-cloned isolate derived from the FP-1 vaccine strain of fowlpoxvirus which is licensed for vaccination of 1 day old chicks. A sample of the TROVAC™ vector was deposited under the terms of the Budapest Treaty with the ATCC, accession number 2553.

"Non-viral" plasmid vectors may also be suitable in certain embodiments. Preferred plasmid vectors are compatible with bacterial, insect, and/or mammalian host cells. Such vectors include, for example, PCR-II, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT pub. No. WO 90/14363) and pFastBacDual (Gibco-BRL, Grand Island, N.Y.) as well as Bluescript® plasmid derivatives (a high copy number COLE1-based phagemid, Stratagene Cloning Systems, La Jolla, Calif.), PCR cloning plasmids designed for cloning Taq-amplified PCR products (e.g., TOPO™ TA Cloning® kit, PCR2.1® plasmid derivatives, Invitrogen, Carlsbad, Calif.). Bacterial vectors may also be used. These vectors include, for example, *Shigella, Salmonella, Vibrio cholerae, Lactobacillus, Bacille calmette guérin* (BCG), and *Streptococcus* (see for example, WO 88/6626; WO 90/0594; WO 91/13157; WO 92/1796; and WO 92/21376). Many other non-viral plasmid expression vectors and systems are known in the art and may be used.

Other delivery techniques may also suffice including, for example, DNA-ligand complexes, adenovirus-ligand-DNA complexes, direct injection of DNA, CaPO4 precipitation, gene gun techniques, electroporation, and colloidal dispersion systems. Colloidal dispersion systems include macromolecule complexes, nanocapsules, microspheres, beads, and lipid-based systems including oil-in-water emulsions, micelles, mixed micelles, and liposomes. The preferred colloidal system is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, Trends Biochem. Sci., 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

*P. gingivalis* Polypeptide-Specific Antibodies

This disclosure further relates to antibodies, preferably protective and/or neutralizing antibodies, generated using one of PG0495, PG0654, PG1795, PG2172, PG0613, PG1326, PG1798, PG0186, or PG0616 or a fragment or variant thereof where the resultant antibodies are reactive to, or specifically bind to the *P. gingivalis* polypeptide and/or its fragments or variants. Also provided are methods for eliciting the production of antibodies, which may be protective, and/or neutralizing, and reactive to the *P. gingivalis* polypeptide and/or its fragments. The antibodies may elicit both active and passive immunity. The polypeptides and/or fragments thereof may also be used to identify and isolate antibodies, which may be protective and/or neutralizing, that are cross-reactive with those elicited by native *P. gingivalis* proteins.

Preferably, a purified antibody is separated from at least about 60%, 75%, 80%, 85%, 90%, or 95% of the proteins with which it is initially found. Suitable derivatives may include fragments (i.e., Fab, Fab2 or single chain antibodies such as Fv for example), as are known in the art. The antibodies may be of any suitable origin or form including, for example, murine (i.e., produced by murine hybridoma cells), or expressed as humanized antibodies, chimeric antibodies, human antibodies, and the like.

Methods of preparing and utilizing various types of antibodies are well-known to those of skill in the art and would be suitable for use (see, for example, Harlow, et al. Antibodies: A Laboratory Manual, Cold Spring Harbor Laboratory, 1988; Harlow, et al. Using Antibodies: A Laboratory Manual, Portable Protocol No. 1, 1998; Kohler and Milstein, Nature, 256:495 (1975)); Jones et al. Nature, 321:522-525 (1986); Riechmann et al. Nature, 332:323-329 (1988); Presta (Curr. Op. Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816, 567; 5,545,807; 5,545,806; 5,569,825; 5,625,126; 5,633,425; and, 5,661,016). In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques. The antibodies may be stored in any suitable format, including as a frozen preparation (i.e., −20° C.? or −70"C), in lyophilized form, or under normal refrigeration conditions (e.g., 4° C.). When stored in liquid form, it is preferred that a suitable buffer such as Tris-buffered saline (TBS) or phosphate buffered saline (PBS) is utilized. Antibodies and their derivatives may be incorporated into compositions described herein for use in vitro or in vivo. Other methods for making and using antibodies available to one of skill in the art may also be suitable for use.

Compositions

The disclosed polypeptides and the nucleic acids encoding these polypeptides are useful inter alia as components in immunogenic compositions (also referred to as immunological compositions) such as, for example, vaccine compositions. An immunogenic composition is one that, upon administration to a subject (e.g., a mammal), induces or enhances an immune response directed against the antigen (or immunogen) contained within the composition. This response may include the generation of antibodies (e.g., through the stimulation of B cells) or a T cell-based response (e.g., a cytolytic response). These responses may or may not be protective or neutralizing. A protective or neutralizing immune response is one that is detrimental to the infectious organism corresponding to the antigen (i.e., from which the antigen was derived) and beneficial to the host (e.g., by reducing or preventing infection). As used herein, protective or neutralizing antibodies may be reactive to the corresponding wild-type *P. gingivalis* antigen or fragments thereof from which the polypeptide (or fragments thereof) were derived and reduce or inhibit the lethality of the corresponding *P. gingivalis* antigen when tested in animals. An immunogenic composition that, upon administration to a subject, results in a protective or neutralizing immune response may be considered a vaccine. The vaccine composition may serve prophylactic and/or therapeutic purposes. Immunogenic compositions (e.g. vaccines) containing one or more of the *P. gingivalis* polypeptides (antigens) of the present invention may be used to treat and/or prevent periodontal diseases such as, for example, periodontitis and gingivitis. The immune response need not provide complete protection and/or treatment against the disease.

Preferred embodiments of the immunogenic compositions of the present invention include compositions comprising one or more of the following proteins: PG0495, PG0654, PG1374, PG1795, PG2172, PG0613, PG1326, PG1798, PG0186 and PG0616. A further preferred embodiment is an immunogenic composition comprising a polypeptide having at least 80%, 85%, 90%, 91%, 92%, 93%, 94%, 95%, 96%, 97%, 98%, 99% or 100% identity to SEQ ID NO:1, 3, 5, 7, 9, 11, 13, 15, 17, 19, 32, 34, 36, 38, 40, 42, 44, 46, 48, and 50.

Certain embodiments of the compositions of the present invention are described in Example 6. Preferred prophylactic compositions of the present invention are those which when administered to an animal elicit a Th2-antibody biased response; such a response has been associated with protection in the prophylactic alveolar bone loss mouse model (*J. Immunol.* 2008 Sep. 15; 181(6):4150-8).

Compositions (e.g., vaccine compositions) of the present invention may be administered in the presence of absence of an adjuvant. Adjuvants generally are substances that can enhance the immunogenicity of antigens. Adjuvants may play a role in both acquired and innate immunity and may function in a variety of ways, not all of which are understood.

Adjuvants may also be included in the compositions and methods described herein to stimulate or enhance the immune response. Non-limiting examples of suitable classes of adjuvants include those of the gel-type [e.g., aluminum hydroxide, aluminum phosphate ("aluminum adjuvants"), calcium phosphate, microbial origin (muramyl dipeptide (MDP)], bacterial exotoxins [e.g. cholera toxin (CT), native cholera toxin subunit B (CTB), *E. coli* labile toxin (LT), pertussis toxin (PT), CpG oligonucleotides, BCG sequences, tetanus toxoid, monophosphoryl lipid A (MPL) of for example, *E. coli, Salmonella minnesota, Salmonella typhimurium,* or *Shigella exseri*], particulate adjuvants (e.g. biodegradable, polymer microspheres), immunostimulatory complexes (IS-COMs)), oil-emulsion and surfactant-based adjuvants [Freund's incomplete adjuvant (FIA), microfluidized emulsions (e.g. MF59, SAF), saponins (e.g. QS-21)], synthetic muramyl peptide derivatives (murabutide, threony-MDP), nonionic block copolymers (e.g. L121), polyphosphazene (PCCP), synthetic polynucleotides (poly A:U, poly I:C), thalidomide derivatives (CC-4407/ACTIMID)), RH3-ligand, or polylactide glycolide (PLGA) microspheres, among others. Fragments, homologs, derivatives, and fusions to any of these described toxins are also suitable, provided that they retain adjuvant activity. Suitable mutants or variants of adjuvants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that may used include, for example, Ser-63-Lys, Ala-69-Gly, Glu-110-Asp, and Glu-112-Asp mutants.

Aluminum salt adjuvants (or compounds) are among the adjuvants of use in the practice of the invention. Examples of aluminum salt adjuvants of use include aluminum hydroxide (e.g., crystalline aluminum oxyhydroxide AlO(OH), and aluminum hydroxide $Al(OH)_3$. In particular embodiments, the aluminum adjuvant is aluminum oxyhydroxide (e.g., Alhydrogel®). It is well known in the art that compositions with aluminum salt adjuvants should not be exposed to extreme temperatures, i.e. below freezing (0° C.) or extreme heat (e.g., ≥70° C.) as such exposure may adversely affect the stability and the immunogenicity of both the adsorbed antigen and adjuvant.

Metallic salt adjuvants such as aluminum adjuvants are well-known in the art as providing a safe excipient with adjuvant activity. The mechanism of action of these adjuvants are thought to include the formation of an antigen depot such that antigen may stay at the site of injection for up to 3 weeks after administration, and also the formation of antigen/metallic salt complexes which are more easily taken up by antigen presenting cells. In addition to aluminium, other metallic salts have been used to adsorb antigens, including salts of zinc, calcium, cerium, chromium, iron, and berilium. The hydroxide and phosphate salts of aluminium are the most common. Formulations or compositions containing aluminium salts, antigen, and an additional immunostimulant are known in the art. An example of an immunostimulant is 3-de-O-acylated monophosphoryl lipid A (3D-MPL). Another example is the product E6020 (having CAS Number 287180-63-6). In certain embodiments, the composition includes aluminum hydroxide and E6020. Product E6020 is described in US2007/0082875 (which is incorporated herein by reference in its entirety).

In one embodiment of adjuvanted immunization, for example, polypeptides and/or fragments thereof may be covalently coupled to bacterial polysaccharides to form polysaccharide conjugates. Such conjugates may be useful as immunogens for eliciting a T cell dependent immunogenic response directed against the bacterial polysaccharide conjugated to the polypeptides and/or fragments thereof.

One or more cytokines may also be suitable co-stimulatory components for use with the compositions of the present invention, either as polypeptides or as encoded by nucleic acids (Parmiani, et al. Immunol Lett 2000 Sep. 15; 74(1): 41-3; Berzofsky, et al. Nature Immunol. 1: 209-219). Suitable cytokines include, for example, interleukin-2 (IL-2) (Rosenberg, et al. Nature Med. 4: 321-327 (1998)), IL-4, IL-7, IL-12 (reviewed by Pardoll, 1992; Harries, et al. J. Gene Med. 2000 July-August; 2(4):243-9; Rao, et al. J. Immunol. 156: 3357-3365 (1996)), IL-15 (Xin, et al. Vaccine, 17:858-866, 1999), IL-16 (Cruikshank, et al. J. Leuk Biol. 67(6): 757-66, 2000), IL-18 (J. Cancer Res. Clin. Oncol. 2001. 127(12): 718-726), GM-CSF ((Disis, et al. Blood, 88: 202-210 (1996)), tumor necrosis factor-alpha (TNF-α), and interferon-gamma (INF-γ). Other cytokines may also be suitable for use, as is known in the art.

In certain embodiments, the composition is administered in the presence of an adjuvant that comprises an oil-in-water emulsion comprising at least squalene, an aqueous solvent, a polyoxyethylene alkyl ether hydrophilic nonionic surfactant, a hydrophobic nonionic surfactant, wherein said oil-in-water emulsion is obtainable by a phase inversion temperature process and wherein 90% of the population by volume of the oil drops has a size less than 200 nm, and optionally less than 150 nm. Such an adjuvant is described in WO2007006939 (Vaccine Composition Comprising a Thermoinversable Emulsion) which is incorporate herein in its entirety. The composition may also include the product E6020 (having CAS Number 287180-63-6), in addition to, or instead of the described squalene oil-in-water emulsion.

In certain embodiments, the composition includes a TLR agonist (e.g., TLR4 agonist) alone or together in combination with an adjuvant. For example, the adjuvant may comprise a TLR4 agonist (e.g., TLA4), squalene, an aqueous solvent, a nonionic hydrophilic surfactant belonging to the polyoxyethylene alkyl ether chemical group, and a nonionic hydrophobic surfactant and may be thermoreversible. Examples of such adjuvants are described in WO2007080308 (Thermoreversible Oil-in-Water Emulsion) which is incorporated herein in its entirety. In one embodiment, the composition is adjuvanted with a combination of CpG and an aluminum salt adjuvant (e.g., aluminum hydroxide).

Pharmaceutical Formulations

The compositions of the present invention are preferably in liquid form, but they may be lyophilized (as per standard methods) or foam dried (as described in WO2009012601, Antigen-Adjuvant Compositions and Methods). A composition according to one embodiment of the invention is in a liquid form. An immunization dose may be formulated in a volume of between 0.5 and 1.0 ml. Liquid formulations may be in any form suitable for administration including for example, a solution, or suspension.

The pharmaceutical formulations of the compositions of the present invention may also optionally include a "pharmaceutically acceptable carrier." The term "pharmaceutically acceptable carrier" refers to a material that is not biologically or otherwise undesirable, (i.e., the material may be administered to a subject, without causing any undesirable biological effects or interacting in a deleterious manner with any of the other components of the pharmaceutical composition in which it is contained). The carrier would naturally be selected to minimize any degradation of the active ingredient (e.g., immunogenic polypeptide) and to minimize any adverse side effects in the subject, as would be well known to one of skill in the art.

Suitable carriers and their formulations are described in Remington: The Science and Practice of Pharmacy, 21st Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained-release preparations such as semipermeable matrices of solid hydrophobic polymers containing polypeptides or fragments thereof. Matrices may be in the form of shaped articles, e.g., films, liposomes or microparticles. It will be apparent to those persons skilled in the art that certain carriers may be more preferable depending upon, for instance, the route of administration and concentration of composition being administered. Carriers are those suitable for administration of polypeptides and/or fragments thereof to humans or other subjects.

The pharmaceutical formulations of the compositions of the present invention may also optionally include one or more excipients (e.g., diluents, thickeners, buffers, preservatives, surface active agents, detergents, and/or immunostimulants) which are well known in the art. Suitable excipients will be compatible with the antigen and with any adjuvant present in the composition as is well known in the art. Examples of diluents include binder, disintegrants, or dispersants such as starch, cellulose derivatives, phenol, polyethylene glycol, propylene glycol or glycerin. Examples of detergents include a Tween (polysorbate) such as Tween 80. Pharmaceutical compositions may also include one or more active ingredients such as antimicrobial agents, antiinflammatory agents and anesthetics. Suitable excipients for inclusion in the compositions of the invention are known in the art.

The compositions may be formulated for use orally such as, for example, but not limited to, as a toothpaste, toothpowder, liquid dentrifice, gingival cream, gel, capsule, lozenge and chewing gum.

Compositions may be presented in a kit form comprising the composition and instructions for use. In one example, the composition is presented in a kit comprising the composition and an adjuvant or a reconstitution solution comprising one or more pharmaceutically acceptable diluents to facilitate reconstitution of the composition for administration to a mammal using conventional or other devices. Such a kit may optionally include the device for administration of the liquid form of the composition (e.g. hypodermic syringe, microneedle array) and/or instructions for use.

Method of Use

The prophylactic and therapeutic methods of the invention involve vaccination with one or more of the disclosed immunogenic polypeptides in, for example, carrying out the treatment itself, in preventing subsequent infection, or in the production of antibodies for subsequent use in passive immunization.

The immunogenic compositions of the invention find use in methods of preventing or treating a disease, disorder, condition or symptoms associated with *P. gingivalis*. The terms disease, disorder and condition will be used interchangeably herein. Specifically, the prophylactic and therapeutic methods comprise administration of a therapeutically effective amount of a pharmaceutical composition to a subject. In particular embodiments, methods for preventing or treating periodontal disease associated with a symptomatic *P. gingivalis* infection are provided.

As used herein, preventing a disease or disorder is intended to mean administration of a therapeutically effective amount of a pharmaceutical composition of the invention to a subject in order to protect the subject from the development of the particular disease or disorder associated with *P. gingivalis*.

By treating a disease or disorder is intended administration of a therapeutically effective amount of a pharmaceutical composition of the invention to a subject that is afflicted with a disease caused by *P. gingivalis* or that has been exposed to *P. gingivalis* where the purpose is to cure, heal alleviate, relieve, alter, remedy, ameliorate, improve, or affect the condition or the symptoms of the disease.

A therapeutically effective amount refers to an amount that provides a therapeutic effect for a given condition and administration regimen. A therapeutically effective amount can be determined by the ordinary skilled medical worker based on patient characteristics (age, weight, gender, condition, complications other diseases etc.). The therapeutically effective amount will be further influenced by the route of administration of the composition.

Compositions of the invention can be administered by an appropriate route such as for example, percutaneous (e.g., intramuscular, intravenous, intraperitoneal or subcutaneous), transdermal, mucosal or topical, in amounts and in regimes determined to be appropriate by those skilled in the art.

The methods include administering to a subject an effective amount of a composition of the present invention. In some aspects, the methods may further include additional administration (e.g., one or more booster administrations) of the compositions to the subject to enhance or stimulate a secondary immune response. A booster can be administered at a time after the first administration, for instance, one to eight weeks, preferably two to four weeks, after the first administration of the composition. Subsequently boosters can be administrated one, two, three four or more times annually. Without intending to be limited by theory, it is expected that in some aspects of the present invention annual boosters will not be necessary, as a subject will be challenged in the field by exposure to microbes (P. gingivalis) expressing polypeptides present in the compositions and having epitopes that are identical to, or structurally related to, epitopes present on polypeptides of the composition administered to the subject.

In one aspect, the invention is directed to methods for making antibodies, for instance by inducing the production of the antibody in a subject, or by recombinant techniques. The antibody produced includes antibody that specifically binds at least one epitope of at least one polypeptide present in the composition. In this aspect of the invention, an "effective amount" is an amount effective to result in the production of antibody in the subject. Methods determining whether a subject has produced antibodies that specifically bind polypeptides present in a composition of the present invention are well known in the art and can be determined as described herein. The present invention further includes antibody that specifically bind to a polypeptide of the present invention, and compositions including such antibodies.

The method may be used to produce antibody that specifically binds polypeptides expressed by a microbe (P. gingivalis) from which the polypeptide of the composition were isolated. As used herein, an antibody that can "specifically bind" a polypeptide is an antibody that interacts with the epitope of the antigen that induced the synthesis of the antibody, or interacts with a structurally related epitope. At least some of the polypeptides present in the compositions of the present invention typically include epitopes that are conserved in the polypeptides of different strain species. Accordingly, antibody produced using a composition derived from one strain of P. gingivalis is expected to bind to the polypeptides expressed by other P. gingivalis strains and provide broad system protection against this gram negative organism.

Also disclosed, is a method of reducing the risk of a periodontal disease in a subject comprising administering to the subject an immunogenic composition comprising one or more of the disclosed immunogenic polypeptides. Periodontal diseases (symptomatic infections) include for example, periodontitis. The risk of any symptomatic P. gingivalis infection (or the recurrence of any such symptomatic P. gingivalis infection) may be reduced by the methods described herein.
Diagnosis Kits Also, provided herein are kits for detecting the presence of a P. gingivalis infection in a patient by detecting antibodies or nucleic acid in a biological sample of the patient. In one embodiment, one or more antigens (e.g., polypeptides and/or fragment thereof) may form part of a kit for detecting or diagnosing anti-P. gingivalis antibodies in a biological sample. The antigens may be provided in a suitable container such as a vial in which the contents are protected from the external environment. Thus, a kit for detecting an anti-P. gingivalis antibody in a sample may comprise one or more P. gingivalis polypeptides and/or fragments thereof along with one or more detection reagents for determining binding of one or more antibodies in a sample to the antigen is provided. The kit preferably includes: (i) one or more isolated and purified polypeptides and/or fragments thereof; and, (ii) a system for detecting the formation of an antigen-antibody complex, optionally packaged with instructions for use. The antigen may be free in solution or may be immobilized on a solid support, such as a magnetic bead, tube, microplate well, or chip. In certain embodiments, a solid matrix comprising an isolated and purified polypeptides and/or fragments thereof or a fusion protein or protein aggregate adsorbed thereto is provided. In some embodiments, the kit may further comprise an antibody-binding molecule as a detection reagent. The antibody-binding molecule may be a capture or detection reagent and may be free in solution or may be immobilized on a solid support, such as a magnetic bead, tube, microplate well, or chip. The antibody-binding molecule or polypeptide may be labeled with a detectable label, for example a fluorescent or chromogenic label or a binding moiety such as biotin. Suitable labels are described in more detail above. The kit may further comprise detection reagents such as a substrate, for example a chromogenic, fluorescent or chemiluminescent substrate, which reacts with the label, or with molecules, such as enzyme conjugates, which bind to the label, to produce a signal, and/or reagents for immunoprecipitation). The detection reagents may further comprise buffer solutions, wash solutions, and other useful reagents. The kit may also comprise one or both of an apparatus for handling and/or storing the sample obtained from the subject and an apparatus for obtaining the sample from the subject (e.g. a needle, lancet, and collection tube or vessel). The kit may also include instructions for use of the antigen, (e.g. in a method of detecting anti-P. gingivalis antibodies in a test sample), as described herein. Where the assay is to be combined with another type of assay such as PCR, the required reagents for such an assay (i.e., primers, buffers and the like) along with, optionally, instructions for the use thereof, may also be included.

All references cited within this disclosure are hereby incorporated by reference in their entirety. Certain embodiments are further described in the following examples. These embodiments are provided as examples only and are not intended to limit the scope of the claims in any way.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Methods of molecular genetics, protein biochemistry, and immunology used, but not explicitly described in this disclosure and these Examples, are amply reported in the scientific literatures and are well within the ability of those skilled in the art.

Example 1

Mining of P. gingivalis Genome

This example describes the genome mining exercise that was conducted to identify immunogenic polypeptides of P.

gingivalis. The genome of *P. gingivalis* strain W83 has approximately 2200 open reading frames. Using computer-assistance, the proteins comprising the *P. gingivalis* W83 genome (http://cmr.jcvi.org/cgi-bin/CMR/GenomePage.cgi?org=gpg) were each assessed using the following parameters to prioritize those proteins for further evaluation (by cloning, expression and purification):

1. Candidates with a C-terminal domain (CTD) were prioritized for further evaluation. The presence of the CTD has been shown in the *P. gingivalis* proteinase, RgpB, to be required for its proper maturation, correct secretion and attachment to the cell surface (Nguyen et al., J. of Bacteriology, 2007, 189, 833-843).

2. PSORTb localization, from high to low priority: (outer membrane or extracellular)>(unknown)>(periplasmic or cytoplasmic). Psortb (version 2.0) is a web-based bacterial protein subcellular localization prediction tool [available at www.psort.org; J. L. Gardy, M. R. Laird, F. Chen, S. Rey, C. J. Walsh, M. Ester, and F. S. L. Brinkman (2005) PSORTb v.2.0: expanded prediction of bacterial protein subcellular localization and insights gained from comparative proteome analysis, Bioinformatics 21(5):617-623]

3. Other parameters favouring a higher priority to be applied to the protein:
   i. the presence of a signal sequence;
   ii. strain prevalence (i.e. presence in *P. gingivalis* strains W50, W83 and strain ATCC 33277);
   iii. high (75%) sequence conservation among strains with a published sequenced genome (e.g. W83, ATCC 33277);
   iv. published articles disclosing data indicating the protein is localized in the outer membrane, and/or is a potential virulence factor;

4. Other parameters favouring a lower priority to be applied to the protein:
   i. detectable human sequence similarity;
   ii. predicted transmembrane helices;
   iii. molecular weight>100 kDa or <20 kDa
   iv. predicted subcellular localization Using these prioritization parameters, approximately 131 protein candidates were identified for evaluation. Each of the candidates were then cloned from *P. gingivalis* strain W50 (deposited as ATCC 53978) and expressed recombinantly in *Escherichia coli*, as explained in more detail in Example 2. Those which were expressed solubly (i.e. approximately 40 proteins), were selected for further evaluation.

Example 2

Recombinant Cloning, Expression and Purification of *P. gingivalis* Proteins

Selected genes from *Polymorphomonas gingivalis* strain W50 (e.g. PG 0495, PG 2172, PG 1326, PG 1374, PG 0654, PG 0613, PG 1798, PG 0186, PG 1795, PG 0616) were recombinantly cloned, expressed and purified.

The primers set out in Table 4 below were designed to amplify the relevant gene (full-length but lacking signal sequence) from *P. gingivalis* W50 strain. The amplified gene products were cloned into pET-30 Ek/LIC (Novagen®, Merck, Germany) with the ET-30 Ek/LIC Vector Kit. Using this vector the expressed product has a vector-encoded S-tag to facilitate expression analysis and a vector encoded N-terminal tag (mhhhhhhssglvprgsgmketaaakferqhmdspdlgtddddk SEQ ID NO:51). Based on the cloning requirements for the vector, the next amino acid must be either a Met (m) or an Ile (i), so either of those residues was also added in cases where it was not the first native amino acid of the desired fragment to be cloned. Digestion with enterokinase enables the removal of all vector-encoded sequences from the target protein, but for initial screening purposes, the tags were not removed.

The signal peptide sequences for each of the genes were predicted using SignalIP (http://www.cbs.dtu.dk/services/SignalP/) or were assigned based upon the typical *P. gingivalis* type I signal cleavage site consensus as previously described and identified (J. Bacteriol. 2006 September: 188 (17):6376-6386). The genes were cloned such that the resulting cloned nucleotide sequence lacked the signal peptide sequence. Signal peptide sequences can be predicted in a number of ways as is known in the art, including through the use of prediction software such as that available at http://www.cbs.dtu.dk/services/SignalP/ (Locating proteins in the cell using TargetP, SignalP, and related tools, O. Emanuelsson, S. Brunak, G. von Heijne, H. Nielsen, *Nature Protocols* 2, 953-971 (2007)).

The resulting vectors were each subcloned into the NovaBlue competent cells and subsequently the resulting plasmids were each transformed into *E. coli* strain BL21 (DE3) for protein production using Overnight Express™ Autoinduction System 1 (Novagen). Upon IPTG induction the recombinant polypeptides were expressed.

Following expression, the solubility of the expressed polypeptides were assessed using SDS-PAGE and/or the FRETWorks™ S-TagT™ assay kit (Novagen, according to manufacturer's recommendations). The basis for this assay is that the S-tag fusion peptide from any soluble recombinant protein is able to provide trans-complementation to the exogenously added purified mutant version of the S protein to restore RNase activity. The substrate FRET ArUAA fluoresces when cleaved by the reconstituted RNase and provides a fluorescence readout.

Solubly expressed polypeptides were purified by affinity chromatography using $Ni^{2+}$-NTA agarose under native conditions using a commercially available kit (Qiagen®). Subsequent SDS-PAGE analysis with Commassie Blue staining was performed in respect of each recombinanity cloned polypeptide and in each case a single band was noted with the approximate molecular weight noted in Table 3 below.

TABLE 3

| Recombinant Polypeptide | Plasmid | MW (single band in gel) |
| --- | --- | --- |
| rPG 0495 | pEAG001 | 56 |
| rPG 2172 | pEAG023 | 29 |
| rPG 1326 | pEAG053 | 44 |
| rPG 1374 | pEAG019 | 50 |
| rPG 0654 | pEAG018 | 48 |
| rPG 0613 | pEAG034 | 28 |
| rPG 1798 | pEAG 021 | 55 |
| rPG 0186 | pEAG 037 | 59 |
| rPG 1795 | pEAG 024 | 32 |
| rPG 0616 | pEAG 005 | 40 |

TABLE 4

PCR Primers

| Gene | # nucl (bp) | Signal sequence | Forward Primer (based on W83 sequence) | Reverse Primer (based on W83 sequence) |
|---|---|---|---|---|
| rPG0186 | 1503 | MKKIIYWVAT VFLAASVSS (SEQ ID NO: 52) | GACGACGACAAGATGTGC GAGCTTGACCGCGACCC (SEQ ID NO: 60) | GAGGAGAAGCCCGGTTATATC GGCCAGTTCTTTATTAACTGC GGATTAG (SEQ ID NO: 61) |
| rPG0495 | 1410 | MRKIIMKKLFL ASVAFLCAWI WSANA (SEQ ID NO: 53) | GACGACGACAAGATGCAG ACAATGGCTCCAAATTACT TCC (SEQ ID NO: 62) | GAGGAGAAGCCCGGTTATTG AACGATCACTCTTTCTGTAAT ATCAC (SEQ ID NO: 63) |
| rPG0613 | 687 | MMKKAFVFVL LVCLFSSFSSSA (SEQ ID NO: 54) | GACGACGACAAGATGCAA ACAACGACGAACAGTAGC C (SEQ ID NO: 64) | GAGGAGAAGCCCGGTCATTTT TGTTGTGATACTGTTTGGG (SEQ ID NO: 65) |
| rPG0654 | 1170 | MKRLLPFLLLA GLVAVGNVSA (SEQ ID NO: 55) | GACGACGACAAGATGCAG TCACCCCGAATCCCTCAAG (SEQ ID NO: 66) | GAGGAGAAGCCCGGTTATCTG AGCGATACTTTTGCACGTATG (SEQ ID NO: 67) |
| rPG1326 | 1056 | No | GACGACGACAAGATGTTG TGTGAAAATACCCTTGCAC AAC (SEQ ID NO: 68) | GAGGAGAAGCCCGGTTATTG GATTTGGATTTTCTCAGTATA GACAG (SEQ ID NO: 69) |
| rPG1374 | 1284 | MKLSSKKILAII ALLTMGHAVQ A (SEQ ID NO: 56) | GACGACGACAAGATGCAG TTTGTTCCGGCTCCCAC (SEQ ID NO: 70) | GAGGAGAAGCCCGGTTACTGT TTGATGAGCTTAGTGGTATAG TTATC (SEQ ID NO: 71) |
| rPG1795 | 819 | MKKALLIGAAL LGAVSFASA (SEQ ID NO: 57) | GACGACGACAAGATGCAG TCTTTGAGCACAATCAAAG TACAG (SEQ ID NO: 72) | GAGGAGAAGCCCGGTTAGAT AGCCAGCTTGATGCTC (SEQ ID NO: 73) |
| rPG1798 | 1215 | MKKTTIISLIVF GAFFAAVG (SEQ ID NO: 58) | GACGACGACAAGATGCAA ACCAAGGACAATTCTTCTT ACAAAC (SEQ ID NO: 74) | GAGGAGAAGCCCGGTCATCG AATCACGACTTTTCTCAC (SEQ ID NO: 75) |
| rPG2172 | 744 | MNKKTKRNMR KIFISIALLAGFI AALNA (SEQ ID NO: 59) | GACGACGACAAGATGCAA GTTGTGATCAAGGTGGGA G (SEQ ID NO: 76) | GAGGAGAAGCCCGGTTACTTA ATCAGATACTTCTGAACAAAC G (SEQ ID NO: 77) |

A person skilled in the art will appreciate that the nucleotide sequences could be cloned with the signal peptide sequence. Similarly, a person skilled in the art will appreciate that the polypeptides can each be recombinantly expressed without the vector encoded S-tag and His-tag by using a different plasmid cloning vector. It should be noted however that with respect to PG 0616, the polypeptide is capable of being expressed solubly by cloning the gene, without the signal peptide sequence into the pET-30 Ek/LIC whereas the polypeptide was not soluble when expressed with the signal peptide.

rPG0495

The gene was cloned from the W50 strain as described above. Plasmid DNA was isolated and sequenced (sequence set out as SEQ ID NO:41). The sequence of the expressed protein is set out as SEQ ID NO:21. The nucleotide sequence of the cloned gene (set out as SEQ ID NO:22) is identical to that of W83 apart from the following changes:
i) by 130 is a "T" in the cloned gene, whereas it is an "A" in the published W83 sequence. This results in a MET to LEU substitution at this codon.
ii) by 861 is a "G" in the cloned gene, whereas it is an "A" in the published W83 sequence. This is a silent mutation as both GCG and GCA encode alanine.
iii) There is an "A" missing after by 1440 which results in a frame shift with the following consequences: the C-terminal 7 amino acids should be TERVIVQ* (SEQ ID NO: 78), whereas in the protein encoded by the cloned gene these are replaced by QKE*. This frame shift is a cloning artifact. Below is the amino acid sequence of the rPG0495 protein that has been cloned and expressed (vector derived sequence is underlined).

(SEQ ID NO: 21)
<u>MHHHHHHSSGLVPRGSGMKETAAAKFERQHMDSPDLGTDDDDKL</u>QTMAPN

YFHADPQQFKHRIVKEKSFSSYSNYEYGVDNRLQRIYSVDESSGEIEHER

RFFFNEGGYMIREEEYDGTVQIPVRKWEFVRDDKGYITHFSRYSPKDGSQ

ELIEDIRIDFSYDADMKLIKADIDFFDIMANVWGDLRTTKLVYNENGLLK

EMIQTDPGSGQEFNREELTYNNLNKIVAIRFIPGPASTGLNEFELIYEYD

SEGMDIVKAGRDDEWYYYEYDKEMLASETFFPKPSIADLVYFGLKDYVDF

SGLPFKNSYTHVVVKESTNEVEAIYEPISVYSVVVIQPENGEIKLTADGQ

PLNSGSTLVAGRRIKIHPIPAEGYEVDKVMVNGENIEAPYEFLLEKDTEV

TALMKKSNAVGEVDTKGFHVYPIPTSKDLTIEIPAEMVGKVASLIDMNGQ

IVYRVTLNNIFQQIDISHLKGVFLLQIGDIQKE rPG2172

The gene was cloned from the W50 strain as described above. Plasmid DNA was isolated and sequenced (sequence set out as SEQ ID NO:47). The sequence of the expressed protein is set out as SEQ ID NO:29. The nucleotide sequence of the W50 cloned gene (set out in SEQ ID NO:30) is identical to the corresponding W83 sequence from the published genome. Below is the amino acid sequence of the rPG2172 protein that has been cloned and expressed (vector derived sequence is underlined).

(SEQ ID NO: 29)
MHHHHHHSSGLVPRGSGMKETAAAKFERQHMDSPDLGTDDDDKMQVVIKV

GDAILENNATVDITAFTTEDGTEEMKFEGMVINQSATPINVIGKITKQEM

IGDGHFALCFGQCMGPNVSVSPIVEALDGEGEYVSLHYKFPVSNEGHTGA

FTFSCFPESGAPGTELATVNINFKYKGGGTGLTNIGLGRIALIQSGNTCT

LQYNSNGKRLALEVYNLLGVKVFTSQLPAGSGSYTLPVRLQRGVHIFRIT

EGGKPAFVQKYLIK rPG1326
The gene was cloned from the W50 strain as described above. The sequence of the expressed protein is set out as SEQ ID NO:39. The sequence of the W50 cloned gene (set out as SEQ ID NO:40) is identical to the corresponding W83 sequence from the published genome. Below is the amino acid sequence of the rPG1326 protein that has been cloned and expressed (vector derived sequence is underlined).

(SEQ ID NO: 39)
MHHHHHHSSGLVPRGSGMKETAAAKFERQHMDSPDLGTDDDDKMLCENTL

AQQKTEEFAPVSDLRAEAYGSTVFLHWTPPYDNPMIPLSESFESGIPAIW

KTIDADGDGYNWMHLTNFTGQSGLCVSSASYIGGVGALTPDNYLITPELK

LPTDALVEIIYWVCTQDLTAPSEHYAVYSSSTGNNAADFVNLLYEETLTA

KRIQSPELIRGNRTQGVWYQRKVVLPNDTKYVAFRHFNSTDNFWLNLDEV

SILYTPLPRRAPCPHPGGYTYSVFRDGQKIASGLSALAYIDTDVPYGTQD

YCVQVNYLQGDSYKVCKNIVVANSANIYGADKPFALTVVGKTIVASAFKG

EITLYDIRGRLIASGCDTLRYKAENGFYLIKIQVNGTVYTEKIQIQ rPG0654
The gene was cloned from the W50 strain. Plasmid DNA was isolated and sequenced (sequence set out as SEQ ID NO:43). The sequence of the expressed protein is set out as SEQ ID NO:25. The sequence of the W50 cloned gene (set out as SEQ ID NO:26) is identical to the corresponding W83 sequence from the published genome. Below is the amino acid sequence of the rPG0654 protein that has been cloned and expressed (vector derived sequence is underlined).

(SEQ ID NO: 25)
MHHHHHHSSGLVPRGSGMKETAAAKFERQHMDSPDLGTDDDDKMQSPRIP

QVDVHTRIARNARYRLDKISVPDSRQIFDYFYKEETIPTKIQTTTGGAIT

SIDSLFYEDDRLVQVRYFDNNLELKQAEKYVYDGSKLVLREIRKSPTDET

PIKKVSYHYLCGSDMPFEITTEMSDGYFESHTLNYLNGKIARIDIMTQQN

PSAELIETGRMVYEFDANNDAVLLRDSVFLPLQNKWVEMFTHRYTYDNKH

NCIRWEQDEFGTLTLANNFEYDTTIPLSSVLFPTHEEFFRPLLPNFMKHM

RTKQTYFNNSGEGLSEVCDYNYFYTDMQGNALTDVAVNESIKIYPRPATD

FLRIEGSQLLRLSLEDMNGKLIRATELTGDLAIIGVASLPRGTYIAEITA

ANSKTIRAKVSLR rPG1374
The gene was cloned from the W50 strain. Plasmid DNA was isolated and sequenced (sequence set out as SEQ ID NO:44). The sequence of the expressed protein is set out as SEQ ID NO:27. The sequence of the cloned gene (set out as SEQ ID NO:28) is identical to the corresponding sequence of W83 apart from as follows:

i) bp 481 is a "T" in the cloned gene, whereas it is a "C", in the published W83 sequence. This is a silent mutation, as both CTG and TTG encode LEU (i.e. the proteins are 100% identical).

Below is the amino acid sequence of the rPG1374 protein that has been cloned and expressed (vector derived sequence is underlined).

(SEQ ID NO: 27)
MHHHHHHSSGLVPRGSGMKETAAAKFERQHMDSPDLGTDDDDKMQFVPAP

TTGIRMSVTTTKAVGEKIELLVHSIEKKGIWIDLNGDATYQQGEEITVFD

EAYHEYTIGTQTLTIYGNTTRLGCRSTGATAVDVTKNPNLTYLACPKNNL

KSLDLTQNPKLLRVWCDSNEIESLDLSGNPALIILGCDRNKLTELKTDNN

PKLASLWCSDNNLTELELSANPRLNDLWCFGNRITKLDLSANPLLVTLWC

SDNELSTLDLSKNSDVAYLWCSSNKLTSLNLSGVKGLSVLVCHSNQIAGE

EMTKVVNALPTLSPGAGAQSKFVVVDLKDTDEKNICTVKDVEKAKSKNWR

VFDFNGDSDNMLPYEGSPTSNLAVDAPTVRIYPNPVGRYALVEIPESLLG

QEAALYDMNGVKVYSFAVESLRQNIDLTHLPDGTYFFRLDNYTTKLIKQ rPG1795
The gene was cloned from the W50 strain. Plasmid DNA was isolated and sequenced (sequence set out as SEQ ID NO:48). The sequence of the expressed protein is set out as SEQ ID NO:31. The sequence of the W50 cloned gene (set out as SEQ ID NO:32) is identical to the W83 sequence from the published genome.

Below is the amino acid sequence of the rPG1795 protein that has been cloned and expressed (vector derived sequence is underlined).

(SEQ ID NO: 31)
MHHHHHHSSGLVPRGSGMKETAAAKFERQHMDSPDLGTDDDDKMQSLSTI

KVQNNSVQQPREEATIQVCGELAEQVDCIGTGNSAIIAAAAKFESDDLES

YVGWEIMSVDFFPGYKACKYTSAVWADDMTILGQSEDSDPEMQTINNLAL

KTSVKIEAGKNYIVGYIANTAGGHPIGCDQGPAVDGYGDLVSISEDGGAT

FPPPFESLHQAVPTLNYNIYVVVHLKKGEGVEAVLTNDKANAYVQNGVIYV

AGANGRQVSLFDMNGKVVYTGVSETIAAPQKGMYILRVGAKSIKLAI rPG0613
The gene was cloned from the W50 strain as described above. Plasmid DNA was isolated and sequenced (sequence set out as SEQ ID NO:49). The sequence of the expressed protein is set out as SEQ ID NO:33. The sequence of the W50 cloned gene (set out as SEQ ID NO:34) is identical to the W83 sequence from the published genome.

Below is the amino acid sequence of the rPG0613 protein that has been cloned and expressed (vector derived sequence is underlined).

(SEQ ID NO: 33)
MHHHHHHSSGLVPRGSGMKETAAAKFERQHMDSPDLGTDDDDKMQTTTNS

SRSYFTGRIEKVSLNLGVPPVSTEVWGMTHDANGLPFEIPISFSRFNSQG

DIATTYYIANSEATLNEWCDYAHPGGIVRVEGRFWKMTYNIPTYNAVCTR

ITFENQEIEGTIVLIPKPKVSLPHVSESVPCIRTEAGREFILCEEDDTFV

SHDGNEVTIGGKPFLLNTNVKIVGDVSQKYAVGVGEIRFLQICAQTVSQQ

K rPG1798
The gene was cloned from the W50 strain as described above. Plasmid DNA was isolated and sequenced (sequence set out as SEQ ID NO:46). The sequence of the expressed protein is set out as SEQ ID NO:35. The sequence of the cloned gene (set out as SEQ ID NO:36) is identical to that of W83 apart from the following changes:
i) An error was introduced at the 3' end of the gene during PCR amplification (in the primer). The net result is that the protein expressed is missing its last 2 native amino acids and an additional ~56 amino acids have been added (encoded from the vector). The predicted correct sequence of the plasmid is set out as SEQ ID NO:45.
Below is the amino acid sequence of the rPG1798 protein that has been cloned and expressed (vector derived sequence is underlined).

(SEQ ID NO: 35)
MHHHHHHSSGLVPRGSGMKETAAAKFERQHMDSPDLGTDDDDKMQTKDNS

SYKPFSKEDIAGGVYSLPTQNRAQKDNAEWLLTATVSTNQSADTHFIFDE

NNRYIARDIKANGVRKSTDSIYYDANGRISHVDLYISFSGGEPALDTRFK

YTYDDEGKMTVREVFMLVMDPNTPISRLEYHYDAQGRLTHWISFAFGAES

QKNTYHYNEKGLLVSEVLSNAMGTTYSDTGKTEYSYDDADNMVKAEYFVV

QQGKAWQVLKREEYTYEDNICIQYLAINGTDTKVYKRDIESDKSISANVI

DIPSMPEQTWPNMYGFNAKRLKETYSSYEGDVATPIFDYIYTYKALTSMA

TPSTEAQVAVYLNPSTDRLVILANGITHLSMYDLQGKLIRDCALSGDKVE

MGVGSLTKGTYLLKVNTDQGAFVRKVVFDDRASPQPWRYRIRIRAPSTSL

RPHSSTTTTTEIRLLTKPERKLSWLLPPLSNN rPG0186
The gene was cloned from the W50 strain as described above. Plasmid DNA was isolated and sequenced (sequence set out as SEQ ID NO:50). The sequence of the expressed protein is set out as SEQ ID NO:37. The sequence of the insert of the plasmid pEAG037 (the cloned gene; set out as SEQ ID NO: 38) was 100% correct as predicted from the W83 sequence.
Below is the amino acid sequence of the rPG0186 protein that has been cloned and expressed (vector derived sequence is underlined).

(SEQ ID NO: 37)
MHHHHHHSSGLVPRGSGMKETAAAKFERQHMDSPDLGTDDDDKMCELDRD

PEGKDFQQPYTSFVQTKQNRDGLYALLRNTENPRMHFYQELQSDMYCTTI

TDGNSLAPFVNWDLGILNDHGRADEDEVSGIAGYYFVYNRLNQQANAFVN

NTEAALQNQVYKNSTEIANAKSFLAEGKVLQALAIWRLMDRFSFHESVTE

VNSGAKDLGVILLKEYNPGYIGPRATKAQCYDYILSRLSEAIEVLPENRE

SVLYVSRDYAYALRARIYLALGEYGKAAADAKMVVDKYPLIGAADASEFE

NIYRSDANNPEIIFRGFASATLGSFTATTLNGAAPAGKDIKYNPSAVPFQ

WVVDLYENEDFRKSVYIAKVVKKDKGYLVNKFLEDKAYRDVQDKPNLKVG

ARYFSVAEVYLILVESALQTGDTPTAEKYLKALSKARGAEVSVVNMEALQ

AERTRELIGEGSRERDMVRWSIPNNHDAFETQPGLEGFANTTPLKAQAPV

GFYAYTWEFPQRDRQTNPQLIKNWPI.

rPG0616 (40 kDa OMP)
The gene was cloned from the W50 strain as described above. Plasmid DNA was isolated and sequenced (sequence set out as SEQ ID NO:42). The sequence of the expressed protein is set out as SEQ ID NO:23. The sequence of the W50 cloned gene (set out as SEQ ID NO:24) is identical to the corresponding W83 sequence from the published genome.
Below is the amino acid sequence of the rPG0616 protein that has been cloned and expressed (vector derived sequence is underlined).

(SEQ ID NO: 23)
MHHHHHHSSGLVPRGSGMKETAAAKFERQHMDSPDLGTDDDDKMQELKTS

ADMKGSFKKNVVLEVFTAEWCGYCPGGKERIAKAIEMLDDEYKERVFQTF

VHYNDGISKKWPRVGQLFIALDQTLGIPGFPTFSVCRMEKKGENLSIGAP

IAIKNKIMKGFGDGTAPAEVNLKLTKGATPEDVCTATFTGKVDADLIGKP

LMLTAYVLKNNMKPINPQNGAGDGYLHQHTVLMILSTDVKGDALNIAADG

SFTIKKEFKLDGFEIKDTDVLAFVHHPMSNAENHSIINAGQESLDKAEPT

ATEQIVATPSVKAYVQNGKIVVEEEYSKMEVFNATGQLVKNESLVPGVYV

VRITANGVMYFLKVLVP

Example 3

Preparation of Protein-Specific Antisera

Antibodies were raised in mice to certain recombinant proteins (e.g. rPG 0495, rPG 2172, rPG 1326, rPG 1374, rPG 0654, rPG 0613, rPG 1798, rPG 0186, rPG 1795, rPG 0616), which had been prepared in accordance to the procedure set out in Example 2.
Mice (Balb/c) were immunized intermuscularly with a 50 µl volume of 50 µg of purified recombinant protein mixed 1/1 (vol/vol) with TiterMax® Gold adjuvant (CytRx Corporation, California, U.S.), for a total injection volume of 100 µl to obtain anti-recombinant polyclonal serum. The TiterMax® Gold adjuvant is a water-in-oil emulsion that includes the block copolymer CRL-8300. The immunization protocol used was as follows:
(i) for each purified recombinant protein, a group of 3 mice were used;
(ii) on day −3, prebleed samples were obtained from each mouse
(iii) on day 0—mice were immunized intermuscularly with a 50 µg dose of purified recombinant protein (using 4×25 µl injections, one in each leg quadracep) with Titer-Max® Gold.
(iv) on day 28—mice were immunized intermuscularly with a 25 µg dose of the same purified recombinant protein and with TiterMax® Gold (using 2×25 µl injections, one in each hind leg quadracep).

(v) Blood samples were obtained from mice following a two week period. Sera from each group was pooled.

The *P. gingivalis* specific antibody responses raised by each recombinant protein were assessed by ELISA. The results obtained from 3 separate studies are summarized in FIGS. 1*a* and 1*b*. As can be noted from FIGS. 1*a* and 1*b*, immunization with 50 μg of each recombinant protein in the presence of TiterMax® Gold elicits a *P. gingivalis*-specific IgG response.

Example 4

Detection of Protein in Outer Membrance of *P. gingivalis*

To assess whether the selected proteins were present in the outer membrane of *P. gingivalis* (and therefore accessible to antibodies), Western immunoblots of *P. gingivalis* (W50) outer membrane fractions were probed with antisera raised to the recombinant proteins (obtained from one of the studies summarized in Example 3).

One protocol that was used to obtain whole cell lysates and outer membrane fractions is provided here. In general, the outer membrane fractions used in the Western immunoblots were obtained using a liquid culture of the *P. gingivalis* W50 strain grown anaerobically. Cells were harvested and fractionated using the detergent Sarkosyl (which selectively solubilizes the inner membrane such that, following Sarkosyl treatment, the Sarkosyl-insoluble material represents the outer membrane fraction.

*P. gingivalis* was grown in BHI media (supplemented with cysteine and hemin) at 37° C. in an anaerobic chamber for ~5-6 days (until culture was turbid). Two 1.5 ml samples of culture was placed into two 2 separate tubes. One sample was centrifuged and the pellet was stored at −20° C. (to be used for whole cell lysate preparation). The second sample was also centrifuged, and the resulting pellet was resuspended in 50 mM sodium phosphate (NaP) (5 mL NaP/1 g cell paste) and stored at −20° C. The whole cell lysate preparation was prepared by thawing pellets, resuspending each 300 μL of 50 mM NaP+300 μL of 4×UMS, and then boiling sample for approximately 10 min. The outer membrane fraction was prepared by thawing one of the pellets resuspended in 50 mM NaP, adding 50 mM NaP to a minimum volume of 20 mL (or the minimum volume required for the sonication apparatus), adding lysozyme to a final concentration of 1 mg/mL. A protease inhibitor tablet was added to the suspension, which was then sonicated on ice and then centrifuged to pellet the unlysed cells. Supernatant was removed. The pellet was resuspended in a 1% sarkosyl solution and incubated for approximately 30 min at room temperature on a rotating mixer and then centrifuged. The resulting supernatant, which contains the inner membrane fragments, was removed and the pellet was resuspended in a 0.5% sarkosyl solution and recentrifuged. The supernatant was extracted and the pellet was resuspended 50 mM NaP+UMS and then boiled. Samples were boiled before being run on gels. Samples were run on gel and each gel included a total of four lanes: (i) a control lane (with purified protein), (ii) a molecular weight standard, (iii) a sample of whole cell lysate and (iv) a sample of the outer membrane fraction. Gels were transferred onto PVDF membranes and probed with the applicable antisera.

Each of PG0495, PG0654, PG1374, PG1795, PG2172, PG0613, PG1326, PG1798, PG0186 and PG0616 was detected in the outer membrane fraction of *P. gingivalis* W50. Results are summarized in FIG. 2.

Example 5

Assessment of Surface Exposure by Flow Cytometry Based Surface Accessibility Assay A flow cytometry based surface accessibility assay (SASSY) was used to measure each protein's accessibility on intact *P. gingivalis* cells to antibody binding. The protein-specific antisera used in this assay were obtained as described in Example 3. A number of SASSY experiments were performed and each was performed in accordance to the following protocol:

*P. gingivalis* strains (W50, W83, 332277) were cultured substantially as described in Example 4; that is, strains were grown in BHI media (supplemented with cysteine and hemin) at 37° C. in an anerobin chamber. In certain experiments, cells were harvested at various stages of growth, early logarithmic, logarithmic or stationary phase and the OD600 measured spectrophotometrically.

To carry out each assay study, a sample of culture was aliquoted into microfuge tubes and centrifuged. The supernatant was pipette-aspirated, and the pellet resuspended in 500 μL/1 mL input culture of 10% FBS and vortexed. The tubes were again centrifuged, the supernatant aspirated and the pellet resuspended in 10% FBS to yield a suspension of ~5E9 CFU/mL based on the estimated CFU/mL of the input culture. The primary antibody was incubated by aliquoting 190 μL/sample of ~5E9 CFU/mL washed bacteria and then adding to each 10 μL of one of the samples to be tested. Each sample was vortexed and then incubated at 37° C. for approximately 30 minutes. Samples were then washed by adding 790 μL 10% FBS to each tube and then mixing by inversion, centrifuging tubes and pipette-aspirating supernatant.

The secondary antibody was incubated as follows: 5 μL of secondary antibody was diluted in DPBS [typically in a 1:1000 ratio]; 200 μL of diluted secondary antibody was added to each primary-antibody bound sample tube; each pellet was then resuspended by pipetting with a single-channel pipetter, and vortexed. As a control, a tube did not receive secondary antibody, but received 10% FBS instead. Tubes were incubated at room temperature for approximately 30 minutes in the dark. Samples were then washed by adding 10% FBS to each tube and mixing by inversion. Tubes were centrifuged and supernatant was pipette-aspirated. Each sample was fixed by adding % PFA. Samples were stored at 2-8° C., in the dark.

Antisera raised against Formalin-Killed W50 Whole Cells (FKWC) was used as a positive control (the generation of this sera is described in more detail in Example 6). AF488-conjugated Goat anti-Mouse IgG was used to detect bound antisera.

Samples were acquired on a FACS Calibur Flow cytometer (Becton Dickison). The cytometer used a 488 nm wavelength band generated from an argon ion laser. Emission signals (AlexaFluor-488 for SASSY and CFSE for OPA-uptake) were collected for each analysis which consisted of 10,000 gated events that were collected on the basis of size and granularity using CELLQuest Pro software (Becton Dickinson). Samples were analyzed using the FlowJo7.2.5 software FIG. 2 provides a summary of the results obtained from a number of separate experiments for each protein tested. Each dot set out along the Y axis represents the result obtained using that protein's protein-specific antisera in one SASSY experiment. Each horizontal dash set out along the Y axis represents the average result obtained in the all of the SASSY experiments performed using that protein's protein-specific antisera. Each of PG0495, PG0654, PG1374, PG1795, PG2172, PG0613, PG1326, PG1798, PG0186 and PG0616 were detected by SASSY as surface exposed on the *P. gingivalis* W50 strain at stationary phase.

The surface accessibility of each of these proteins (PG0495, PG0654, PG1374, PG1795, PG2172, PG0613, PG1326, PG1798, PG0186 and PG0616) on two other *P. gingivalis* strains (W83 and ATCC33277) and on the W50 strain at different growth phases was also evaluated. *P. gingivalis* strain W50 was grown to early logarithmic, logarithmic, or stationary phase and *P. gingivalis* strains W83 and ATCC33277 were grown to stationary phase. Surface accessibility was assessed using the flow cytometry based assay described above.

Figure 6:
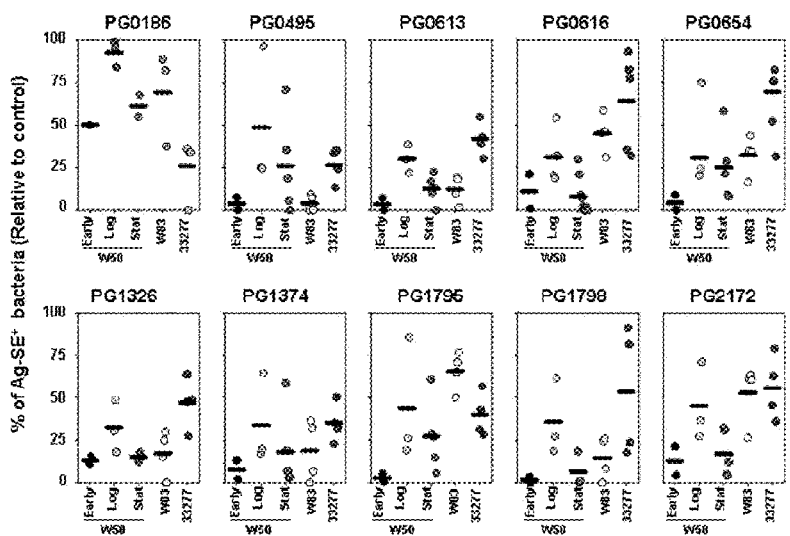

FIG. 6 provides a summary of the results obtained from the various experiments performed with each protein. Each dot (•) set out on the Y axis represents the result obtained in one assay using the applicable protein's protein-specific antisera. Each horizontal dash (-) set out along the Y axis represents the average of the results obtained from all experiments performed using a protein's protein-specific antisera. Each of PG0186, PG0495, PG0613, PG0616, PG0654, PG1326, PG1374, PG1795, PG1798, and PG2172 were detected as surface exposed on the three *P. gingivalis* strains. For most proteins, the degree of exposure varied between two or more strains. Antigen exposure also varied during the different growth phases evaluated of the W50 strain (i.e., early logarithmic, logarithmic, or stationary), with maximum exposure seen during the logarithmic phase of growth.

Example 6

Assessment of Immunogenicity of SE Protein Candidates

A Th2-antibody biased response is associated with protection in the prophylactic alveolar bone loss model (*J. Immunol.* 2008 Sep. 15; 181(6):4150-8). In a periodontitis mouse challenge model, immunized mice with a bias toward a Th1 response resulted in elevated levels of periodontal tissue inflammation and alveolar bone loss in mice following challenge with *P. gingivalis*, whereas mice that were biased toward a Th2 response did not develop periodontal bone loss (*Am. J. Pathol.* 2007; 170:203-213). Murine IgG1 has limited Fc-associated effector functions; it binds only to FcγRIII and fails to activate complement by the classical pathway (Klaus, 1979).

To assess the type of response elicited by the recombinant polypetides, mice (BALB/c) were immunized intramuscularly with purified recombinant polypeptide (with or without adjuvant).

The immunization protocol used was as follows:
(i) Prebleed samples were taken prior to the commencement of procedure (on day 0). The first immunization took place on day 7.
(ii) For each purified recombinant protein, 2 groups of 8 mice were used. One group was immunized intramuscularly at one site with protein (5 μg) in 0.56 mg/ml adjuvant (i.e. Alhydrogel '85' 2% (aluminum oxyhydroxide)), in a total volume of 50 μl and the second immunized intramuscularly at one site with protein (5 μg) alone (in a total volume of 50 μl).
(iii) As controls, mice were immunized with formalin killed whole *P. gingivalis* W50 cells (FKWC), prepared substantially as described previously in Rajapakse et al. 2002. One group of 8 mice were immunized with $10^{10}$ cfu FKWC alone (in a total volume of 50 μl), a second group of 8 mice were immunized with $10^{10}$ cfu FKWC plus 0.56 mg/ml adjuvant (i.e., Alhydrogel '85' 2%) in a total volume of 50 μl.
(iv) Sample bleeds were taken from each mouse on day 20.
(v) A boost was given to mice on day 21 (i.e. a second injection, identical to the first)
(vi) Two weeks later, mice were exsanguinated. Sera from each group was not pooled.

Endpoint titers for IgG, IgG1 and IgG2a were determined by ELISA (i.e. by using as a standard the OD observed with a known concentration of FKWC antibodies reacting with FKWC-coated microtitration plates. The IgG1/IgG2a ratio was also determined. The ratio of IgG1 to IgG2a is routinely used by persons of skill in the art as an indirect measure of the relative size of the Th2 and Th1 components of the immune response. High and low ratios indicate responses dominated by the Th2 and Th1 components of the immune response, respectively.

Figure 3:
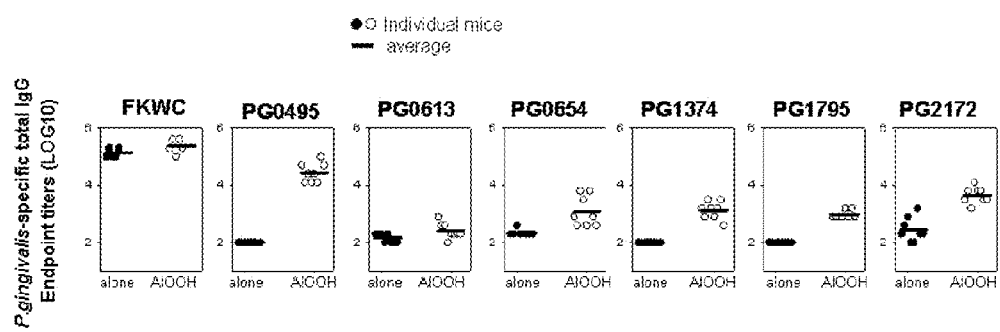
FIG. 3 Depicts anti-P. gingivalis protein IgG antibody responses. Groups of mice were immunized with P. gingivalis polypeptide in the presence of or in the absence of aluminum hydroxide. P. gingivalis specific IgG antibody titers were measured. Each bar represents the mean antibody titer and symbols correspond to a single mouse of each group.

FIG. 3 and Table 5 set out the results obtained. FKWC antisera gave high *P. gingivalis* specific IgG endpoint titer. These ELISAS, using FKWC-coated microtitration plates, demonstrated that FKWC administered alone (i.e., without adjuvant) raised a Th1-biased response. Each of the recombinant polypeptides were shown to elicit a *P. gingivalis* specific Th2-biased antibody response when injected with AlOOH, the highest by rPG0495 and rPG2172.

TABLE 5

| Antigen | Adjuvant | Ratio (IgG1/IgG2a) |
|---------|----------|---------------------|
| FKWC    | None     | 0.5                 |
| FKWC    | AlOOH    | 4.0                 |
| rPG0495 | AlOOH    | 789.0               |
| rPG0613 | AlOOH    | 5.6                 |
| rPG0654 | AlOOH    | 10.4                |
| rPG1374 | AlOOH    | 64.0                |
| rPG1795 | AlOOH    | 38.0                |
| rPG2172 | AlOOH    | 166.0               |

Example 6b

Assessment of Antigen-Specific Immunogenicity of Proteins

The immune response elicited by each of the proteins was assessed in a second study. In this second study, ELISAs were performed using microtitration plates coated with the individual specific antigens. This allowed for the evaluation of the antigen-specific immunogenicity of each individual protein.

Groups of BALB/c mice were immunized intramuscularly with purified recombinant polypeptide (with or without adjuvant) in accordance with an immunization protocol substantially as described above. Mice were immunized intramuscularly at one site with protein (with either 5 or 25 μg/dose) in 0.56 mg/ml adjuvant (i.e., Alhydrogel '85' 2%) in a total volume of 50 μl or immunized intramuscularly at one site with protein alone (with either 5 or 25 μg/dose) in a total volume of 50 μl. Prebleed samples were taken prior to the commencement of the procedure (on day 0) and the first immunization took place on day 7. As with the earlier study, a boost was administered on day 21 (i.e., on day 21, a second injection, identical to the first, was administered) and two weeks later, mice were exsanguinated and serum samples were prepared. For each recombinant polypeptide tested, the number of groups used and the number of mice per group is set out in Table 7 below.

TABLE 7

| Antigen | No. of groups | Group | Adjuvant | Dose (µg) | No. of mice |
|---|---|---|---|---|---|
| PG0186 | 2 | #1: | — | 5 | 5 |
|  |  | #2: | AlOOH | 5 | 15 |
| PG0495 | 4 | #1: | — | 5 | 8 |
|  |  | #2: | AlOOH | 5 | 8 |
|  |  | #3: | — | 25 | 5 |
|  |  | #4: | AlOOH | 25 | 15 |
| PG0613 | 4 | #1: | — | 5 | 8 |
|  |  | #2: | AlOOH | 5 | 8 |
|  |  | #3: | — | 25 | 5 |
|  |  | #4: | AlOOH | 25 | 15 |
| PG0616 | 2 | #1: | — | 5 | 20 |
|  |  | #2: | AlOOH | 5 | 30 |
| PG0654 | 4 | #1: | — | 5 | 8 |
|  |  | #2: | AlOOH | 5 | 8 |
|  |  | #3: | — | 25 | 5 |
|  |  | #4: | AlOOH | 25 | 15 |
| PG1326 | 2 | #1: | — | 5 | 5 |
|  |  | #2: | AlOOH | 5 | 15 |
| PG1374 | 4 | #1: | — | 5 | 8 |
|  |  | #2: | AlOOH | 5 | 8 |
|  |  | #3: | — | 25 | 5 |
|  |  | #4: | AlOOH | 25 | 15 |
| PG1795 | 4 | #1: | — | 5 | 8 |
|  |  | #2: | AlOOH | 5 | 8 |
|  |  | #3: | — | 25 | 5 |
|  |  | #4: | AlOOH | 25 | 15 |
| PG1798 | 2 | #1: | — | 5 | 5 |
|  |  | #2: | AlOOH | 5 | 15 |
| PG2172 | 4 | #1: | — | 5 | 8 |
|  |  | #2: | AlOOH | 5 | 8 |
|  |  | #3: | — | 25 | 5 |
|  |  | #4: | AlOOH | 25 | 15 |

Endpoint titers for IgG, IgG1, IgG2a of sera from individual mice were determined by protein-specific ELISA and the IgG1:IgG2a ratio was calculated. An example of an ELISA protocol utilized is provided here.

Microtiter plates (Nunc-Immuno MaxiSorp, flat bottom polystyrene) were coated overnight at room temperature (RT) with 100 microl of specific recombinant proteins at 0.5 µg/mL (50 ng/well) in 0.05M Carbonate-Bicarbonate Buffer, pH 9.6. Plates were washed twice with 200 µL/well of wash buffer (1×PBS+0.1% Tween-20) then blocked for 60 min at RT with 150 µL/well of 1% BSA in PBS.

Two-fold serially diluted serum samples from individual mice were then added and plates were incubated for 60 min at RT. Plates were washed four times with 200 microL/well of wash buffer. Hundred microL/well of HRP-conjugated secondary Abs (F(ab')2 goat anti-mouse IgG (H+L):HRP diluted at 1:10'000, F(ab')2 goat anti-mouse IgG1 (H+L):HRP diluted at 1:20'000, or F(ab')2 goat anti-mouse IgG2a (H+L):HRP diluted at 1:20'000) were then incubated for 60 min at RT. Plates were washed four times with 200 microL/well of wash buffer. Hundred microL/well of TMB (HRP substrate) was added to the plates and incubated for 15 min at RT then reaction was stopped by adding 50 microL/well of 1M H2SO4. OD values were determined by reading plates on spectrophotometer wavelength 450 nm using prepared templates on SOFTmax Pro v5.2.

The endpoint Titer is defined as the reciprocal of the highest dilution of a serum that gives a reading above the cutoff. The determination of the endpoint titer is based on the cutoff value. To establish the endpoint titer, a cutoff is chosen for every single step and readings of the entire dilution of the entire dilution series are compared with the respective cutoffs. The cutoff OD450 value chosen is 0.100.

The endpoint is reached when a dilution produces a reading lower than or equal to the cutoff. The reciprocal of the previous dilution is reported as the endpoint titer.

A summary of the results obtained are set out in Table 8. As shown, each protein was immunogenic at both doses administered (5 and 25 µg) with higher total IgG responses elicited with the higher dose (25 µg). Higher total IgG responses were elicited when the protein was administered in the presence of adjuvant (aluminum hydroxide). Notably, the proteins when adjuvanted elicited a Th2 biased protein specific IgG response. These results show that each of the proteins evaluated are immunogenic and are capable of eliciting the desired Th2 biased protein specific IgG response when appropriated adjuvanted (such as for example with an aluminum compound, e.g., aluminum hydroxide). Those of skill in the art will appreciate that other adjuvants may be used. Particularly suitable, are those adjuvants which when administered with the proteins of the present invention provide a Th2 biased response.

TABLE 8

| | | | Ag-specific IgG endpoint titer (LOG10) | | | |
|---|---|---|---|---|---|---|
| Antigen | Adjuvant | Dose (µg) | IgG[a] | IgG1[a] | IgG2a[a] | Ratio IgG1:IgG2[b] |
| PG0186 | — | 5 | 2.9 ± 0.3 | 2.9 ± 0.6 | 1.7 ± 0.0 | 16.0 |
|  | AlOOH | 5 | 4.0 ± 0.2 | 4.0 ± 0.3 | 1.7 ± 0.0 | 229.0 |
| PG0495 | — | 5 | 2.1 ± 0.3 | 2.2 ± 0.5 | 1.7 ± 0.1 | — |
|  | AlOOH | 5 | 5.8 ± 0.1 | 6.0 ± 0.3 | 3.2 ± 0.2 | 624.1 |
|  | — | 25 | 4.0 ± 1.2 | 4.1 ± 1.1 | 2.8 ± 0.7 | 21.1 |
|  | AlOOH | 25 | 6.4 ± 0.2 | 6.8 ± 0.3 | 4.2 ± 0.4 | 466.8 |
| PG0613 | — | 5 | 2.2 ± 0.5 | 2.2 ± 0.6 | 1.8 ± 0.3 | — |
|  | AlOOH | 5 | 4.3 ± 0.3 | 4.7 ± 0.3 | 1.8 ± 0.3 | 789.6 |
|  | — | 25 | 3.2 ± 0.6 | 3.5 ± 0.7 | 1.7 ± 0.1 | 55.7 |
|  | AlOOH | 25 | 5.4 ± 0.2 | 5.9 ± 0.2 | 3.2 ± 0.9 | 466.8 |
| PG0616 | — | 5 | 3.2 ± 0.7 | 3.3 ± 1.0 | 2.7 ± 0.9 | 4.0 |
|  | AlOOH | 5 | 5.2 ± 0.6 | 5.3 ± 0.5 | 3.5 ± 0.8 | 67.7 |
| PG0654 | — | 5 | 2.9 ± 0.4 | 3.1 ± 0.5 | 2.4 ± 0.7 | 8.8 |
|  | AlOOH | 5 | 5.0 ± 0.2 | 5.4 ± 0.2 | 3.8 ± 0.0 | 64.0 |
|  | — | 25 | 4.6 ± 0.4 | 4.8 ± 0.4 | 3.5 ± 0.5 | 19.0 |
|  | AlOOH | 25 | 5.5 ± 0.3 | 5.9 ± 0.3 | 3.3 ± 0.7 | 445.7 |
| PG1326 | — | 5 | 5.3 ± 0.6 | 5.2 ± 0.5 | 4.2 ± 1.2 | 16.0 |
|  | AlOOH | 5 | 6.3 ± 0.2 | 6.3 ± 0.2 | 4.3 ± 0.8 | 111.4 |
| PG1374 | — | 5 | 2.2 ± 0.2 | 2.3 ± 0.5 | 1.7 ± 0.0 | 4.0 |
|  | AlOOH | 5 | 5.0 ± 0.4 | 5.2 ± 0.2 | 2.4 ± 0.6 | 673.8 |
|  | — | 25 | 3.2 ± 0.5 | 3.6 ± 0.5 | 1.8 ± 0.3 | 55.7 |
|  | AlOOH | 25 | 5.9 ± 0.2 | 6.0 ± 0.5 | 2.9 ± 0.4 | 1123.1 |

TABLE 8-continued

| | | | Ag-specific IgG endpoint titer (LOG10) | | | |
|---|---|---|---|---|---|---|
| Antigen | Adjuvant | Dose (μg) | IgG[a] | IgG1[a] | IgG2a[a] | Ratio IgG1:IgG2[b] |
| PG1795 | — | 5 | 2.9 ± 0.4 | 2.8 ± 0.7 | 2.0 ± 0.3 | 6.7 |
| | AlOOH | 5 | 5.1 ± 0.3 | 5.1 ± 0.3 | 2.2 ± 0.6 | 755.6 |
| | — | 25 | 4.9 ± 0.6 | 5.1 ± 0.5 | 3.7 ± 1.1 | 21.2 |
| | AlOOH | 25 | 6.3 ± 0.2 | 6.6 ± 0.3 | 4.1 ± 0.6 | 308.0 |
| PG1798 | — | 5 | 3.6 ± 0.7 | 3.6 ± 0.4 | 2.2 ± 0.6 | 23.7 |
| | AlOOH | 5 | 4.7 ± 0.3 | 4.8 ± 0.2 | 1.9 ± 0.2 | 891.4 |
| PG2172 | — | 5 | 3.2 ± 0.8 | 3.2 ± 0.9 | 2.4 ± 0.7 | 5.9 |
| | AlOOH | 5 | 5.0 ± 0.2 | 5.3 ± 0.1 | 2.6 ± 0.5 | 621.1 |
| | — | 25 | 5.5 ± 0.4 | 5.1 ± 0.4 | 4.6 ± 0.6 | 4.0 |
| | AlOOH | 25 | 6.4 ± 0.3 | 6.6 ± 0.2 | 4.8 ± 0.4 | 57.6 |

[a]Numbers represent the arithmetic mean ± standard deviation of LOG10 values derived from the endpoint titers of all the mice for each group
[b]The ratio is calculated by dividing the respective initial endpoint titers. Numbers represent the geometric mean of the ratio from all the individual mice per group.

Example 7

Serum Bactericidal Activity

Antisera generated substantially as described in Example 6 was assessed in two separate studies for serum bactericidal activity (SBA). Such an assay is well known to one skilled in the art. Positive SBA activity of an antigen-specific serum may indicate that the particular antigen would induce a protective immune respond against infection with the corresponding bacteria.

Figure 4:
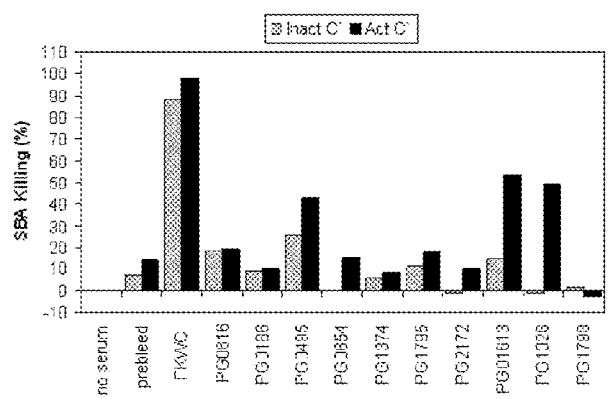
FIG. 4 Depicts serum bactericidal activity of serum samples obtained from mice immunized with proteins FIG. 5 Depicts opsonophagocytic study activity of specific anti-protein sera FIG. 6 Depicts accessibility of proteins on cell surface of three strains of P. gingivalis (W50, W83, ATCC33277) as measured by a flow cytometry based assay. Additionally, the accessibility of proteins on P. gingivalis W50 grown to different growth phases was also assessed. Each dot on the Y-axis represents the result obtained in an assay performed using protein specific antisera.

An example of the method utilized is set out here. In brief, a known quantity of bacterial cells (*P. gingivalis*) are incubated with control or immune sera, in the presence of active or inactivated complement. The level of bacterial killing by the serum bactericidal activity is assessed after 1 hour by plating and counting surviving bacteria. Specifically, for each sample and control, 214 μL containing approximately $1.26 \times 10^7$ cfu of *P. gingivalis* (strain W50) was aliquoted into a separate well of a sterile microtitre plate, on ice in the anaerobic chamber. For each test sample and control 10 μL of active or inactive complement was aliquoted to separate wells. applicable well 12.52 μL of one of the applicable sera was added and mixed by pipetting (the result was a 20-fold dilution of serum in the SBA reaction). For each sample and control, 90 μL of the bacteria+serum mixture was aliquoted to both wells containing active or inactive complement. The contents of each well was mixed by pipetting. Tubes were incubated at room temperature for approximately 60 minutes in an anaerobic chamber.
Dilutions:
For each test sample and control prepared 3 serial 10-fold dilutions were prepared as follows: 20 μL SBA reaction into 180 μL BHI+ Broth, 1 serial 6.25-fold dilution 32 μL SBA reaction into 168 μL BHI+ Broth and 3 serial 2.5-fold dilutions 80 μL SBA reaction into 120 μL BHI+ Broth. Cumulatively, the resultant dilution factors are 10, 100, 1000, 6250, 15625, 3.90625E4 and 9.765625E4.
Plating:
For each sample and control plated 3×10 μL of each of the three highest dilutions were plated onto BHI+ Blood Agar. This results in a plating factor of 100. Once the inoculated plates were dry, they were inverted and incubated at room temperature in an anaerobic chamber for 4-7 days.
FIG. 4 sets out a summary of the SBA results obtained for each recombinant protein, with active or inactive complement. At the one dilution of serum tested, PG0495, PG613 and PG1326 each showed slight bactericidal activity. While the other proteins showed less or no detectable SBA activity, they may induce a protective immune response to infection utilizing a different immune mechanism.

Example 8

Opsonophacocylosis Assay

An assay was performed to assess the opsonic activity of the polyclonal sera of certain *P. gingivalis* proteins (i.e. rPG0495, rPG2172, rPG1326, rPG654, rPG1374, rPG1795, rPG0613 and rPG0616). Antisera generated substantially as described in Example 6 was assessed. Samples of prebleed sera and of diluent (with no serum) were used as experimental controls.

A bacterial culture of *P. gingivalis* W50, was grown to approximately $5.0 \times 10^9$ cfu/mL. Cells were pelleted by centrifugation and then washed twice with 1% PBS and labeled with CFSE. Solution of CFSE prepared by adding IF Buffer to DDAO-SE. Solution was kept in the dark and incubated for 15 min at 37 C. Samples were wash×2 with PBS. OPA buffer was then added to samples.

Serum sample was prepared at 1/50 final for opsonization step (final volume 200 ul, add 50 ul/well) and 1/12.5 dilution in OPA Buffer. Samples were heat inactivated for 30 min at 56° C. Inactivated or Active complement was diluted in OPA buffer (1% in final reaction) and then added to samples. On ice the opsonization reaction was started by adding in order Medium, Serum, Complement and Bacteria. Samples were then incubate at room temperature on a shaking incubator (700 vibrations/min) for 30 minutes.

Differentiated HL-60 cell line (ATCC CCL-240) was used as phagocyte. HL-60 cell suspension that have been differentiated for 6 days with DMF 100 mM at a $4 \times 10^5$ cell density were harvested, washed in 1×HBSS, then resuspend in OPA buffer to $5 \times 10^6$ cell/ml. 200 μl of HL-60 cell suspension were added to opsonized bacteria and incubated 30 min at 37° C. shaking incubator (700 vibrations/min). Opsonophagocytosis was stopped on ice. Samples were kept on ice and acquired on a FACS Calibur Flow cytometer (Becton Dickison) within 2 hours after the end of the reaction. CSFE Emission signals were collected for each analysis which consisted of 10,000 HL-60 gated events that were collected on the basis of size and granularity using CELLQuest Pro software (Becton Dickinson). Samples were analyzed using the FlowJo7.2.5 software.

Figure 5:
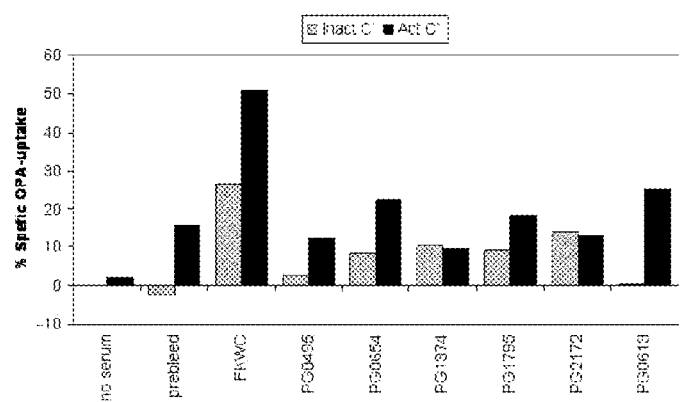

The results obtained are summarized in FIG. 5. At the given dilution tested PG 1374 and PG 0613 each showed slight OPA activity. While the other proteins showed less or no detectable OPA activity, they may induce a protective immune response to infection utilizing a different immune mechanism.

Example 9

Haemagglutination Activity

The ability of antisera raised to certain *P. gingivalis* proteins to inhibit hemagglutination activity (HAI) induced by the bacterium (or bacterial supernate) was assessed. Anti-Haemagglutination activity is a characteristic that has been associated with protective immune serum elicited against a number of pathogens. In some cases, HAI is a known correlate assay for protection against disease (e.g., influenza). Antisera generated substantially as described in Example 6 were tested for HAI. The method used for assessing hemagglutination activity is described below.

*P. gingivalis* strains W83 and W50 were grown to stationary phase. Culture samples were centrifuged and the supernatant (media fraction) was separated from the pellet fraction (Whole cells). The pellets were washed using Dulbecco's PBS (Gibco) and resuspended to ~1 OD/mL. Sheep's Red Blood Cells (RBCs) were also washed using Dulbecco's PBS and the pellet was used to prepare a 1% Sheep's Blood mix. Supernatant and Pellet (1 OD/mL) samples of each strain were serially diluted 2-fold using Dulbecco's PBS for a final volume of 100 ul per well. 100 ul of 1% Sheep's blood was added to all wells containing sample for a final concentration of 0.5% RBCs. These HA assays were incubated (stationary) at Room Temp or 4° C. in aerobic conditions for at least 3 hours. At 3 hours, the plates were observed and a well close to the last well with complete HA was chosen for the Hemagglutination Inhibition Assays.

Sera samples (to test if they can inhibit Hemagglutination of *P. gingivalis* to RBCs) were either purified using the Melon Gel IgG purification kit (Thermo Fisher) or left alone as "crude", non-purified sera samples.

Sera samples were serially diluted 2-fold in Dulbecco's PBS. *P. gingivalis* samples were diluted to the concentration of the chosen well that was close to the last well with complete HA (See above HA Assay). 50 ul of sera+50 ul of *P. gingivalis* sample was mixed in a 96-well plate. No antibody control=50 ul of *P. gingivalis*+Dulbecco's PBS. Other controls include 50 ul sera+50 ul PBS or BHI Media, and 100 ul PBS or BHI Media alone. The plate was rocked gently for 1 hr at 37° C. 100 ul of 1% sheep's blood was added to all wells containing sample for a final concentration of 0.5% Sheep's RBCs. The plates were incubated (statically) at 4° C., aerobically overnight. (~16-20 hrs) and observed. The HAI titer was defined by visualizing the most dilute sample of serum which was still able to inhibit the hemagglutination activity of the bacterial pellets or supernate. For significance, the HAI titer of an immune serum should be at least >2 times the HAI titer of the prebleed serum samples. The HAI titers are shown in Table 9.

TABLE 9

| | | HAI Titer | |
| --- | --- | --- | --- |
| | | W83 | W50 |
| rPG0495 | Supernate | 160 | 320 |
| | Pellet | 40 | 160* |
| rPG0613 | Supernate | 160 | 320 |
| | Pellet | 40 | 80 |
| rPG0654 | Supernate | 160 | 320 |
| | Pellet | <40 | 80 |

TABLE 9-continued

| | | HAI Titer | |
| --- | --- | --- | --- |
| | | W83 | W50 |
| rPG1374 | Supernate | 160 | 320 |
| | Pellet | 40 | 80 |
| rPG1795 | Supernate | 160 | 640* |
| | Pellet | 40 | 80 |
| rPG2172 | Supernate | 160 | 5120* |
| | Pellet | <40 | 160 |
| FKWC | Supernate | 1280* | 320 |
| | Pellet | 160 | 80 |
| Prebleed | Supernate | 160 | 320* |
| | Pellet | <40 | 80* |
| rPG0616 | Supernate | 80* | 320* |
| | Pellet | <40* | 80* |
| Prebleed | Supernate | 160 | 320 |
| | Pellet | <40 | 80 |

The HAI titers noted with the symbol "*" were 2 times the pre-bleed background. This indicates that antibodies to these antigens inhibit HA activity of *P. gingivalis*.

Example 10

The Efficacy of Recombinant Proteins to Protect Against Challenge with *P. gingivalis*

The protective efficacy of each purified protein, alone or in combination is evaluated in a well established prophylactic murine periodontal bone loss model, described previously (5). In studies using such a model, a Th2-biased response (with associated changes in IgG subclass distribution) has been shown to correlate with protection against *P. gingivalis* induced bone loss. Mice (BALB/c, 6-8 week old) are immunized s.c. with each recombinant protein (10-50 µg/dose) or with a combination of purified recombinant proteins (10-50 µg/dose/protein) selected from the group consisting of PG0186, PG0495, PG0613, PG0616, PG0654, PG1326, PG1374, PG1795, PG1798, and PG2172 in the presence and absence of various adjuvants that provide the appropriate Th2-biased response (such as for example, aluminum hydroxide or Alhydrogel) to assess protection against a challenge with *P. gingivalis*. The recombinant protein or proteins are derived from *P. gingivalis* strain W50 (or W83), by known methods, such as for example, as described in Example 2. One to 3 booster doses can be administered at 1-2 week intervals (or at longer intervals) and mice are bleed about 12 days later from the retrobulbar plexus. After bleeding, mice receive kanamycin at 1 mg/ml in deionized water ad libitum for 7 days. Three days after antibiotic treatment, mice are orally challenged, 2 days apart with $1 \times 10^{10}$ viable *P. gingivalis* strain W50 cells and a control group is sham-infected with PG buffer containing 2 g/100 ml carboxymethylcellulose alone (as described previously (5)). The mice are sacrificed 28 days following challenge and maxillae are removed and prepared. Horizontal bone loss is assessed as previously described (5). Sera is collected and antibody titers are measured by ELISA.

While the present invention has been described in terms of the preferred embodiments, it is understood that variations and modifications for example to the compounds, compositions and methods described herein will occur to those skilled in the art. Therefore, it is intended that the appended claims cover all such equivalent variations that come within the scope of the invention as claimed.

REFERENCES

The content of the following are incorporated by reference in their entirety:
1. L. Frazer, et al., "Vaccination with recombinant adhesins from the RgpA-Kgp proteinase-adhesin complex protects against *Porphyromonas gingivalis* infection," 24 (42-43), 6542 (2006)
2. N. M. O'Brien-Simpson, et al., "Serum immunoglobulin G (IgG) and IgG subclass responses to the RgpA-Kgp proteinase-ashesin complex of *Porphyromonas gingivalis* in adult periodontitis 68(5) 2704 (2000)
3. N. M. O'Brien-Simpson, et al., "Role of RgpA, RgpB and Kgp proteinases in virulence of *Porphyromonas gingivalis* W50 in a murine lesion model," 69(12), 7527 (2001).
4. N. M. O'Brien-Simpson et al, "RgpA-Kgp peptide-based immunogens provide protection against *Porphyromonas gingivalis* challenge in a murine lesion model," 68(7), 4055 (2000)
5. N. M O'Brien-Simpson, et al, "An immune response directed to proteinase and adhesin functional epiptopes protects against *Porphyromonas gingivalis*-induced periotontal bone lone," 175(6), 3980 (2005)
6. N. M. O'Brien-Simpson et al., "*Porphyromonas gingivalis* RgpA-Kgp proteinase-adhesin complexes penetrate gingival tissue and induce pro-inflammatory cytokines or apoptosis in a concentration-dependant manner", (2008)
7. N. M. O'Brien-Simpson et al., "Antigens of bacteria associated with periodontitis", 35, 101 (2004)
8. V. Tam et al., "Characterization of T Cell Responses to the RgpA-Kgp Proteinase-Adhesin Complexes of *Porphyromonas gingivalis* in BALB/c Mice," 181(6), 4150 (2008)
9. Booth V et al., Passive immunization with monoclonal antibodies against *Porphyromonas gingivalis* in patients with periodontitis. Infect Immun. 1996 February; 64(2): 422-7
10. Yokoyama, Effects of egg yolk antibody against *P. gingivalis* gingipains in periodontitis patients. J Oral Sci. 2007 September; 49(3):201-6
11. Holt S C, Kesavalu L, Viriulence factors of *P gingivalis*. Periodontal 2000.1999 June 20:168-238
12. Nelson K E, et al, complete genome sequence of the oral pathogenic bacterium *P. gingivalis* strain W83. J. Bacteriol. 2003 September; 185(18):5591-601
13. "Determination of the Genome Sequence of *Porphyromonas gingivalis* Strain ATCC 33277 and Genomic Comparison with Strain W83 Revealed Extensive Genome Rearrangements in *P. gingivalis*", DNA Res. 2008 August; 15(4): 215-225.

---

The invention claimed is:

1. An immunogenic composition comprising at least one isolated polypeptide, an adjuvant that induces a Th2-biased immune response, and a pharmaceutically acceptable carrier, wherein the at least one polypeptide is selected from the group consisting of *Porphyromonas gingivalis* protein PG2172 (SEQ ID NO. 3), a polypeptide having at least 80% identity to SEQ ID NO. 3, an immunogenic fragment of 8, 9, 10, 12, 13, 16, 18, 20, 25, 30, 35, 40, 50, 60, 70, 80, 90, 100, 150, 200 or more consecutive amino acids of SEQ ID NO. 3, and a variant comprising a conservative substitution of at least one amino acid of SEQ ID NO. 3.

2. An immunogenic composition comprising at least one isolated polypeptide having at least 80% identity to SEQ ID NO. 3, an adjuvant that induces a Th2-biased immune response, and a pharmaceutically acceptable carrier.

3. The immunogenic composition of claim 1 or 2 wherein the adjuvant is an aluminum salt adjuvant.

4. The immunogenic composition of claim 3 wherein the aluminum salt adjuvant is an aluminum hydroxide or aluminum phosphate.

5. The immunogenic composition of claim 4 wherein the aluminum salt adjuvant is an aluminum hydroxide.

6. The immunogenic composition of claim 2 wherein the immunogenic composition is formulated for use orally.

7. The immunogenic composition of claim 2 wherein the immunogenic composition is formulated for percutaneous administration.

8. The immunogenic composition of claim 2 wherein the immunogenic composition is in a kit form comprising the composition and instructions for use.

9. *P. gingivalis* protein PG2172 (SEQ ID NO. 3), or an immunogenic fragment consisting of 8, 9, 10, 12, 13, 16, 18, 20, 25, 30, 35, 40, 50, 60, 70, 80, 90, 100, 150, 200 or more consecutive amino acids of SEQ ID NO. 3, or a variant comprising a conservative substitution of at least one amino acid of SEQ ID NO. 3, immobilized on a solid support or solid matrix.

10. A polypeptide having at least 80% identity to SEQ ID NO. 3 immobilized on a solid support or solid matrix.

11. An immunogenic composition comprising at least one isolated polypeptide and a pharmaceutically acceptable carrier, wherein the at least one polypeptide consists of the amino acid sequence as set out in SEQ ID NO: 29.

12. The immunogenic composition of claim 11 further comprising an adjuvant.

13. The immunogenic composition of claim 12 wherein the adjuvant is an aluminum salt adjuvant.

14. The immunogenic composition of claim 13 wherein the aluminum salt adjuvant is an aluminum hydroxide or aluminum phosphate.

15. The immunogenic composition of claim 14 wherein the aluminum salt adjuvant is an aluminum hydroxide.

* * * * *

SEQUENCE LISTING

```
<160> NUMBER OF SEQ ID NOS: 79

<210> SEQ ID NO 1
<211> LENGTH: 469
<212> TYPE: PRT
<213> ORGANISM: Porphyromonas gingivalis (strain W83; PG0495)

<400> SEQUENCE: 1

Met Arg Lys Ile Ile Met Lys Lys Leu Phe Leu Ala Ser Val Ala Phe
1               5                   10                  15

Leu Cys Ala Trp Ile Trp Ser Ala Asn Ala Gln Thr Met Ala Pro Asn
            20                  25                  30

Tyr Phe His Ala Asp Pro Gln Gln Phe Lys His Arg Ile Val Lys Glu
        35                  40                  45

Lys Ser Phe Ser Ser Tyr Ser Asn Tyr Glu Tyr Gly Val Asp Asn Arg
    50                  55                  60

Leu Gln Arg Ile Tyr Ser Val Asp Glu Ser Ser Gly Glu Ile Glu His
65                  70                  75                  80

Glu Arg Arg Phe Phe Phe Asn Glu Gly Gly Tyr Met Ile Arg Glu Glu
                85                  90                  95

Glu Tyr Asp Gly Thr Val Gln Ile Pro Val Arg Lys Trp Glu Phe Val
            100                 105                 110

Arg Asp Asp Lys Gly Tyr Ile Thr His Phe Ser Arg Tyr Ser Pro Lys
        115                 120                 125

Asp Gly Ser Gln Glu Leu Ile Glu Asp Ile Arg Ile Asp Phe Ser Tyr
    130                 135                 140

Asp Ala Asp Met Lys Leu Ile Lys Ala Asp Ile Asp Phe Phe Asp Ile
145                 150                 155                 160

Met Ala Asn Val Trp Gly Asp Leu Arg Thr Thr Lys Leu Val Tyr Asn
                165                 170                 175

Glu Asn Gly Leu Leu Lys Glu Met Ile Gln Thr Asp Pro Gly Ser Gly
            180                 185                 190

Gln Glu Phe Asn Arg Glu Glu Leu Thr Tyr Asn Asn Leu Asn Lys Ile
```

```
            195                 200                 205
Val Ala Ile Arg Phe Ile Pro Gly Pro Ala Ser Thr Gly Leu Asn Glu
    210                 215                 220

Phe Glu Leu Ile Tyr Glu Tyr Asp Ser Glu Gly Met Asp Ile Val Lys
225                 230                 235                 240

Ala Gly Arg Asp Asp Phe Trp Tyr Tyr Glu Tyr Asp Lys Glu Met
                245                 250                 255

Leu Ala Ser Glu Thr Phe Phe Pro Lys Pro Ser Ile Ala Asp Leu Val
        260                 265                 270

Tyr Phe Gly Leu Lys Asp Tyr Val Asp Phe Ser Gly Leu Pro Phe Lys
    275                 280                 285

Asn Ser Tyr Thr His Val Val Lys Glu Ser Thr Asn Glu Val Glu
    290                 295                 300

Ala Ile Tyr Glu Pro Ile Ser Val Tyr Ser Val Val Ile Gln Pro
305                 310                 315                 320

Glu Asn Gly Glu Ile Lys Leu Thr Ala Asp Gly Gln Pro Leu Asn Ser
                325                 330                 335

Gly Ser Thr Leu Val Ala Gly Arg Arg Ile Lys Ile His Pro Ile Pro
        340                 345                 350

Ala Glu Gly Tyr Glu Val Asp Lys Val Met Val Asn Gly Glu Asn Ile
    355                 360                 365

Glu Ala Pro Tyr Glu Phe Leu Leu Glu Lys Asp Thr Glu Val Thr Ala
    370                 375                 380

Leu Met Lys Lys Ser Asn Ala Val Gly Glu Val Asp Thr Lys Gly Phe
385                 390                 395                 400

His Val Tyr Pro Ile Pro Thr Ser Lys Asp Leu Thr Ile Glu Ile Pro
                405                 410                 415

Ala Glu Met Val Gly Lys Val Ala Ser Leu Ile Asp Met Asn Gly Gln
            420                 425                 430

Ile Val Tyr Arg Val Thr Leu Asn Asn Ile Phe Gln Gln Ile Asp Ile
        435                 440                 445

Ser His Leu Lys Gly Val Phe Leu Leu Gln Ile Gly Asp Ile Thr Glu
    450                 455                 460

Arg Val Ile Val Gln
465

<210> SEQ ID NO 2
<211> LENGTH: 1410
<212> TYPE: DNA
<213> ORGANISM: Porphyromonas gingivalis (strain W83; PG0495)

<400> SEQUENCE: 2
atgagaaaaa tcattatgaa aaacttttt ttggcctccg tggctttctt atgtgcatgg      60
atttggagcg ctaatgctca gacaatggct ccaaattact ccatgccga tccgcagcaa    120 ttcaaacaca ggattgtaaa agaaaaaagc ttctcctcct actctaatta cgaatacgga    180
gtcgacaacc gtctgcaaag gatctattcg gtggatgagt cttcgggaga gatcgaacac    240
gaaagacgat tcttttttcaa tgaaggcgga tatatgattc gtgaggagga atacgatgga    300
accgttcaga tacctgtcag aaaatgggaa tttgtccgcg atgacaaggg ttatatcact    360
catttcagca gatactcgcc taaagatgga agtcaggagt tgatagagga tatccgtatc    420
gatttttcct acgatgccga tatgaaactg atcaaagcgg atatagattt cttcgacatt    480
atggccaatg tatgggggcga tctgcgcacg acaaaactag tctataatga aaacggactc    540
```

-continued

```
ttgaaagaga tgattcaaac cgatccggga agtggacaag aattcaatcg ggaagagctt      600
acatacaata acctcaacaa aatagttgct atcaggttta taccgggacc ggccagtaca      660
ggtttgaacg aatttgaatt gatatacgaa tacgacagtg aaggaatgga tattgtcaaa      720
gccgggcgtg acgatttctg gtactactat gagtacgaca agaaatgct cgcttcagag       780
acattcttcc caaagccttc catagcagat ttagtatatt tcggacttaa agattatgtg      840
gattttcag gactacccctt caaaaacagt tatactcatg tagtagtcaa agaatctaca      900
aatgaagtgg aagcgattta tgaacctatc tctgtatatt ccgtagtggt catccagccc      960
gaaaatggag agataaagct aacggccgat gggcagcccc tgaacagcgg ttccacatta      1020
gtggcaggcc gtcgtattaa aatacatccc atccctgccg aaggttacga agtggacaag      1080
gtaatggtga acggagagaa tatcgaagct ccgtatgaat tccttcttga aaagatacga      1140
gaagtgacag ccctgatgaa aagagcaat gccgtaggag aagtcgacac caaaggcttc       1200
catgtctatc ccatacccac atcaaaagat ttgacgatag ataccggc agaaatggta       1260
ggcaaagtgg catctcttat agatatgaac ggacagattg tttacagagt tacgcttaat      1320
aacatcttcc agcagataga tatcagccat ctcaagggcg ttttcctctt gcagatcggt      1380
gatattacag aaagagtgat cgttcaataa                                       1410
```

<210> SEQ ID NO 3
<211> LENGTH: 248
<212> TYPE: PRT
<213> ORGANISM: Porphyromonas gingivalis (strain W83; PG2172)

<400> SEQUENCE: 3

```
Met Asn Lys Lys Thr Lys Arg Asn Met Arg Lys Ile Phe Ile Ser Ile
1               5                   10                  15

Ala Leu Leu Ala Gly Phe Ile Ala Ala Leu Asn Ala Gln Val Val Ile
                20                  25                  30

Lys Val Gly Asp Ala Ile Leu Glu Asn Asn Ala Thr Val Asp Ile Thr
            35                  40                  45

Ala Phe Thr Thr Glu Asp Gly Thr Glu Met Lys Phe Glu Gly Met
        50                  55                  60

Val Ile Asn Gln Ser Ala Thr Pro Ile Asn Val Ile Gly Lys Ile Thr
65                  70                  75                  80

Lys Gln Glu Met Ile Gly Asp Gly His Phe Ala Leu Cys Phe Gly Gln
                85                  90                  95

Cys Met Gly Pro Asn Val Ser Val Ser Pro Ile Val Glu Ala Leu Asp
                100                 105                 110

Gly Glu Gly Glu Tyr Val Ser Leu His Tyr Lys Phe Pro Val Ser Asn
            115                 120                 125

Glu Gly His Thr Gly Ala Phe Thr Phe Ser Cys Phe Pro Glu Ser Gly
        130                 135                 140

Ala Pro Gly Thr Glu Leu Ala Thr Val Asn Ile Asn Phe Lys Tyr Lys
145                 150                 155                 160

Gly Gly Gly Thr Gly Leu Thr Asn Ile Gly Leu Gly Arg Ile Ala Leu
                165                 170                 175

Ile Gln Ser Gly Asn Thr Cys Thr Leu Gln Tyr Asn Ser Asn Gly Lys
            180                 185                 190

Arg Leu Ala Leu Glu Val Tyr Asn Leu Gly Val Lys Val Phe Thr
        195                 200                 205

Ser Gln Leu Pro Ala Gly Ser Gly Ser Tyr Thr Leu Pro Val Arg Leu
    210                 215                 220
```

Gln Arg Gly Val His Ile Phe Arg Ile Thr Glu Gly Gly Lys Pro Ala
225                 230                 235                 240

Phe Val Gln Lys Tyr Leu Ile Lys
            245

<210> SEQ ID NO 4
<211> LENGTH: 747
<212> TYPE: DNA
<213> ORGANISM: Porphyromonas gingivalis (strain W83; PG2172)

<400> SEQUENCE: 4

```
atgaataaaa aaacaaaaag aaatatgagg aaaatcttta tcagcatcgc attgttggca      60
ggtttcattg ctgctctcaa tgcacaagtt gtgatcaagg tgggagatgc catcttggaa     120
aacaatgcca ctgtggacat tactgctttc acaacagaag atggtacgga agagatgaaa     180
tttgaaggaa tggttatcaa ccaatccgct acacctatca atgtaatcgg caagattacc     240
aagcaagaaa tgatcggtga tggacacttt gctttgtgct ttggtcagtg tatggggccg     300
aatgtatctg tatccccat  tgtggaggct cttgatggtg aaggagagta cgtctctttg     360
cattataaat ttcccgtgtc caatgaaggg catacgggag ctttcacttt tagctgcttc     420
cccgagagtg gtgctcccgg cacagaattg gctacagtga acattaactt caagtacaaa     480
ggcggtggaa ccggtttgac taatatcggg ctagggcgta tagctcttat ccagagcggt     540
aatacttgca cccttcagta acagcaat   ggcaagcgtc ttgcccttga agtgtacaat     600
ctcttaggcg taaaggtatt tacctctcag ctgcccgcag gatccggctc ttatacgctg     660
ccggtgcgtc tgcagcgtgg tgtgcatatc ttccgcatca cagaaggagg taagcctgcg     720
tttgttcaga gtatctgat  taagtaa                                         747
```

<210> SEQ ID NO 5
<211> LENGTH: 352
<212> TYPE: PRT
<213> ORGANISM: Porphyromonas gingivalis (strain W83; PG1326)

<400> SEQUENCE: 5

Met Cys Glu Asn Thr Leu Ala Gln Gln Lys Thr Glu Glu Phe Ala Pro
1               5                   10                  15

Val Ser Asp Leu Arg Ala Glu Ala Tyr Gly Ser Thr Val Phe Leu His
            20                  25                  30

Trp Thr Pro Pro Tyr Asp Asn Pro Met Ile Pro Leu Ser Glu Ser Phe
        35                  40                  45

Glu Ser Gly Ile Pro Ala Ile Trp Lys Thr Ile Asp Ala Asp Gly Asp
    50                  55                  60

Gly Tyr Asn Trp Met His Leu Thr Asn Phe Thr Gly Gln Ser Gly Leu
65                  70                  75                  80

Cys Val Ser Ser Ala Ser Tyr Ile Gly Gly Val Gly Ala Leu Thr Pro
                85                  90                  95

Asp Asn Tyr Leu Ile Thr Pro Glu Leu Lys Leu Pro Thr Asp Ala Leu
            100                 105                 110

Val Glu Ile Ile Tyr Trp Val Cys Thr Gln Asp Leu Thr Ala Pro Ser
        115                 120                 125

Glu His Tyr Ala Val Tyr Ser Ser Ser Thr Gly Asn Asn Ala Ala Asp
    130                 135                 140

Phe Val Asn Leu Leu Tyr Glu Glu Thr Leu Thr Ala Lys Arg Ile Gln
145                 150                 155                 160

Ser Pro Glu Leu Ile Arg Gly Asn Arg Thr Gln Gly Val Trp Tyr Gln
            165                 170                 175

Arg Lys Val Val Leu Pro Asn Asp Thr Lys Tyr Val Ala Phe Arg His
        180                 185                 190

Phe Asn Ser Thr Asp Asn Phe Trp Leu Asn Leu Asp Glu Val Ser Ile
            195                 200                 205

Leu Tyr Thr Pro Leu Pro Arg Arg Ala Pro Cys Pro His Pro Gly Gly
    210                 215                 220

Tyr Thr Tyr Ser Val Phe Arg Asp Gly Gln Lys Ile Ala Ser Gly Leu
225                 230                 235                 240

Ser Ala Leu Ala Tyr Ile Asp Thr Asp Val Pro Tyr Gly Thr Gln Asp
                245                 250                 255

Tyr Cys Val Gln Val Asn Tyr Leu Gln Gly Asp Ser Tyr Lys Val Cys
            260                 265                 270

Lys Asn Ile Val Val Ala Asn Ser Ala Asn Ile Tyr Gly Ala Asp Lys
        275                 280                 285

Pro Phe Ala Leu Thr Val Val Gly Lys Thr Ile Val Ala Ser Ala Phe
    290                 295                 300

Lys Gly Glu Ile Thr Leu Tyr Asp Ile Arg Gly Arg Leu Ile Ala Ser
305                 310                 315                 320

Gly Cys Asp Thr Leu Arg Tyr Lys Ala Glu Asn Gly Phe Tyr Leu Ile
                325                 330                 335

Lys Ile Gln Val Asn Gly Thr Val Tyr Thr Glu Lys Ile Gln Ile Gln
            340                 345                 350

<210> SEQ ID NO 6
<211> LENGTH: 1059
<212> TYPE: DNA
<213> ORGANISM: Porphyromonas gingivalis (strain W83; PG1326)

<400> SEQUENCE: 6
ttgtgtgaaa ataccccttgc acaacaaaaa acagaggagt tgcacctgt gtcggattta      60 cgtgcagaag cgtacggctc taccgttttc ctccactgga ctccgccgta tgacaatccg     120
atgattcctc taagcgagag ttttgaatca ggtattccag ctatatggaa gaccattgac     180
gcagatggcg atggctataa ttggatgcat ttgaccaatt tcacgggaca gagtggtctc     240
tgtgtctctt cggcttcata cataggcggc gtcggagctt tgactccgga caattatctg     300
ataacacccg aattaaaact acccacagac gcgttggtgg aaataatcta ttgggtatgt     360
actcaagatc tcactgctcc atcggagcac tatgccgttt attcctcttc tacaggcaat     420
aatgctgctg actttgttaa tctcttatat gaagagactt tgactgccaa acggatacaa     480
tcccccgagt tgatccgcgg aaatcggaca caaggtgttt ggtatcaaag aaaggtggta     540
ctccctaacg atactaaata tgttgctttc cgccatttta attccacgga taatttctgg     600
ctcaatttgg atgaagtatc tatcctgtat ccccctcttc cccgaagagc tccgtgtccg     660
catccgggtg gttacactta ttctgtattc cgtgatggac aaaagatagc gagtggattg     720
tcggcattgg catatatcga tacggatgta ccgtatggga ctcaagacta ttgtgtccaa     780
gtcaattatc tgcaaggaga ctcgtataaa gtctgcaaaa atatagtggt ggcaaattct     840
gcaaacatct atgggcggaa taagcctttt gcgttgaccg tggttggcaa gaccattgta     900
gcgagtgctt tcaaaggaga gatcactctt tatgacattc gtggccggct gatagcttcc     960
ggctgcgata cgcttaggta caaagcggaa aatggttttt acctcattaa aatacaggta    1020
aacggaactg tctatactga gaaaatccaa atccaatag                           1059

<210> SEQ ID NO 7
<211> LENGTH: 428
<212> TYPE: PRT
<213> ORGANISM: Porphyromonas gingivalis (strain W83; PG1374)

<400> SEQUENCE: 7

Met Lys Leu Ser Ser Lys Lys Ile Leu Ala Ile Ile Ala Leu Leu Thr
1               5                   10                  15

Met Gly His Ala Val Gln Ala Gln Phe Val Pro Ala Pro Thr Thr Gly
            20                  25                  30

Ile Arg Met Ser Val Thr Thr Thr Lys Ala Val Gly Glu Lys Ile Glu
        35                  40                  45

Leu Leu Val His Ser Ile Glu Lys Lys Gly Ile Trp Ile Asp Leu Asn
    50                  55                  60

Gly Asp Ala Thr Tyr Gln Gln Gly Glu Glu Ile Thr Val Phe Asp Glu
65                  70                  75                  80

Ala Tyr His Glu Tyr Thr Ile Gly Thr Gln Thr Leu Thr Ile Tyr Gly
                85                  90                  95

Asn Thr Thr Arg Leu Gly Cys Arg Ser Thr Gly Ala Thr Ala Val Asp
            100                 105                 110

Val Thr Lys Asn Pro Asn Leu Thr Tyr Leu Ala Cys Pro Lys Asn Asn
        115                 120                 125

Leu Lys Ser Leu Asp Leu Thr Gln Asn Pro Lys Leu Leu Arg Val Trp
    130                 135                 140

Cys Asp Ser Asn Glu Ile Glu Ser Leu Asp Leu Ser Gly Asn Pro Ala
145                 150                 155                 160

Leu Ile Ile Leu Gly Cys Asp Arg Asn Lys Leu Thr Glu Leu Lys Thr
                165                 170                 175

Asp Asn Asn Pro Lys Leu Ala Ser Leu Trp Cys Ser Asp Asn Asn Leu
            180                 185                 190

Thr Glu Leu Glu Leu Ser Ala Asn Pro Arg Leu Asn Asp Leu Trp Cys
        195                 200                 205

Phe Gly Asn Arg Ile Thr Lys Leu Asp Leu Ser Ala Asn Pro Leu Leu
    210                 215                 220

Val Thr Leu Trp Cys Ser Asp Asn Glu Leu Ser Thr Leu Asp Leu Ser
225                 230                 235                 240

Lys Asn Ser Asp Val Ala Tyr Leu Trp Cys Ser Ser Asn Lys Leu Thr
                245                 250                 255

Ser Leu Asn Leu Ser Gly Val Lys Gly Leu Ser Val Leu Val Cys His
            260                 265                 270

Ser Asn Gln Ile Ala Gly Glu Glu Met Thr Lys Val Val Asn Ala Leu
        275                 280                 285

Pro Thr Leu Ser Pro Gly Ala Gly Gln Ser Lys Phe Val Val Val
    290                 295                 300

Asp Leu Lys Asp Thr Asp Glu Lys Asn Ile Cys Thr Val Lys Asp Val
305                 310                 315                 320

Glu Lys Ala Lys Ser Lys Asn Trp Arg Val Phe Asp Phe Asn Gly Asp
                325                 330                 335

Ser Asp Asn Met Leu Pro Tyr Glu Gly Ser Pro Thr Ser Asn Leu Ala
            340                 345                 350

Val Asp Ala Pro Thr Val Arg Ile Tyr Pro Asn Pro Val Gly Arg Tyr
        355                 360                 365

Ala Leu Val Glu Ile Pro Glu Ser Leu Leu Gly Gln Glu Ala Ala Leu

```
            370             375             380
Tyr Asp Met Asn Gly Val Lys Val Tyr Ser Phe Ala Val Glu Ser Leu
385                 390                 395                 400

Arg Gln Asn Ile Asp Leu Thr His Leu Pro Asp Gly Thr Tyr Phe Phe
                405                 410                 415

Arg Leu Asp Asn Tyr Thr Thr Lys Leu Ile Lys Gln
            420                 425
```

<210> SEQ ID NO 8
<211> LENGTH: 1287
<212> TYPE: DNA
<213> ORGANISM: Porphyromonas gingivalis (strain W83; PG1374)

<400> SEQUENCE: 8

```
atgaaacttt catctaagaa aatcttagca atcattgcat tgctgacgat gggacatgct    60
gtgcaggcac agtttgttcc ggctcccacc acagggattc gcatgtctgt cactacaacc   120
aaggccgtag cgaaaaaaat cgaattgttg gttcattcca tagagaagaa aggcatctgg   180
atcgatctca atggggatgc cacttaccaa caaggagagg aaataaccgt attcgatgag   240
gcataccacg aatacacgat cgggacgcaa accctcacta tctatggtaa tacgacccga   300
ttgggctgtc gatctaccgg tgcaacggct gtcgatgtaa cgaaaaaccc taatctgacc   360
tatctcgcat gcccgaaaaa taatctgaaa tcattggact tgacgcaaaa cccaaagctg   420
ctgcgagttt ggtgcgactc taacgaaata gaaagtttgg acctgagtgg caatccggct   480
ttgatcatcc tcggctgtga caggaataag ctgactgagc tgaagaccga taacaacccc   540
aagttggcct ctctttggtg ttctgataat aacctgacgg agttggaact cagtgccaat   600
cctcgtctca tgatctttg gtgcttcggt aatcggatca cgaaactcga tctgagtgcc   660
aatcctctat ggtaacact tggtgcagt gacaatgagc tttcgacctt ggatcttttcc   720
aagaattcgg acgttgctta cctttggtgt tcatcgaaca aacttacatc cttgaatctg   780
tcggggtga agggactgag tgttttggtt tgtcattcca atcagatcgc aggtgaagaa   840
atgacgaaag tggtgaatgc tttgcccaca ctatctcccg gcgcaggcgc tcagagcaag   900
ttcgtcgttg tagacctcaa ggacactgat gagaagaata tctgtaccgt aaaggatgtg   960
gaaaaagcta aaagtaagaa ctggcgagta tttgacttca cggtgattc tgacaatatg  1020
cttccatacg aaggaagtcc gacatcgaac ttggcagtag atgctccac tgtcaggata  1080
tatcccaatc cggtaggaag atatgcgctc gtcgagatcc ccgagtctct tttagggcag  1140
gaagctgctt tatacgatat gaatggggta aaagtctata gtttcgcggt agagtctctt  1200
cgtcagaaca ttgacctgac acatcttccc gacggcactt atttcttccg tctcgataac  1260
tataccacta agctcatcaa acagtag                                      1287
```

<210> SEQ ID NO 9
<211> LENGTH: 390
<212> TYPE: PRT
<213> ORGANISM: Porphyromonas gingivalis (strain W83; PG0654)

<400> SEQUENCE: 9

```
Met Lys Arg Leu Leu Pro Phe Leu Leu Leu Ala Gly Leu Val Ala Val
1               5                   10                  15

Gly Asn Val Ser Ala Gln Ser Pro Arg Ile Pro Gln Val Asp Val His
                20                  25                  30

Thr Arg Ile Ala Arg Asn Ala Arg Tyr Arg Leu Asp Lys Ile Ser Val
            35                  40                  45
```

| | | | | | | | | | | | | |
|---|---|---|---|---|---|---|---|---|---|---|---|---|
| Pro | Asp | Ser | Arg | Gln | Ile | Phe | Asp | Tyr | Phe | Tyr | Lys | Glu | Thr | Ile |
| | 50 | | | | 55 | | | | | 60 | | | | |

Pro Asp Ser Arg Gln Ile Phe Asp Tyr Phe Tyr Lys Glu Thr Ile
    50                    55                    60

Pro Thr Lys Ile Gln Thr Thr Thr Gly Gly Ala Ile Thr Ser Ile Asp
65                    70                    75                    80

Ser Leu Phe Tyr Glu Asp Asp Arg Leu Val Gln Val Arg Tyr Phe Asp
                85                    90                    95

Asn Asn Leu Glu Leu Lys Gln Ala Glu Lys Tyr Val Tyr Asp Gly Ser
            100                    105                  110

Lys Leu Val Leu Arg Glu Ile Arg Lys Ser Pro Thr Asp Glu Thr Pro
          115                  120                125

Ile Lys Lys Val Ser Tyr His Tyr Leu Cys Gly Ser Asp Met Pro Phe
      130                    135                  140

Glu Ile Thr Thr Glu Met Ser Asp Gly Tyr Phe Glu Ser His Thr Leu
145                    150                    155            160

Asn Tyr Leu Asn Gly Lys Ile Ala Arg Ile Asp Ile Met Thr Gln Gln
                165                    170                175

Asn Pro Ser Ala Glu Leu Ile Glu Thr Gly Arg Met Val Tyr Glu Phe
            180                    185                  190

Asp Ala Asn Asn Asp Ala Val Leu Leu Arg Asp Ser Val Phe Leu Pro
          195                  200                205

Leu Gln Asn Lys Trp Val Glu Met Phe Thr His Arg Tyr Thr Tyr Asp
    210                    215                  220

Asn Lys His Asn Cys Ile Arg Trp Glu Gln Asp Glu Phe Gly Thr Leu
225                    230                    235            240

Thr Leu Ala Asn Asn Phe Glu Tyr Asp Thr Thr Ile Pro Leu Ser Ser
                245                    250                255

Val Leu Phe Pro Thr His Glu Glu Phe Phe Arg Pro Leu Leu Pro Asn
            260                    265                270

Phe Met Lys His Met Arg Thr Lys Gln Thr Tyr Phe Asn Asn Ser Gly
      275                    280                  285

Glu Gly Leu Ser Glu Val Cys Asp Tyr Asn Tyr Phe Tyr Thr Asp Met
    290                    295                  300

Gln Gly Asn Ala Leu Thr Asp Val Ala Val Asn Glu Ser Ile Lys Ile
305                    310                    315            320

Tyr Pro Arg Pro Ala Thr Asp Phe Leu Arg Ile Glu Gly Ser Gln Leu
                325                    330                335

Leu Arg Leu Ser Leu Phe Asp Met Asn Gly Lys Leu Ile Arg Ala Thr
            340                    345                350

Glu Leu Thr Gly Asp Leu Ala Ile Ile Gly Val Ala Ser Leu Pro Arg
      355                    360                  365

Gly Thr Tyr Ile Ala Glu Ile Thr Ala Ala Asn Ser Lys Thr Ile Arg
    370                    375                  380

Ala Lys Val Ser Leu Arg
385                    390

<210> SEQ ID NO 10
<211> LENGTH: 1173
<212> TYPE: DNA
<213> ORGANISM: Porphyromonas gingivalis (strain W83; PG0654)

<400> SEQUENCE: 10
atgaaacgat tactccccctt tctccttttta gcaggactcg tagccgtagg aaacgtgtct    60
gctcagtcac cccgaatccc tcaagtggat gtacacactc gcatcgcaag aaatgcccgt    120

```
tatcgactgg acaagatcag tgtcccggat tctcgtcaga tattcgatta cttctataaa    180
gaagaaacga tacccactaa aatacaaacg accacaggag gtgcaattac aagcatcgat    240
tcgcttttct atgaagacga caggttggtt caggtgcgct attttgacaa taaccttgaa    300
ttaaaacaag cggagaagta tgtatacgac ggttctaagc tggtccttcg agaaattcgc    360
aagtcgccga cagacgaaac gccaataaag aaagttagct atcactatct ctgtggcagc    420
gatatgcctt ttgagattac gacagagatg agcgatggct attttgaaag ccatacgctt    480
aactatctga atggaaagat tgcccgaata gatatcatga ctcaacagaa cccatcggcc    540
gaattgatcg aaacgggtag aatggtatat gagtttgatg ccaataatga tgctgtactg    600
cttcgtgaca gtgtatttct tcctcttcaa aacaagtggg tagaaatgtt tactcaccgt    660
tatacatacg acaataagca taattgtatt cgttgggaac aagacgaatt cggcaccctc    720
acccttgcca acaacttcga atacgacacc actatccctc tgtcgtctgt attgttcccc    780
acgcatgagg agttcttccg tcctcttctt cccaatttta tgaagcatat gcgtacgaag    840
caaacgtatt tcaataactc cggagaaggc ttgtcagagg tatgcgatta caactacttc    900
tataccgata tgcagggtaa tgcactgacc gatgttgccg tgaacgaatc gatcaagatt    960
tatcctcgtc ctgccacgga ttttctgcgt atagaaggtt cgcaactgct tcgccttcg   1020
ctattcgaca tgaacgggaa gctcatcaga gctaccgaat tgacaggcga tttggccatt   1080
atcggagttg catctcttcc gagaggcact tacatcgcag aaataactgc tgcaaacagc   1140
aaaaccatac gtgcaaaagt atcgctcaga taa                                1173
```

<210> SEQ ID NO 11
<211> LENGTH: 229
<212> TYPE: PRT
<213> ORGANISM: Porphyromonas gingivalis (strain W83; PG0613)

<400> SEQUENCE: 11

```
Met Met Lys Lys Ala Phe Val Phe Val Leu Leu Val Cys Leu Phe Ser
1               5                   10                  15

Ser Phe Ser Ser Ser Ala Gln Thr Thr Thr Asn Ser Ser Arg Ser Tyr
            20                  25                  30

Phe Thr Gly Arg Ile Glu Lys Val Ser Leu Asn Leu Gly Val Pro Pro
        35                  40                  45

Val Ser Thr Glu Val Trp Gly Met Thr His Asp Ala Asn Gly Leu Pro
    50                  55                  60

Phe Glu Ile Pro Ile Ser Phe Ser Arg Phe Asn Ser Gln Gly Asp Ile
65                  70                  75                  80

Ala Thr Thr Tyr Tyr Ile Ala Asn Ser Glu Ala Thr Leu Asn Glu Trp
                85                  90                  95

Cys Asp Tyr Ala His Pro Gly Gly Ile Val Arg Val Glu Gly Arg Phe
            100                 105                 110

Trp Lys Met Thr Tyr Asn Ile Pro Thr Tyr Asn Ala Val Cys Thr Arg
        115                 120                 125

Ile Thr Phe Glu Asn Gln Glu Ile Glu Gly Thr Ile Val Leu Ile Pro
    130                 135                 140

Lys Pro Lys Val Ser Leu Pro His Val Ser Glu Ser Val Pro Cys Ile
145                 150                 155                 160

Arg Thr Glu Ala Gly Arg Glu Phe Ile Leu Cys Glu Glu Asp Asp Thr
                165                 170                 175

Phe Val Ser His Asp Gly Asn Glu Val Thr Ile Gly Gly Lys Pro Phe
            180                 185                 190
```

Leu Leu Asn Thr Asn Val Lys Ile Val Gly Asp Val Ser Gln Lys Tyr
        195                 200                 205

Ala Val Gly Val Gly Glu Ile Arg Phe Leu Gln Ile Cys Ala Gln Thr
    210                 215                 220

Val Ser Gln Gln Lys
225

<210> SEQ ID NO 12
<211> LENGTH: 690
<212> TYPE: DNA
<213> ORGANISM: Porphyromonas gingivalis (strain W83; PG0613)

<400> SEQUENCE: 12

```
atgatgaaaa aagcatttgt tttcgtacta ctggtttgcc tattctcctc gttcagcagt      60
tccgcccaaa caacgacgaa cagtagccgg agttatttta caggacgaat cgagaaggtg     120
agtttgaact tagggtccc ccccgtaagc acagaggttt ggggaatgac ccatgatgcg     180
aacggtctcc ctttcgaaat acctatctct ttcagtcgtt tcaacagcca gggagatata     240
gctaccactt attacatagc gaatagcgag gcaactttga atgaatggtg cgactatgca     300
cacccgggcg gcatcgtgag ggtagaaggt cgttttttgga aaatgactta caacatacca     360
acctacaatg cagtctgcac ccggattaca ttcgaaaatc aagaaataga aggaacgatc     420
gtcttgatac ccaagcccaa agtctcgctg cctcatgtgt cggaatcggt gccttgcatc     480
cgaaccgaag ccgggaggga atttatcctt tgcgaagaag acgacacctt gtgtctcac     540
gatggtaacg aagtaacgat aggcggtaaa cctttcttgc tcaataccaa cgtaaagatt     600
gtggggacg tatctcaaaa gtatgccgtg ggggtaggag aaattcgatt cctgcagatt     660
tgtgcccaaa cagtatcaca acaaaaatga                                      690
```

<210> SEQ ID NO 13
<211> LENGTH: 405
<212> TYPE: PRT
<213> ORGANISM: Porphyromonas gingivalis (strain W83; PG1798)

<400> SEQUENCE: 13

Met Lys Lys Thr Thr Ile Ile Ser Leu Ile Val Phe Gly Ala Phe Phe
1               5                   10                  15

Ala Ala Val Gly Gln Thr Lys Asp Asn Ser Ser Tyr Lys Pro Phe Ser
            20                  25                  30

Lys Glu Asp Ile Ala Gly Gly Val Tyr Ser Leu Pro Thr Gln Asn Arg
        35                  40                  45

Ala Gln Lys Asp Asn Ala Glu Trp Leu Leu Thr Ala Thr Val Ser Thr
    50                  55                  60

Asn Gln Ser Ala Asp Thr His Phe Ile Phe Asp Glu Asn Asn Arg Tyr
65                  70                  75                  80

Ile Ala Arg Asp Ile Lys Ala Asn Gly Val Arg Lys Ser Thr Asp Ser
                85                  90                  95

Ile Tyr Tyr Asp Ala Asn Gly Arg Ile Ser His Val Asp Leu Tyr Ile
            100                 105                 110

Ser Phe Ser Gly Gly Glu Pro Ala Leu Asp Thr Arg Phe Lys Tyr Thr
        115                 120                 125

Tyr Asp Asp Glu Gly Lys Met Thr Val Arg Glu Val Phe Met Leu Val
    130                 135                 140

Met Asp Pro Asn Thr Pro Ile Ser Arg Leu Glu Tyr His Tyr Asp Ala
145                 150                 155                 160

```
Gln Gly Arg Leu Thr His Trp Ile Ser Phe Ala Phe Gly Ala Glu Ser
            165                 170                 175

Gln Lys Asn Thr Tyr His Tyr Asn Glu Lys Gly Leu Leu Val Ser Glu
        180                 185                 190

Val Leu Ser Asn Ala Met Gly Thr Thr Tyr Ser Asp Thr Gly Lys Thr
    195                 200                 205

Glu Tyr Ser Tyr Asp Asp Ala Asp Asn Met Val Lys Ala Glu Tyr Phe
210                 215                 220

Val Val Gln Gln Gly Lys Ala Trp Gln Val Leu Lys Arg Glu Glu Tyr
225                 230                 235                 240

Thr Tyr Glu Asp Asn Ile Cys Ile Gln Tyr Leu Ala Ile Asn Gly Thr
            245                 250                 255

Asp Thr Lys Val Tyr Lys Arg Asp Ile Glu Ser Asp Lys Ser Ile Ser
        260                 265                 270

Ala Asn Val Ile Asp Ile Pro Ser Met Pro Glu Gln Thr Trp Pro Asn
    275                 280                 285

Met Tyr Gly Phe Asn Ala Lys Arg Leu Lys Glu Thr Tyr Ser Ser Tyr
290                 295                 300

Glu Gly Asp Val Ala Thr Pro Ile Phe Asp Tyr Ile Tyr Thr Tyr Lys
305                 310                 315                 320

Ala Leu Thr Ser Met Ala Thr Pro Ser Thr Glu Ala Gln Val Ala Val
            325                 330                 335

Tyr Leu Asn Pro Ser Thr Asp Arg Leu Val Ile Leu Ala Asn Gly Ile
        340                 345                 350

Thr His Leu Ser Met Tyr Asp Leu Gln Gly Lys Leu Ile Arg Asp Cys
    355                 360                 365

Ala Leu Ser Gly Asp Lys Val Glu Met Gly Val Gly Ser Leu Thr Lys
370                 375                 380

Gly Thr Tyr Leu Leu Lys Val Asn Thr Asp Gln Gly Ala Phe Val Arg
385                 390                 395                 400

Lys Val Val Ile Arg
            405

<210> SEQ ID NO 14
<211> LENGTH: 1218
<212> TYPE: DNA
<213> ORGANISM: Porphyromonas gingivalis (strain W83; PG1798)

<400> SEQUENCE: 14
atgaaaaaaa caaccattat ttctttgatt gtcttcggtg ctttctttgc agccgtgggc      60
caaaccaagg acaattcttc ttacaaacct ttttcgaaag aagatattgc cggaggagtt     120
tactctctcc cgactcaaaa tcgtgcgcag aaggacaatg ccgagtggct tcttacagcg     180
accgtctcca caaccagtc tgcagatact cactttatct tcgatgagaa caaccgctat      240
atcgctcgtg acataaaagc caatggggta agaaaatcca cggactccat ttactacgat     300
gccaacgggc gaatatcgca tgtggatctt tatatctcgt tcagtggcgg agagcctgca     360
ctcgacaccc gattcaagta cacctatgat gacgagggaa agatgaccgt gagggaagta     420
ttcatgctgg taatggatcc gaatacacct atctcacgct ggaatatca ttatgatgca      480 cagggcagac tgacccactg gatttctttt gctttcgggg cagaatccca aagaatacg      540 tatcactata tgaaaaagg tctgttggtc agcgaagtgc tgagcaatgc aatggggaca     600
acctattcag acaccggcaa aacggaatac agctatgacg atgcagataa tatggtgaag     660
```

-continued

```
gccgagtact tcgtcgtcca gcaaggaaag gcatggcaag tactcaaaag agaggaatac    720
acctatgagg acaatatctg catacaatat ttggctatta acggtaccga cacaaaggtg    780
tacaagcgag acatcgagag cgataagtcc atctccgcaa atgtcattga cattccgtca    840
atgccggaac agacctggcc taatatgtac ggattcaacg caaagcgact gaaagagact    900
tattcctcct acgaaggaga tgtggctact cctatattcg actatatcta tacgtacaag    960
gctcttacct caatggcaac accttcgaca gaagctcagg tagcagtcta tctcaatccg   1020
tcaacggacc ggttagtgat tctggccaac ggcatcacac atctgagcat gtacgacttg   1080
cagggtaagc ttatccgtga ttgtgccttg agcggcgata aggtgaaat gggtgtcgga   1140 tctttgacca aagggacata cctgcttaaa gtgaatacgg atcagggagc ctttgtgaga   1200
aaagtcgtga ttcgatga                                                 1218
```

<210> SEQ ID NO 15
<211> LENGTH: 501
<212> TYPE: PRT
<213> ORGANISM: Porphyromonas gingivalis (strain W83; PG0186)

<400> SEQUENCE: 15

Met Lys Lys Ile Ile Tyr Trp Val Ala Thr Val Phe Leu Ala Ala Ser
1               5                   10                  15

Val Ser Ser Cys Glu Leu Asp Arg Asp Pro Glu Gly Lys Asp Phe Gln
            20                  25                  30

Gln Pro Tyr Thr Ser Phe Val Gln Thr Lys Gln Asn Arg Asp Gly Leu
        35                  40                  45

Tyr Ala Leu Leu Arg Asn Thr Glu Asn Pro Arg Met His Phe Tyr Gln
    50                  55                  60

Glu Leu Gln Ser Asp Met Tyr Cys Thr Thr Ile Thr Asp Gly Asn Ser
65                  70                  75                  80

Leu Ala Pro Phe Val Asn Trp Asp Leu Gly Ile Leu Asn Asp His Gly
                85                  90                  95

Arg Ala Asp Glu Asp Glu Val Ser Gly Ile Ala Gly Tyr Tyr Phe Val
            100                 105                 110

Tyr Asn Arg Leu Asn Gln Gln Ala Asn Ala Phe Val Asn Asn Thr Glu
        115                 120                 125

Ala Ala Leu Gln Asn Gln Val Tyr Lys Asn Ser Thr Glu Ile Ala Asn
    130                 135                 140

Ala Lys Ser Phe Leu Ala Glu Gly Lys Val Leu Gln Ala Leu Ala Ile
145                 150                 155                 160

Trp Arg Leu Met Asp Arg Phe Ser Phe His Glu Ser Val Thr Glu Val
                165                 170                 175

Asn Ser Gly Ala Lys Asp Leu Gly Val Ile Leu Leu Lys Glu Tyr Asn
            180                 185                 190

Pro Gly Tyr Ile Gly Pro Arg Ala Thr Lys Ala Gln Cys Tyr Asp Tyr
        195                 200                 205

Ile Leu Ser Arg Leu Ser Glu Ala Ile Glu Val Leu Pro Glu Asn Arg
    210                 215                 220

Glu Ser Val Leu Tyr Val Ser Arg Asp Tyr Ala Tyr Ala Leu Arg Ala
225                 230                 235                 240

Arg Ile Tyr Leu Ala Leu Gly Glu Tyr Gly Lys Ala Ala Ala Asp Ala
                245                 250                 255

Lys Met Val Val Asp Lys Tyr Pro Leu Ile Gly Ala Ala Asp Ala Ser
            260                 265                 270

```
Glu Phe Glu Asn Ile Tyr Arg Ser Asp Ala Asn Asn Pro Glu Ile Ile
            275                 280                 285

Phe Arg Gly Phe Ala Ser Ala Thr Leu Gly Ser Phe Thr Ala Thr Thr
        290                 295                 300

Leu Asn Gly Ala Ala Pro Ala Gly Lys Asp Ile Lys Tyr Asn Pro Ser
305                 310                 315                 320

Ala Val Pro Phe Gln Trp Val Val Asp Leu Tyr Glu Asn Glu Asp Phe
                325                 330                 335

Arg Lys Ser Val Tyr Ile Ala Lys Val Lys Lys Asp Lys Gly Tyr
            340                 345                 350

Leu Val Asn Lys Phe Leu Glu Asp Lys Ala Tyr Arg Asp Val Gln Asp
            355                 360                 365

Lys Pro Asn Leu Lys Val Gly Ala Arg Tyr Phe Ser Val Ala Glu Val
        370                 375                 380

Tyr Leu Ile Leu Val Glu Ser Ala Leu Gln Thr Gly Asp Thr Pro Thr
385                 390                 395                 400

Ala Glu Lys Tyr Leu Lys Ala Leu Ser Lys Ala Arg Gly Ala Glu Val
                405                 410                 415

Ser Val Val Asn Met Glu Ala Leu Gln Ala Glu Arg Thr Arg Glu Leu
            420                 425                 430

Ile Gly Glu Gly Ser Arg Leu Arg Asp Met Val Arg Trp Ser Ile Pro
        435                 440                 445

Asn Asn His Asp Ala Phe Glu Thr Gln Pro Gly Leu Glu Gly Phe Ala
450                 455                 460

Asn Thr Thr Pro Leu Lys Ala Gln Ala Pro Val Gly Phe Tyr Ala Tyr
465                 470                 475                 480

Thr Trp Glu Phe Pro Gln Arg Asp Arg Gln Thr Asn Pro Gln Leu Ile
                485                 490                 495

Lys Asn Trp Pro Ile
            500

<210> SEQ ID NO 16
<211> LENGTH: 1506
<212> TYPE: DNA
<213> ORGANISM: Porphyromonas gingivalis (strain W83; PG0186)

<400> SEQUENCE: 16
atgaaaaaaa taatttattg ggttgcgaca gttttcttag cagcgagcgt atcctcttgc       60
gagcttgacc gcgaccccga aggaaaagat ttccaacagc catatacttc tttcgtgcag      120
acgaaacaaa acagagatgg tctttacgca cttttgcgta atactgaaaa tccacgaatg      180 cattttatc aggaacttca atccgatatg tattgcacta ccattactga tggtaactcc       240
ttagctccgt tcgtgaattg ggatttaggc atacttaacg accatggacg tgctgatgag      300
gacgaagtct ccggtatagc tggctactat ttcgtataca atcgactaaa tcagcaagcg      360
aatgcttttg ttaacaatac ggaagctgcg ttgcagaatc aagtgtataa aaattccacc      420
gagatcgcca atgctaagag cttttggcg gaaggaaaag ttttacaagc attggctatt      480
tggcgactga tggatcgttt tagcttccat gaaagcgtga cagaagttaa ttccggtgcg      540
aaagatcttg gcgttattct gttgaaagaa tataatcctg ttatatcgg tccccgtgca      600 acgaaggcac aatgttatga ttacattttg tcacgtttgt ctgaggctat tgaagttttg      660
cccgaaaaca gggaaagcgt tctttatgtg agccgtgatt acgcctatgc cctccgagca      720
agaatttacc tcgcgttggg tgaatatgga aaagctgcag cagatgctaa gatggttgtt      780
```

-continued

```
gataagtatc ctttgattgg tgcagcagat gcttctgagt ttgagaatat ttatcgatca    840
gatgctaata atcccgaaat tatttttcgt ggttttgctt ctgcgactct tggctcgttt    900
actgctacga cactaaatgg tgctgcgcca gcaggtaagg atataaaata taatccgagc    960
gcagtccctt tccaatgggt agtggatctt tatgaaaacg aagatttccg caaatccgta   1020
tatatcgcga aagttgtgaa aaaggataag gggtatttag taaataaatt ccttgaggac   1080
aaggcttatc gtgatgttca ggataagcca aaccttaaag tcggagctcg ttattttagc   1140
gttgctgagg tctacttaat tttggtagag tctgctcttc agactggaga taccccaaca   1200
gccgaaaaat atctcaaggc tttgagtaaa gctcgtggag cagaagtttc agtcgttaat   1260
atggaagcac tgcaagcaga gcgtacgcgt gagcttatag gtgagggtag tcgtttgcgt   1320
gatatggtcc gctggagtat ccctaataat catgatgctt ttgagactca gcctggttta   1380
gaaggttttg caaatactac tcctttgaaa gctcaagctc ctgtaggctt ttatgcatat   1440
acttgggagt tcccacagcg agatcgacaa actaatccgc agttaataaa gaactggccg   1500
atataa                                                              1506
```

<210> SEQ ID NO 17
<211> LENGTH: 273
<212> TYPE: PRT
<213> ORGANISM: Porphyromonas gingivalis (strain W83; PG1795)

<400> SEQUENCE: 17

```
Met Lys Lys Ala Leu Leu Ile Gly Ala Ala Leu Leu Gly Ala Val Ser
1               5                   10                  15

Phe Ala Ser Ala Gln Ser Leu Ser Thr Ile Lys Val Gln Asn Asn Ser
            20                  25                  30

Val Gln Gln Pro Arg Glu Glu Ala Thr Ile Gln Val Cys Gly Glu Leu
        35                  40                  45

Ala Glu Gln Val Asp Cys Ile Gly Thr Gly Asn Ser Ala Ile Ile Ala
    50                  55                  60

Ala Ala Ala Lys Phe Glu Ser Asp Asp Leu Glu Ser Tyr Val Gly Trp
65                  70                  75                  80

Glu Ile Met Ser Val Asp Phe Phe Pro Gly Tyr Lys Ala Cys Lys Tyr
                85                  90                  95

Thr Ser Ala Val Trp Ala Asp Asp Met Thr Ile Leu Gly Gln Ser Glu
            100                 105                 110

Asp Ser Asp Pro Glu Met Gln Thr Ile Asn Asn Leu Ala Leu Lys Thr
        115                 120                 125

Ser Val Lys Ile Glu Ala Gly Lys Asn Tyr Ile Val Gly Tyr Ile Ala
    130                 135                 140

Asn Thr Ala Gly Gly His Pro Ile Gly Cys Asp Gln Gly Pro Ala Val
145                 150                 155                 160

Asp Gly Tyr Gly Asp Leu Val Ser Ile Ser Glu Asp Gly Gly Ala Thr
                165                 170                 175

Phe Pro Pro Phe Glu Ser Leu His Gln Ala Val Pro Thr Leu Asn Tyr
            180                 185                 190

Asn Ile Tyr Val Val His Leu Lys Lys Gly Glu Gly Val Glu Ala
        195                 200                 205

Val Leu Thr Asn Asp Lys Ala Asn Ala Tyr Val Gln Asn Gly Val Ile
    210                 215                 220

Tyr Val Ala Gly Ala Asn Gly Arg Gln Val Ser Leu Phe Asp Met Asn
225                 230                 235                 240
```

Gly Lys Val Val Tyr Thr Gly Val Ser Glu Thr Ile Ala Ala Pro Gln
                245                 250                 255

Lys Gly Met Tyr Ile Leu Arg Val Gly Ala Lys Ser Ile Lys Leu Ala
            260                 265                 270

Ile

<210> SEQ ID NO 18
<211> LENGTH: 822
<212> TYPE: DNA
<213> ORGANISM: Porphyromonas gingivalis (strain W83; PG1795)

<400> SEQUENCE: 18
atgaaaaaag cattacttat tggtgctgct cttttgggag cagtcagttt tgcaagtgct    60
cagtctttga gcacaatcaa agtacagaac aattcagtac agcaacctcg tgaggaagcc   120
actattcagg tttgtggaga attggcagag caagttgact gcattgggac aggtaattct   180
gcaatcatag ccgctgcagc gaaatttgaa agcgatgatc tcgaaagcta tgttggctgg   240
gagatcatga gtgttgattt cttccctgga tataaagcgt gcaagtacac atctgcagtc   300
tgggctgatg atatgaccat tttgggccaa tcagaagata gtgatcccga aatgcagact   360
atcaacaatc ttgctctcaa gactagtgtc aagattgaag ccggcaagaa ttacatagtt   420
ggttatattg ctaataccgc aggtggacat cctatcggat gtgatcaggg ccctgccgtt   480
gatggttatg agagatttgg ttctatatca aagatggtg tgctactttt ccctccgttc    540
gaatctcttc atcaagcagt tcctaccta aattacaaca tctatgtcgt tgttcatttg    600
aagaagggtg aaggtgttga ggctgttctt accaacgaca aggctaatgc ttatgttcag   660
aatggcgtta tctatgtagc cggagctaat ggtcgtcagg tatctctgtt cgacatgaac   720
ggtaaggttt tttataccgg cgttagcgaa acgattgcag ctcctcagaa gggcatgtat   780
atcctccgtg taggtgctaa gagcatcaag ctggctatct aa                      822

<210> SEQ ID NO 19
<211> LENGTH: 344
<212> TYPE: PRT
<213> ORGANISM: Porphyromonas gingivalis (strain W83; PG0616)

<400> SEQUENCE: 19

Met Lys Arg Leu Leu Leu Ser Ala Ala Ile Leu Ser Ser Met Ala Leu
1               5                   10                  15

Phe Asn Val Asn Ala Gln Glu Leu Lys Thr Ser Ala Asp Met Lys Gly
            20                  25                  30

Ser Phe Lys Lys Asn Val Val Leu Glu Val Phe Thr Ala Glu Trp Cys
        35                  40                  45

Gly Tyr Cys Pro Gly Gly Lys Glu Arg Ile Ala Lys Ala Ile Glu Met
    50                  55                  60

Leu Asp Asp Glu Tyr Lys Glu Arg Val Phe Gln Thr Phe Val His Tyr
65                  70                  75                  80

Asn Asp Gly Ile Ser Lys Lys Trp Pro Arg Val Gly Gln Leu Phe Ile
                85                  90                  95

Ala Leu Asp Gln Thr Leu Gly Ile Pro Gly Phe Pro Thr Phe Ser Val
            100                 105                 110

Cys Arg Met Glu Lys Lys Gly Glu Asn Leu Ser Ile Gly Ala Pro Ile
        115                 120                 125

Ala Ile Lys Asn Lys Ile Met Lys Gly Phe Gly Asp Gly Thr Ala Pro
    130                 135                 140

```
Ala Glu Val Asn Leu Lys Leu Thr Lys Gly Ala Thr Pro Glu Asp Val
145                 150                 155                 160

Cys Thr Ala Thr Phe Thr Gly Lys Val Asp Ala Asp Leu Ile Gly Lys
                165                 170                 175

Pro Leu Met Leu Thr Ala Tyr Val Leu Lys Asn Asn Met Lys Pro Ile
            180                 185                 190

Asn Pro Gln Asn Gly Ala Gly Asp Gly Tyr Leu His Gln His Thr Val
        195                 200                 205

Leu Met Ile Leu Ser Thr Asp Val Lys Gly Asp Ala Leu Asn Ile Ala
    210                 215                 220

Ala Asp Gly Ser Phe Thr Ile Lys Lys Glu Phe Lys Leu Asp Gly Phe
225                 230                 235                 240

Glu Ile Lys Asp Thr Asp Val Leu Ala Phe Val His His Pro Met Ser
                245                 250                 255

Asn Ala Glu Asn His Ser Ile Ile Asn Ala Gly Gln Glu Ser Leu Asp
            260                 265                 270

Lys Ala Glu Pro Thr Ala Thr Glu Gln Ile Val Ala Thr Pro Ser Val
        275                 280                 285

Lys Ala Tyr Val Gln Asn Gly Lys Ile Val Val Glu Glu Glu Tyr Ser
290                 295                 300

Lys Met Glu Val Phe Asn Ala Thr Gly Gln Leu Val Lys Asn Glu Ser
305                 310                 315                 320

Leu Val Pro Gly Val Tyr Val Val Arg Ile Thr Ala Asn Gly Val Met
                325                 330                 335

Tyr Phe Leu Lys Val Leu Val Pro
            340
```

<210> SEQ ID NO 20
<211> LENGTH: 1035
<212> TYPE: DNA
<213> ORGANISM: Porphyromonas gingivalis (strain W83; PG0616)

<400> SEQUENCE: 20

```
atgaaaagat tattactctc tgctgctatc ctaagtagta tggctttgtt taatgtcaat    60
gcacaagagt tgaaaacctc tgctgacatg aaaggttctt ttaagaagaa tgtggtattg   120
gaggtattta ctgccgaatg gtgcggttac tgtccaggtg aaaagagcg cattgcaaaa    180
gcaattgaaa tgttggatga tgaatataag gagcgtgttt tcagacatt tgttcattat    240
aatgatggga tctcaaaaaa atggcctcgt gttggccaac ttttcattgc attggatcaa   300
acattgggca ttccgggttt tccgactttt tcagtttgcc gtatgaagaa aaaaggtgaa   360
aatctttcaa taggtgctcc aatagcaatt aaaaataaga ttatgaaagg ttttggtgat   420
ggtacagccc ctgcagaggt aaaccttaaa ttgaccaaag gtgcaacacc ggaagatgta   480
tgtacagcta catttactgg taaagtcgat gctgacctca tagggaaacc tcttatgttg   540
actgcatatg tattgaaaaa caatatgaag cctattaatc cgcaaaatgg agctggggat   600
ggatatctcc accaacatac tgtgttaatg attctctcca cagatgtaaa aggagacgct   660
ttaaatattg cagccgatgg aagttttacc atcaagaaag aatttaagtt ggatggcttt   720
gaaattaaag atacagatgt tcttgctttc gtacaccatc caatgtccaa tgcggaaaac   780
cattctatta tcaatgccgg cagagaaagc cttgataaag cagagcctac agctacagaa   840
caaattgttg ctacccccctc tgtcaaagca tatgttcaga atggcaaaat tgttgtagag   900
gaagagtatt ccaagatgga agtattcaat gcaactggtc aacttgtcaa aaatgaatcc   960
```

-continued

```
cttgtccccg tgtctatgt tgtccgtata acggcaaacg gtgtaatgta tttccttaaa    1020
gtcttggttc cttga                                                    1035
```

<210> SEQ ID NO 21
<211> LENGTH: 483
<212> TYPE: PRT
<213> ORGANISM: Artificial Sequence
<220> FEATURE:
<223> OTHER INFORMATION: Synthetic construct (of PG0495 of P. gingivalis strain W50)

<400> SEQUENCE: 21

```
Met His His His His His Ser Ser Gly Leu Val Pro Arg Gly Ser
1               5                   10                  15

Gly Met Lys Glu Thr Ala Ala Lys Phe Glu Arg Gln His Met Asp
                20                  25                  30

Ser Pro Asp Leu Gly Thr Asp Asp Asp Lys Leu Gln Thr Met Ala
                35                  40                  45

Pro Asn Tyr Phe His Ala Asp Pro Gln Gln Phe Lys His Arg Ile Val
50                  55                  60

Lys Glu Lys Ser Phe Ser Ser Tyr Ser Asn Tyr Glu Tyr Gly Val Asp
65                  70                  75                  80

Asn Arg Leu Gln Arg Ile Tyr Ser Val Asp Glu Ser Ser Gly Glu Ile
                85                  90                  95

Glu His Glu Arg Arg Phe Phe Asn Glu Gly Gly Tyr Met Ile Arg
                100                 105                 110

Glu Glu Glu Tyr Asp Gly Thr Val Gln Ile Pro Val Arg Lys Trp Glu
                115                 120                 125

Phe Val Arg Asp Asp Lys Gly Tyr Ile Thr His Phe Ser Arg Tyr Ser
130                 135                 140

Pro Lys Asp Gly Ser Gln Glu Leu Ile Glu Asp Ile Arg Ile Asp Phe
145                 150                 155                 160

Ser Tyr Asp Ala Asp Met Lys Leu Ile Lys Ala Asp Ile Asp Phe Phe
                165                 170                 175

Asp Ile Met Ala Asn Val Trp Gly Asp Leu Arg Thr Thr Lys Leu Val
                180                 185                 190

Tyr Asn Glu Asn Gly Leu Leu Lys Glu Met Ile Gln Thr Asp Pro Gly
                195                 200                 205

Ser Gly Gln Glu Phe Asn Arg Glu Leu Thr Tyr Asn Asn Leu Asn
                210                 215                 220

Lys Ile Val Ala Ile Arg Phe Ile Pro Gly Pro Ala Ser Thr Gly Leu
225                 230                 235                 240

Asn Glu Phe Glu Leu Ile Tyr Glu Tyr Asp Ser Glu Gly Met Asp Ile
                245                 250                 255

Val Lys Ala Gly Arg Asp Asp Phe Trp Tyr Tyr Glu Tyr Asp Lys
                260                 265                 270

Glu Met Leu Ala Ser Glu Thr Phe Phe Pro Lys Pro Ser Ile Ala Asp
                275                 280                 285

Leu Val Tyr Phe Gly Leu Lys Asp Tyr Val Asp Phe Ser Gly Leu Pro
                290                 295                 300

Phe Lys Asn Ser Tyr Thr His Val Val Lys Glu Ser Thr Asn Glu
305                 310                 315                 320

Val Glu Ala Ile Tyr Glu Pro Ile Ser Val Tyr Ser Val Val Ile
                325                 330                 335

Gln Pro Glu Asn Gly Glu Ile Lys Leu Thr Ala Asp Gly Gln Pro Leu
```

```
                340             345             350
Asn Ser Gly Ser Thr Leu Val Ala Gly Arg Arg Ile Lys Ile His Pro
            355                 360                 365
Ile Pro Ala Glu Gly Tyr Glu Val Asp Lys Val Met Val Asn Gly Glu
        370                 375                 380
Asn Ile Glu Ala Pro Tyr Glu Phe Leu Leu Glu Lys Asp Thr Glu Val
385                 390                 395                 400
Thr Ala Leu Met Lys Lys Ser Asn Ala Val Gly Glu Val Asp Thr Lys
                405                 410                 415
Gly Phe His Val Tyr Pro Ile Pro Thr Ser Lys Asp Leu Thr Ile Glu
            420                 425                 430
Ile Pro Ala Glu Met Val Gly Lys Val Ala Ser Leu Ile Asp Met Asn
        435                 440                 445
Gly Gln Ile Val Tyr Arg Val Thr Leu Asn Asn Ile Phe Gln Gln Ile
    450                 455                 460
Asp Ile Ser His Leu Lys Gly Val Phe Leu Leu Gln Ile Gly Asp Ile
465                 470                 475                 480
Gln Lys Glu

<210> SEQ ID NO 22
<211> LENGTH: 1452
<212> TYPE: DNA
<213> ORGANISM: Artifical Sequence

<400> SEQUENCE: 22
atgcaccatc atcatcatca ttcttctggt ctggtgccac gcggttctgg tatgaaagaa     60
accgctgctg ctaaattcga acgccagcac atggacagcc agatctggg taccgatgac    120
gacgacaagt tgcagacaat ggctccaaat tacttccatg ccgatccgca gcaattcaaa    180
cacaggattg taaaagaaaa aagcttctcc tcctactcta attacgaata cggagtcgac    240
aaccgtctgc aaaggatcta ttcggtggat gagtcttcgg gagagatcga acacgaaaga    300
cgattctttt tcaatgaagg cggatatatg attcgtgagg aggaatacga tggaaccgtt    360
cagatacctg tcagaaaatg ggaatttgtc cgcgatgaca agggttatat cactcatttc    420
agcagatact cgcctaaaga tggaagtcag gagttgatag aggatatccg tatcgatttt    480
tcctacgatg ccgatatgaa actgatcaaa gcggatatag atttcttcga cattatggcc    540
aatgtatggg gcgatctgcg cacgacaaaa ctagtctata tgaaaacgg actcttgaaa    600
gagatgattc aaaccgatcc gggaagtgga caagaattca tcgggaaga gcttacatac    660
aataacctca acaaaatagt tgctatcagg tttataccgg gaccggccag tacaggtttg    720
aacgaatttg aattgatata cgaatacgac agtgaaggaa tggatattgt caaagccggg    780
cgtgacgatt tctggtacta ctatgagtac gacaaagaaa tgctcgcttc agagacattc    840
ttcccaaagc cttccatagc ggatttagta tatttcggac ttaaagatta tgtggatttt    900
tcaggactac ccttcaaaaa cagttatact catgtagtag tcaaagaatc tacaaatgaa    960
gtggaagcga tttatgaacc tatctctgta tattccgtag tggtcatcca gcccgaaaat   1020
ggagagataa agctaacggc cgatgggcag cccctgaaca gcggttccac attagtggca   1080
ggccgtcgta ttaaaataca tcccatccct gccgaaggtt acgaagtgga caaggtaatg   1140
gtgaacggag agaatatcga agctccgtat gaattcctc ttgagaaaga tacagaagtg   1200
acagccctga tgaagaagag caatgccgta ggagaagtcg acaccaaagg cttccatgtc   1260
tatcccatac ccacatcaaa agatttgacg atagagatac cggcagaaat ggtaggcaaa   1320
```

```
gtggcatctc ttatagatat gaacggacag attgtttaca gagttacgct taataacatc    1380
ttccagcaga tagatatcag ccatctcaag ggcgttttcc tcttgcagat cggtgatatt    1440
cagaaagagt ga                                                        1452
```

<210> SEQ ID NO 23
<211> LENGTH: 367
<212> TYPE: PRT
<213> ORGANISM: Artificial Sequence
<220> FEATURE:
<223> OTHER INFORMATION: Synthetic Construct (of PG0616 of P. gingivalis strain W50)

<400> SEQUENCE: 23

```
Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Met Gln Glu Leu Lys
        35                  40                  45

Thr Ser Ala Asp Met Lys Gly Ser Phe Lys Lys Asn Val Val Leu Glu
50                  55                  60

Val Phe Thr Ala Glu Trp Cys Gly Tyr Cys Pro Gly Gly Lys Glu Arg
65                  70                  75                  80

Ile Ala Lys Ala Ile Glu Met Leu Asp Asp Glu Tyr Lys Glu Arg Val
                85                  90                  95

Phe Gln Thr Phe Val His Tyr Asn Asp Gly Ile Ser Lys Lys Trp Pro
            100                 105                 110

Arg Val Gly Gln Leu Phe Ile Ala Leu Asp Gln Thr Leu Gly Ile Pro
        115                 120                 125

Gly Phe Pro Thr Phe Ser Val Cys Arg Met Glu Lys Lys Gly Glu Asn
130                 135                 140

Leu Ser Ile Gly Ala Pro Ile Ala Ile Lys Asn Lys Ile Met Lys Gly
145                 150                 155                 160

Phe Gly Asp Gly Thr Ala Pro Ala Glu Val Asn Leu Lys Leu Thr Lys
                165                 170                 175

Gly Ala Thr Pro Glu Asp Val Cys Thr Ala Thr Phe Thr Gly Lys Val
            180                 185                 190

Asp Ala Asp Leu Ile Gly Lys Pro Leu Met Leu Thr Ala Tyr Val Leu
        195                 200                 205

Lys Asn Asn Met Lys Pro Ile Asn Pro Gln Asn Gly Ala Gly Asp Gly
210                 215                 220

Tyr Leu His Gln His Thr Val Leu Met Ile Leu Ser Thr Asp Val Lys
225                 230                 235                 240

Gly Asp Ala Leu Asn Ile Ala Ala Asp Gly Ser Phe Thr Ile Lys Lys
                245                 250                 255

Glu Phe Lys Leu Asp Gly Phe Glu Ile Lys Asp Thr Asp Val Leu Ala
            260                 265                 270

Phe Val His His Pro Met Ser Asn Ala Glu Asn His Ser Ile Ile Asn
        275                 280                 285

Ala Gly Gln Glu Ser Leu Asp Lys Ala Glu Pro Thr Ala Thr Glu Gln
    290                 295                 300

Ile Val Ala Thr Pro Ser Val Lys Ala Tyr Val Gln Asn Gly Lys Ile
305                 310                 315                 320

Val Val Glu Glu Glu Tyr Ser Lys Met Glu Val Phe Asn Ala Thr Gly
```

```
                325                 330                 335
Gln Leu Val Lys Asn Glu Ser Leu Val Pro Gly Val Tyr Val Arg
            340                 345                 350

Ile Thr Ala Asn Gly Val Met Tyr Phe Leu Lys Val Leu Val Pro
            355                 360                 365

<210> SEQ ID NO 24
<211> LENGTH: 1104
<212> TYPE: DNA
<213> ORGANISM: Artificial Sequence
<220> FEATURE:
<223> OTHER INFORMATION: Synthetic Construct (of PG0616 of P. gingivalis
      W50)

<400> SEQUENCE: 24
atgcaccatc atcatcatca ttcttctggt ctggtgccac gcggttctgg tatgaaagaa       60
accgctgctg ctaaattcga acgccagcac atggacagcc agatctgggt accgatgac      120 gacgacaaga tgcaagagtt gaaaacctct gctgacatga aggttctttt aagaagaat      180 gtggtattgg aggtatttac tgccgaatgg tgcggttact gtccaggtgg aaaagagcgc     240
attgcaaaag caattgaaat gttggatgat gaatataagg agcgtgtttt tcagacattt     300
gttcattata atgatgggat ctcaaaaaaa tggcctcgtg ttggccaact tttcattgca     360
ttggatcaaa cattgggcat tccgggtttt ccgactttt cagtttgccg tatggagaaa      420
aaaggtgaaa atctttcaat aggtgctcca atagcaatta aaaataagat tatgaaaggt     480
tttggtgatg gtacagcccc tgcagaggta aaccttaaat tgaccaaagg tgcaacaccg     540
gaagatgtat gtacagctac atttactggt aaagtcgatg ctgacctcat agggaaacct     600
cttatgttga ctgcatatgt attgaaaaac aatatgaagc ctattaatcc gcaaaatgga     660
gctggggatg gatatctcca ccaacatact gtgttaatga ttctctccac agatgtaaaa     720
ggagacgctt taaatattgc agccgatgga agttttacca tcaagaaaga atttaagttg     780
gatggctttg aaattaaaga tacagatgtt cttgctttcg tacaccatcc aatgtccaat     840 gcggaaaaacc attctattat caatgccggg caagaaagcc ttgataaagc agagcctaca     900
gctacagaac aaattgttgc taccccctct gtcaaagcat atgttcagaa tggcaaaatt     960
gttgtagagg aagagtattc caagatggaa gtattcaatg caactggtca acttgtcaaa    1020
aatgaatccc ttgtccccgg tgtctatgtt gtccgtataa cggcaaacgg tgtaatgtat    1080
ttccttaaag tcttggttcc ttga                                           1104

<210> SEQ ID NO 25
<211> LENGTH: 413
<212> TYPE: PRT
<213> ORGANISM: Artificial Sequence
<220> FEATURE:
<223> OTHER INFORMATION: Synthetic Construct (of PG0654 of P. gingivalis
      strain W50)

<400> SEQUENCE: 25

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Met Gln Ser Pro Arg
        35                  40                  45

Ile Pro Gln Val Asp Val His Thr Arg Ile Ala Arg Asn Ala Arg Tyr
    50                  55                  60
```

Arg Leu Asp Lys Ile Ser Val Pro Asp Ser Arg Gln Ile Phe Asp Tyr
65                  70                  75                  80

Phe Tyr Lys Glu Glu Thr Ile Pro Thr Lys Ile Gln Thr Thr Thr Gly
                85                  90                  95

Gly Ala Ile Thr Ser Ile Asp Ser Leu Phe Tyr Glu Asp Asp Arg Leu
            100                 105                 110

Val Gln Val Arg Tyr Phe Asp Asn Asn Leu Glu Leu Lys Gln Ala Glu
        115                 120                 125

Lys Tyr Val Tyr Asp Gly Ser Lys Leu Val Leu Arg Glu Ile Arg Lys
130                 135                 140

Ser Pro Thr Asp Glu Thr Pro Ile Lys Lys Val Ser Tyr His Tyr Leu
145                 150                 155                 160

Cys Gly Ser Asp Met Pro Phe Glu Ile Thr Thr Glu Met Ser Asp Gly
                165                 170                 175

Tyr Phe Glu Ser His Thr Leu Asn Tyr Leu Asn Gly Lys Ile Ala Arg
            180                 185                 190

Ile Asp Ile Met Thr Gln Gln Asn Pro Ser Ala Glu Leu Ile Glu Thr
        195                 200                 205

Gly Arg Met Val Tyr Glu Phe Asp Ala Asn Asn Asp Ala Val Leu Leu
210                 215                 220

Arg Asp Ser Val Phe Leu Pro Leu Gln Asn Lys Trp Val Glu Met Phe
225                 230                 235                 240

Thr His Arg Tyr Thr Tyr Asp Asn Lys His Asn Cys Ile Arg Trp Glu
                245                 250                 255

Gln Asp Glu Phe Gly Thr Leu Thr Leu Ala Asn Asn Phe Glu Tyr Asp
            260                 265                 270

Thr Thr Ile Pro Leu Ser Ser Val Leu Phe Pro Thr His Glu Glu Phe
        275                 280                 285

Phe Arg Pro Leu Leu Pro Asn Phe Met Lys His Met Arg Thr Lys Gln
290                 295                 300

Thr Tyr Phe Asn Asn Ser Gly Glu Gly Leu Ser Glu Val Cys Asp Tyr
305                 310                 315                 320

Asn Tyr Phe Tyr Thr Asp Met Gln Gly Asn Ala Leu Thr Asp Val Ala
                325                 330                 335

Val Asn Glu Ser Ile Lys Ile Tyr Pro Arg Pro Ala Thr Asp Phe Leu
            340                 345                 350

Arg Ile Glu Gly Ser Gln Leu Leu Arg Leu Ser Leu Phe Asp Met Asn
        355                 360                 365

Gly Lys Leu Ile Arg Ala Thr Glu Leu Thr Gly Asp Leu Ala Ile Ile
370                 375                 380

Gly Val Ala Ser Leu Pro Arg Gly Thr Tyr Ile Ala Glu Ile Thr Ala
385                 390                 395                 400

Ala Asn Ser Lys Thr Ile Arg Ala Lys Val Ser Leu Arg
                405                 410

<210> SEQ ID NO 26
<211> LENGTH: 1242
<212> TYPE: DNA
<213> ORGANISM: Artificial Sequence
<220> FEATURE:
<223> OTHER INFORMATION: Synthetic Construct (of PG0654 of P. gingivalis
      strain W50)

<400> SEQUENCE: 26
atgcaccatc atcatcatca ttcttctggt ctggtgccac gcggttctgg tatgaaagaa    60

```
accgctgctg ctaaattcga acgccagcac atggacagcc cagatctggg taccgatgac      120
gacgacaaga tgcagtcacc ccgaatccct caagtggatg tacacactcg catcgcaaga      180
aatgcccgtt atcgactgga caagatcagt gtcccggatt ctcgtcagat attcgattac      240
ttctataaag aagaaacgat acccactaaa atacaaacga ccacaggagg tgcaattaca      300
agcatcgatt cgcttttcta tgaagacgac aggttggttc aggtgcgcta ttttgacaat      360
aaccttgaat aaaacaagc ggagaagtat gtatacgacg ttctaagct ggtccttcga        420 gaaattcgca agtcgccgac agacgaaacg ccaataaaga aagttagcta tcactatctc      480
tgtggcagcg atatgccttt tgagattacg acagagatga gcgatggcta ttttgaaagc      540
catacgctta actatctgaa tggaaagatt gcccgaatag atatcatgac tcaacagaac      600
ccatcggccg aattgatcga aacgggtaga atggtatatg agtttgatgc caataatgat      660
gctgtactgc ttcgtgacag tgtatttctt cctcttcaaa acaagtgggt agaaatgttt      720
actcaccgtt atacatacga caataagcat aattgtattc gttgggaaca agacgaattc      780
ggcaccctca cccttgccaa caacttcgaa tacgacacca ctatccctct gtcgtctgta      840
ttgttcccca cgcatgagga gttcttccgt cctcttcttc ccaattttat gaagcatatg      900
cgtacgaagc aaacgtattt caataactcc ggagaaggct tgtcagaggt atgcgattac      960
aactacttct ataccgatat gcagggtaat gcactgaccg atgttgccgt gaacgaatcg     1020
atcaagattt atcctcgtcc tgccacggat tttctgcgta tagaaggttc gcaactgctt     1080
cgcctttcgc tattcgacat gaacgggaag ctcatcagag ctaccgaatt gacaggcgat     1140
ttggccatta tcggagttgc atctcttccg agaggcactt acatcgcaga ataactgct      1200 gcaaacagca aaaccatacg tgcaaaagta tcgctcagat aa                        1242
```

<210> SEQ ID NO 27
<211> LENGTH: 449
<212> TYPE: PRT
<213> ORGANISM: Artificial sequence
<220> FEATURE:
<223> OTHER INFORMATION: Synthetic Construct (of PG1374 of P. gingivalis strain W50)

<400> SEQUENCE: 27

```
Met His His His His His Ser Ser Gly Leu Val Pro Arg Gly Ser
1               5                   10                  15

Gly Met Lys Glu Thr Ala Ala Lys Phe Glu Arg Gln His Met Asp
                20                  25                  30

Ser Pro Asp Leu Gly Thr Asp Asp Asp Lys Met Gln Phe Val Pro
            35                  40                  45

Ala Pro Thr Thr Gly Ile Arg Met Ser Val Thr Thr Lys Ala Val
        50                  55                  60

Gly Glu Lys Ile Glu Leu Leu Val His Ser Ile Glu Lys Lys Gly Ile
65                  70                  75                  80

Trp Ile Asp Leu Asn Gly Asp Ala Thr Tyr Gln Gln Gly Glu Glu Ile
                85                  90                  95

Thr Val Phe Asp Glu Ala Tyr His Glu Tyr Thr Ile Gly Thr Gln Thr
                    100                 105                 110

Leu Thr Ile Tyr Gly Asn Thr Thr Arg Leu Gly Cys Arg Ser Thr Gly
            115                 120                 125

Ala Thr Ala Val Asp Val Thr Lys Asn Pro Asn Leu Thr Tyr Leu Ala
        130                 135                 140
```

```
Cys Pro Lys Asn Asn Leu Lys Ser Leu Asp Leu Thr Gln Asn Pro Lys
145                 150                 155                 160
Leu Leu Arg Val Trp Cys Asp Ser Asn Glu Ile Glu Ser Leu Asp Leu
                165                 170                 175
Ser Gly Asn Pro Ala Leu Ile Ile Leu Gly Cys Asp Arg Asn Lys Leu
            180                 185                 190
Thr Glu Leu Lys Thr Asp Asn Asn Pro Lys Leu Ala Ser Leu Trp Cys
        195                 200                 205
Ser Asp Asn Asn Leu Thr Glu Leu Glu Leu Ser Ala Asn Pro Arg Leu
    210                 215                 220
Asn Asp Leu Trp Cys Phe Gly Asn Arg Ile Thr Lys Leu Asp Leu Ser
225                 230                 235                 240
Ala Asn Pro Leu Leu Val Thr Leu Trp Cys Ser Asp Asn Glu Leu Ser
                245                 250                 255
Thr Leu Asp Leu Ser Lys Asn Ser Asp Val Ala Tyr Leu Trp Cys Ser
            260                 265                 270
Ser Asn Lys Leu Thr Ser Leu Asn Leu Ser Gly Val Lys Gly Leu Ser
        275                 280                 285
Val Leu Val Cys His Ser Asn Gln Ile Ala Gly Glu Met Thr Lys
    290                 295                 300
Val Val Asn Ala Leu Pro Thr Leu Ser Pro Gly Ala Gly Ala Gln Ser
305                 310                 315                 320
Lys Phe Val Val Asp Leu Lys Asp Thr Asp Lys Asn Ile Cys
                325                 330                 335
Thr Val Lys Asp Val Glu Lys Ala Lys Ser Lys Asn Trp Arg Val Phe
            340                 345                 350
Asp Phe Asn Gly Asp Ser Asp Asn Met Leu Pro Tyr Glu Gly Ser Pro
        355                 360                 365
Thr Ser Asn Leu Ala Val Asp Ala Pro Thr Val Arg Ile Tyr Pro Asn
    370                 375                 380
Pro Val Gly Arg Tyr Ala Leu Val Glu Ile Pro Glu Ser Leu Leu Gly
385                 390                 395                 400
Gln Glu Ala Ala Leu Tyr Asp Met Asn Gly Val Lys Val Tyr Ser Phe
                405                 410                 415
Ala Val Glu Ser Leu Arg Gln Asn Ile Asp Leu Thr His Leu Pro Asp
            420                 425                 430
Gly Thr Tyr Phe Phe Arg Leu Asp Asn Tyr Thr Thr Lys Leu Ile Lys
        435                 440                 445
Gln

<210> SEQ ID NO 28
<211> LENGTH: 1350
<212> TYPE: DNA
<213> ORGANISM: Artificial Sequence
<220> FEATURE:
<223> OTHER INFORMATION: Synthetic Construct (of PG1374 of P. gingivalis
      strain W50)

<400> SEQUENCE: 28
atgcaccatc atcatcatca ttcttctggt ctggtgccac gcggttctgg tatgaaagaa     60
accgctgctg ctaaattcga acgccagcac atggacagcc agatctggg taccgatgac    120 gacgacaaga tgcagtttgt tccggctccc accacaggga ttcgcatgtc tgtcactaca    180
accaaggccg taggcgaaaa aatcgaattg ttggttcatt ccatagagaa gaaaggcatc    240
tggatcgatc tcaatgggga tgccacttac caacaaggag aggaaataac cgtattcgat    300
```

```
gaggcatacc acgaatacac gatcgggacg caaaccctca ctatctatgg taatacgacc    360
cgattgggct gtcgatctac cggtgcaacg gctgtcgatg taacgaaaaa ccctaatctg    420
acctatctcg catgcccgaa aataatctg aaatcattgg acttgacgca aacccaaag     480
ttgctgcgag tttggtgcga ctctaacgaa atagaaagtt tggacctgag tggcaatccg    540
gctttgatca tcctcggctg tgacaggaat aagctgactg agctgaagac cgataacaac    600
cccaagttgg cctctctttg gtgttctgat aataacctga cggagttgga actcagtgcc    660
aatcctcgtc tcaatgatct ttggtgcttc ggtaatcgga tcacgaaact cgatctgagt    720
gccaatcctc tattggtaac actttggtgc agtgacaatg agctttcgac cttggatctt    780
tccaagaatt cggacgttgc ttacctttgg tgttcatcga caaacttac atccttgaat     840
ctgtcggggg tgaagggact gagtgttttg gtttgtcatt ccaatcagat cgcaggtgaa    900
gaaatgacga agtggtgaa tgctttgccc acactatctc ccggcgcagg cgctcagagc     960
aagttcgtcg ttgtagacct caaggacact gatgagaaga atatctgtac cgtaaaggat   1020
gtggaaaaag ctaaaagtaa gaactggcga gtatttgact tcaacggtga ttctgacaat   1080
atgcttccat acgaaggaag tccgacatcg aacttggcag tagatgctcc cactgtcagg   1140
atatatccca atccggtagg aagatatgcg ctcgtcgaga tccccgagtc tcttttaggg   1200
caggaagctg ctttatacga tatgaatggg gtaaaagtct atagtttcgc ggtagagtct   1260
cttcgtcaga acattgacct gacacatctt cccgacggca cttatttctt ccgtctcgat   1320
aactatacca ctaagctcat caaacagtaa                                    1350
```

<210> SEQ ID NO 29
<211> LENGTH: 264
<212> TYPE: PRT
<213> ORGANISM: Artificial Sequence
<220> FEATURE:
<223> OTHER INFORMATION: Synthetic construct (PG2172 of P. gingivalis strain W50)

<400> SEQUENCE: 29

```
Met His His His His His Ser Ser Gly Leu Val Pro Arg Gly Ser
1               5                   10                  15

Gly Met Lys Glu Thr Ala Ala Lys Phe Glu Arg Gln His Met Asp
                20                  25                  30

Ser Pro Asp Leu Gly Thr Asp Asp Asp Lys Met Gln Val Val Ile
            35                  40                  45

Lys Val Gly Asp Ala Ile Leu Glu Asn Asn Ala Thr Val Asp Ile Thr
50                  55                  60

Ala Phe Thr Thr Glu Asp Gly Thr Glu Met Lys Phe Glu Gly Met
65                  70                  75                  80

Val Ile Asn Gln Ser Ala Thr Pro Ile Asn Val Ile Gly Lys Ile Thr
                85                  90                  95

Lys Gln Glu Met Ile Gly Asp Gly His Phe Ala Leu Cys Phe Gly Gln
                100                 105                 110

Cys Met Gly Pro Asn Val Ser Val Ser Pro Ile Val Glu Ala Leu Asp
            115                 120                 125

Gly Glu Gly Glu Tyr Val Ser Leu His Tyr Lys Phe Pro Val Ser Asn
            130                 135                 140

Glu Gly His Thr Gly Ala Phe Thr Phe Ser Cys Phe Pro Glu Ser Gly
145                 150                 155                 160

Ala Pro Gly Thr Glu Leu Ala Thr Val Asn Ile Asn Phe Lys Tyr Lys
```

```
                165                 170                 175
Gly Gly Gly Thr Gly Leu Thr Asn Ile Gly Leu Gly Arg Ile Ala Leu
            180                 185                 190

Ile Gln Ser Gly Asn Thr Cys Thr Leu Gln Tyr Asn Ser Asn Gly Lys
        195                 200                 205

Arg Leu Ala Leu Glu Val Tyr Asn Leu Leu Gly Val Lys Val Phe Thr
    210                 215                 220

Ser Gln Leu Pro Ala Gly Ser Gly Ser Tyr Thr Leu Pro Val Arg Leu
225                 230                 235                 240

Gln Arg Gly Val His Ile Phe Arg Ile Thr Glu Gly Gly Lys Pro Ala
                245                 250                 255

Phe Val Gln Lys Tyr Leu Ile Lys
            260

<210> SEQ ID NO 30
<211> LENGTH: 795
<212> TYPE: DNA
<213> ORGANISM: Artificial Sequence
<220> FEATURE:
<223> OTHER INFORMATION: Synthetic Construct (PG2172 of P. gingivalis
      strain W50)

<400> SEQUENCE: 30
atgcaccatc atcatcatca ttcttctggt ctggtgccac gcggttctgg tatgaaagaa      60
accgctgctg ctaaattcga acgccagcac atggacagcc agatctggg taccgatgac     120 gacgacaaga tgcaagttgt gatcaaggtg ggagatgcca tcttggaaaa caatgccact     180
gtggacatta ctgctttcac aacagaagat ggtacggaag agatgaaatt tgaaggaatg     240
gttatcaacc aatccgctac acctatcaat gtaatcggca agattaccaa gcaagaaatg     300
atcggtgatg gacactttgc tttgtgcttt ggtcagtgta tggggccgaa tgtatctgta     360
tcccccattg tggaggctct tgatggtgaa ggagagtacg tctctttgca ttataaattt     420
cccgtgtcca atgaagggca tacgggagct ttcactttta gctgcttccc cgagagtggt     480
gctcccggca cagaattggc tacagtgaac attaacttca gtacaaagg cggtggaacc     540 ggtttgacta atatcgggct agggcgtata gctcttatcc agagcggtaa tacttgcacc     600
cttcagtaca acagcaatgg caagcgtctt gcccttgaag tgtacaatct cttaggcgta     660
aaggtattta cctctcagct gccccgcagga tccggctctt atacgctgcc ggtgcgtctg     720
cagcgtggtg tgcatatctt ccgcatcaca gaaggaggta agcctgcgtt tgttcagaag     780
tatctgatta agtaa                                                      795

<210> SEQ ID NO 31
<211> LENGTH: 297
<212> TYPE: PRT
<213> ORGANISM: Artificial Sequence
<220> FEATURE:
<223> OTHER INFORMATION: Synthetic Construct (PG1795 of P. gingivalis
      strain W50)

<400> SEQUENCE: 31

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Met Gln Ser Leu Ser
        35                  40                  45
```

```
Thr Ile Lys Val Gln Asn Asn Ser Val Gln Gln Pro Arg Glu Glu Ala
        50                  55                  60

Thr Ile Gln Val Cys Gly Glu Leu Ala Glu Gln Val Asp Cys Ile Gly
 65                  70                  75                  80

Thr Gly Asn Ser Ala Ile Ile Ala Ala Ala Lys Phe Glu Ser Asp
                85                  90                  95

Asp Leu Glu Ser Tyr Val Gly Trp Glu Ile Met Ser Val Asp Phe Phe
                100                 105                 110

Pro Gly Tyr Lys Ala Cys Lys Tyr Thr Ser Ala Val Trp Ala Asp Asp
            115                 120                 125

Met Thr Ile Leu Gly Gln Ser Glu Asp Ser Asp Pro Glu Met Gln Thr
    130                 135                 140

Ile Asn Asn Leu Ala Leu Lys Thr Ser Val Lys Ile Glu Ala Gly Lys
145                 150                 155                 160

Asn Tyr Ile Val Gly Tyr Ile Ala Asn Thr Ala Gly Gly His Pro Ile
                165                 170                 175

Gly Cys Asp Gln Gly Pro Ala Val Asp Gly Tyr Gly Asp Leu Val Ser
            180                 185                 190

Ile Ser Glu Asp Gly Gly Ala Thr Phe Pro Pro Phe Glu Ser Leu His
    195                 200                 205

Gln Ala Val Pro Thr Leu Asn Tyr Asn Ile Tyr Val Val His Leu
210                 215                 220

Lys Lys Gly Glu Gly Val Glu Ala Val Leu Thr Asn Asp Lys Ala Asn
225                 230                 235                 240

Ala Tyr Val Gln Asn Gly Val Ile Tyr Val Ala Gly Ala Asn Gly Arg
                245                 250                 255

Gln Val Ser Leu Phe Asp Met Asn Gly Lys Val Val Tyr Thr Gly Val
            260                 265                 270

Ser Glu Thr Ile Ala Ala Pro Gln Lys Gly Met Tyr Ile Leu Arg Val
        275                 280                 285

Gly Ala Lys Ser Ile Lys Leu Ala Ile
    290                 295

<210> SEQ ID NO 32
<211> LENGTH: 894
<212> TYPE: DNA
<213> ORGANISM: Artificial Sequence
<220> FEATURE:
<223> OTHER INFORMATION: Synthetic Construct (PG1795 of P. gingivalis
      strain W50)

<400> SEQUENCE: 32
atgcaccatc atcatcatca ttcttctggt ctggtgccac gcggttctgg tatgaaagaa    60
accgctgctg ctaaattcga acgccagcac atggacagcc agatctgggt accgatgac   120 gacgacaaga tgcagtcttt gagcacaatc aaagtacaga caattcagt acagcaacct   180 cgtgaggaag ccactattca ggtttgtgga gaattggcag agcaagttga ctgcattggg   240
acaggtaatt ctgcaatcat agccgctgca gcgaaatttg aaagcgatga tctcgaaagc   300
tatgttggct gggagatcat gagtgttgat ttcttccctg gatataaagc gtgcaagtac   360
acatctgcag tctgggctga tgatatgacc attttgggcc aatcagaaga tagtgatccc   420
gaaatgcaga ctatcaacaa tcttgctctc aagactagtg tcaagattga agccggcaag   480
aattacatag ttggttatat tgctaatacc gcaggtggac atcctatcgg atgtgatcag   540
ggccctgccg ttgatggtta tggagatttg gtttctatat cagaagatgg tggtgctact   600
```

```
ttccctccgt tcgaatctct tcatcaagca gttcctacct taaattacaa catctatgtc      660
gttgttcatt tgaagaaggg tgaaggtgtt gaggctgttc ttaccaacga caaggctaat      720
gcttatgttc agaatggcgt tatctatgta gccggagcta atggtcgtca ggtatctctg      780
ttcgacatga acgtaaggt tgtttatacc ggcgttagcg aaacgattgc agctcctcag      840
aagggcatgt atatcctccg tgtaggtgct aagagcatca agctggctat ctaa            894
```

<210> SEQ ID NO 33
<211> LENGTH: 251
<212> TYPE: PRT
<213> ORGANISM: Artificial Sequence
<220> FEATURE:
<223> OTHER INFORMATION: Synthetic Construct (PG0613 of P. gingivalis strain W50)

<400> SEQUENCE: 33

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Met Gln Thr Thr Thr
        35                  40                  45

Asn Ser Ser Arg Ser Tyr Phe Thr Gly Arg Ile Glu Lys Val Ser Leu
50                  55                  60

Asn Leu Gly Val Pro Pro Val Ser Thr Glu Val Trp Gly Met Thr His
65                  70                  75                  80

Asp Ala Asn Gly Leu Pro Phe Glu Ile Pro Ile Ser Phe Ser Arg Phe
                85                  90                  95

Asn Ser Gln Gly Asp Ile Ala Thr Thr Tyr Tyr Ile Ala Asn Ser Glu
            100                 105                 110

Ala Thr Leu Asn Glu Trp Cys Asp Tyr Ala His Pro Gly Gly Ile Val
        115                 120                 125

Arg Val Glu Gly Arg Phe Trp Lys Met Thr Tyr Asn Ile Pro Thr Tyr
    130                 135                 140

Asn Ala Val Cys Thr Arg Ile Thr Phe Glu Asn Gln Glu Ile Glu Gly
145                 150                 155                 160

Thr Ile Val Leu Ile Pro Lys Pro Lys Val Ser Leu Pro His Val Ser
                165                 170                 175

Glu Ser Val Pro Cys Ile Arg Thr Glu Ala Gly Arg Glu Phe Ile Leu
            180                 185                 190

Cys Glu Glu Asp Asp Thr Phe Val Ser His Asp Gly Asn Glu Val Thr
        195                 200                 205

Ile Gly Gly Lys Pro Phe Leu Leu Asn Thr Asn Val Lys Ile Val Gly
    210                 215                 220

Asp Val Ser Gln Lys Tyr Ala Val Gly Val Gly Glu Ile Arg Phe Leu
225                 230                 235                 240

Gln Ile Cys Ala Gln Thr Val Ser Gln Gln Lys
                245                 250
```

<210> SEQ ID NO 34
<211> LENGTH: 756
<212> TYPE: DNA
<213> ORGANISM: Artificial Sequence
<220> FEATURE:
<223> OTHER INFORMATION: Synthetic Construct (PG0613 of P. gingivalis strain W50)

<400> SEQUENCE: 34

```
atgcaccatc atcatcatca ttcttctggt ctggtgccac gcggttctgg tatgaaagaa      60
accgctgctg ctaaattcga acgccagcac atggacagcc agatctggg  taccgatgac     120
gacgacaaga tgcaaacaac gacgaacagt agccggagtt attttacagg acgaatcgag     180
aaggtgagtt tgaacttagg ggtccccccc gtaagcacag aggtttgggg aatgacccat     240
gatgcgaacg gtctcccttt cgaaatacct atctctttca gtcgtttcaa cagccaggga     300
gatatagcta ccacttatta catagcgaat agcgaggcaa ctttgaatga atggtgcgac     360
tatgcacacc cgggcggcat cgtgagggta gaaggtcgtt tttggaaaat gacttacaac     420
ataccaacct acaatgcagt ctgcacccgg attacattcg aaaatcaaga aatagaagga     480
acgatcgtct tgatacccaa gcccaaagtc tcgctgcctc atgtgtcgga atcggtgcct     540
tgcatccgaa ccgaagccgg gagggaattt atcctttgcg aagaagacga cacctttgtg     600
tctcacgatg gtaacgaagt aacgataggc ggtaaacctt tcttgctcaa taccaacgta     660
aagattgtgg gggacgtatc tcaaaagtat gccgtggggg taggagaaat tcgattcctg     720
cagatttgtg cccaaacagt atcacaacaa aaatga                              756
```

<210> SEQ ID NO 35  
<211> LENGTH: 483  
<212> TYPE: PRT  
<213> ORGANISM: Artificial Sequence  
<220> FEATURE:  
<223> OTHER INFORMATION: Synthetic Construct (PG1798 of P. gingivalis strain W50)

<400> SEQUENCE: 35

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Met Gln Thr Lys Asp
        35                  40                  45

Asn Ser Ser Tyr Lys Pro Phe Ser Lys Glu Asp Ile Ala Gly Gly Val
    50                  55                  60

Tyr Ser Leu Pro Thr Gln Asn Arg Ala Gln Lys Asp Asn Ala Glu Trp
65                  70                  75                  80

Leu Leu Thr Ala Thr Val Ser Thr Asn Gln Ser Ala Asp Thr His Phe
                85                  90                  95

Ile Phe Asp Glu Asn Asn Arg Tyr Ile Ala Arg Asp Ile Lys Ala Asn
            100                 105                 110

Gly Val Arg Lys Ser Thr Asp Ser Ile Tyr Tyr Asp Ala Asn Gly Arg
        115                 120                 125

Ile Ser His Val Asp Leu Tyr Ile Ser Phe Ser Gly Gly Glu Pro Ala
    130                 135                 140

Leu Asp Thr Arg Phe Lys Tyr Thr Tyr Asp Asp Glu Gly Lys Met Thr
145                 150                 155                 160

Val Arg Glu Val Phe Met Leu Val Met Asp Pro Asn Thr Pro Ile Ser
                165                 170                 175

Arg Leu Glu Tyr His Tyr Asp Ala Gln Gly Arg Leu Thr His Trp Ile
            180                 185                 190

Ser Phe Ala Phe Gly Ala Glu Ser Gln Lys Asn Thr Tyr His Tyr Asn
        195                 200                 205

Glu Lys Gly Leu Leu Val Ser Glu Val Leu Ser Asn Ala Met Gly Thr
    210                 215                 220
```

```
Thr Tyr Ser Asp Thr Gly Lys Thr Glu Tyr Ser Tyr Asp Asp Ala Asp
225                 230                 235                 240

Asn Met Val Lys Ala Glu Tyr Phe Val Val Gln Gln Gly Lys Ala Trp
            245                 250                 255

Gln Val Leu Lys Arg Glu Glu Tyr Thr Tyr Glu Asp Asn Ile Cys Ile
        260                 265                 270

Gln Tyr Leu Ala Ile Asn Gly Thr Asp Thr Lys Val Tyr Lys Arg Asp
    275                 280                 285

Ile Glu Ser Asp Lys Ser Ile Ser Ala Asn Val Ile Asp Ile Pro Ser
290                 295                 300

Met Pro Glu Gln Thr Trp Pro Asn Met Tyr Gly Phe Asn Ala Lys Arg
305                 310                 315                 320

Leu Lys Glu Thr Tyr Ser Ser Tyr Glu Gly Asp Val Ala Thr Pro Ile
            325                 330                 335

Phe Asp Tyr Ile Tyr Thr Tyr Lys Ala Leu Thr Ser Met Ala Thr Pro
        340                 345                 350

Ser Thr Glu Ala Gln Val Ala Val Tyr Leu Asn Pro Ser Thr Asp Arg
    355                 360                 365

Leu Val Ile Leu Ala Asn Gly Ile Thr His Leu Ser Met Tyr Asp Leu
370                 375                 380

Gln Gly Lys Leu Ile Arg Asp Cys Ala Leu Ser Gly Asp Lys Val Glu
385                 390                 395                 400

Met Gly Val Gly Ser Leu Thr Lys Gly Thr Tyr Leu Leu Lys Val Asn
            405                 410                 415

Thr Asp Gln Gly Ala Phe Val Arg Lys Val Val Phe Asp Asp Arg Ala
        420                 425                 430

Ser Pro Gln Pro Trp Arg Tyr Arg Ile Arg Ile Arg Ala Pro Ser Thr
    435                 440                 445

Ser Leu Arg Pro His Ser Ser Thr Thr Thr Thr Thr Glu Ile Arg
450                 455                 460

Leu Leu Thr Lys Pro Glu Arg Lys Leu Ser Trp Leu Leu Pro Pro Leu
465                 470                 475                 480

Ser Asn Asn

<210> SEQ ID NO 36
<211> LENGTH: 1449
<212> TYPE: DNA
<213> ORGANISM: Artificial Sequence
<220> FEATURE:
<223> OTHER INFORMATION: Synthetic Construct (PG1798 of P.gingivalis
      strain W50)

<400> SEQUENCE: 36
atgcaccatc atcatcatca ttcttctggt ctggtgccac gcggttctgg tatgaaagaa      60
accgctgctg ctaaattcga acgccagcac atggacagcc agatctgggt accgatgac     120 gacgacaaga tgcaaaccaa ggacaattct tcttacaaac ttttttcgaa agaagatatt    180
gccggaggag tttactctct cccgactcaa atcgtgcgc agaaggacaa tgccgagtgg    240
cttcttacag cgaccgtctc cacaaaccag tctgcagata tcactttat cttcgatgag    300 aacaaccgct atatcgctcg tgacataaaa gccaatgggg taagaaaatc cacggactcc    360
atttactacg atgccaacgg gcgaatatcg catgtggatc tttatatctc gttcagtggc    420
ggagagcctg cactcgacac ccgattcaag tacacctatg atgacgaggg aaagatgacc    480
gtgagggaag tattcatgct ggtaatggat ccgaatacac ctatctcacg cttggaatat    540
```

```
cattatgatg cacagggcag actgacccac tggatttctt ttgctttcgg ggcagaatcc    600
caaaagaata cgtatcacta taatgaaaaa ggtctgttgg tcagcgaagt gctgagcaat    660
gcaatgggga caacctattc agacaccggc aaaacggaat acagctatga cgatgcagat    720
aatatggtga aggccgagta cttcgtcgtc cagcaaggaa aggcatggca agtactcaaa    780
agagaggaat acacctatga ggacaatatc tgcatacaat atttggctat taacggtacc    840
gacacaaagg tgtacaagcg agacatcgag agcgataagt ccatctccgc aaatgtcatt    900
gacattccgt caatgccgga acagacctgg cctaatatgt acggattcaa cgcaaagcga    960
ctgaaagaga cttattcctc ctacgaagga gatgtggcta ctcctatatt cgactatatc   1020
tatacgtaca aggctcttac ctcaatggca acaccttcga cagaagctca ggtagcagtc   1080
tatctcaatc cgtcaacgga ccggttagtg attctggcca acggcatcac acatctgagc   1140
atgtacgact gcagggtaa gcttatccgt gattgtgcct tgagcggcga taaggtggaa   1200
atgggtgtcg atctttgac caaagggaca tacctgctta aagtgaatac ggatcaggga   1260
gcctttgtga gaaaagtcgt gttcgatgac cgggcttctc ctcaaccatg gcgatatcgg   1320
atccgaattc gagctccgtc gacaagcttg cggccgcact cgagcaccac caccaccacc   1380
actgagatcc ggctgctaac aaagcccgaa aggaagctga gttggctgct gccaccgctg   1440
agcaataac                                                            1449

<210> SEQ ID NO 37
<211> LENGTH: 526
<212> TYPE: PRT
<213> ORGANISM: Artificial Sequence
<220> FEATURE:
<223> OTHER INFORMATION: Synthetic Construct (PG0186 of P. gingivalis
      strain W50)

<400> SEQUENCE: 37
```

Met His His His His His Ser Ser Gly Leu Val Pro Arg Gly Ser
1               5                   10                  15

Gly Met Lys Glu Thr Ala Ala Lys Phe Glu Arg Gln His Met Asp
                20                  25                  30

Ser Pro Asp Leu Gly Thr Asp Asp Asp Lys Met Cys Glu Leu Asp
            35                  40                  45

Arg Asp Pro Glu Gly Lys Asp Phe Gln Gln Pro Tyr Thr Ser Phe Val
50                  55                  60

Gln Thr Lys Gln Asn Arg Asp Gly Leu Tyr Ala Leu Leu Arg Asn Thr
65                  70                  75                  80

Glu Asn Pro Arg Met His Phe Tyr Gln Glu Leu Gln Ser Asp Met Tyr
                85                  90                  95

Cys Thr Thr Ile Thr Asp Gly Asn Ser Leu Ala Pro Phe Val Asn Trp
            100                 105                 110

Asp Leu Gly Ile Leu Asn Asp His Gly Arg Ala Asp Glu Asp Glu Val
        115                 120                 125

Ser Gly Ile Ala Gly Tyr Tyr Phe Val Tyr Asn Arg Leu Asn Gln Gln
    130                 135                 140

Ala Asn Ala Phe Val Asn Asn Thr Glu Ala Ala Leu Gln Asn Gln Val
145                 150                 155                 160

Tyr Lys Asn Ser Thr Glu Ile Ala Asn Ala Lys Ser Phe Leu Ala Glu
                165                 170                 175

Gly Lys Val Leu Gln Ala Leu Ala Ile Trp Arg Leu Met Asp Arg Phe
            180                 185                 190

```
Ser Phe His Glu Ser Val Thr Glu Val Asn Ser Gly Ala Lys Asp Leu
        195                 200                 205
Gly Val Ile Leu Leu Lys Glu Tyr Asn Pro Gly Tyr Ile Gly Pro Arg
    210                 215                 220
Ala Thr Lys Ala Gln Cys Tyr Asp Tyr Ile Leu Ser Arg Leu Ser Glu
225                 230                 235                 240
Ala Ile Glu Val Leu Pro Glu Asn Arg Glu Ser Val Leu Tyr Val Ser
                245                 250                 255
Arg Asp Tyr Ala Tyr Ala Leu Arg Ala Arg Ile Tyr Leu Ala Leu Gly
            260                 265                 270
Glu Tyr Gly Lys Ala Ala Asp Ala Lys Met Val Val Asp Lys Tyr
        275                 280                 285
Pro Leu Ile Gly Ala Ala Asp Ala Ser Glu Phe Glu Asn Ile Tyr Arg
    290                 295                 300
Ser Asp Ala Asn Asn Pro Glu Ile Ile Phe Arg Gly Phe Ala Ser Ala
305                 310                 315                 320
Thr Leu Gly Ser Phe Thr Ala Thr Thr Leu Asn Gly Ala Ala Pro Ala
                325                 330                 335
Gly Lys Asp Ile Lys Tyr Asn Pro Ser Ala Val Pro Phe Gln Trp Val
            340                 345                 350
Val Asp Leu Tyr Glu Asn Glu Asp Phe Arg Lys Ser Val Tyr Ile Ala
        355                 360                 365
Lys Val Val Lys Asp Lys Gly Tyr Leu Val Asn Lys Phe Leu Glu
    370                 375                 380
Asp Lys Ala Tyr Arg Asp Val Gln Asp Lys Pro Asn Leu Lys Val Gly
385                 390                 395                 400
Ala Arg Tyr Phe Ser Val Ala Glu Val Tyr Leu Ile Leu Val Glu Ser
                405                 410                 415
Ala Leu Gln Thr Gly Asp Thr Pro Thr Ala Glu Lys Tyr Leu Lys Ala
            420                 425                 430
Leu Ser Lys Ala Arg Gly Ala Glu Val Ser Val Val Asn Met Glu Ala
        435                 440                 445
Leu Gln Ala Glu Arg Thr Arg Glu Leu Ile Gly Glu Gly Ser Arg Leu
    450                 455                 460
Arg Asp Met Val Arg Trp Ser Ile Pro Asn Asn His Asp Ala Phe Glu
465                 470                 475                 480
Thr Gln Pro Gly Leu Glu Gly Phe Ala Asn Thr Thr Pro Leu Lys Ala
                485                 490                 495
Gln Ala Pro Val Gly Phe Tyr Ala Tyr Thr Trp Glu Phe Pro Gln Arg
            500                 505                 510
Asp Arg Gln Thr Asn Pro Gln Leu Ile Lys Asn Trp Pro Ile
        515                 520                 525

<210> SEQ ID NO 38
<211> LENGTH: 1581
<212> TYPE: DNA
<213> ORGANISM: Artificial Sequence
<220> FEATURE:
<223> OTHER INFORMATION: Synthetic Construct (PG0186 of P. gingivalis
      strain W50)

<400> SEQUENCE: 38
atgcaccatc atcatcatca ttcttctggt ctggtgccac gcggttctgg tatgaaagaa      60
accgctgctg ctaaattcga acgccagcac atggacagcc agatctggg taccgatgac     120
```

```
gacgacaaga tgtgcgagct tgaccgcgac cccgaaggaa aagatttcca acagccatat    180
acttctttcg tgcagacgaa acaaaacaga gatggtcttt acgcacttttt gcgtaatact   240 gaaaatccac gaatgcattt ttatcaggaa cttcaatccg atatgtattg cactaccatt    300
actgatggta actccttagc tccgttcgtg aattgggatt taggcatact aacgaccat    360 ggacgtgctg atgaggacga agtctccggt atagctggct actatttcgt atacaatcga   420
ctaaatcagc aagcgaatgc ttttgttaac aatacggaag ctgcgttgca gaatcaagtg    480
tataaaaatt ccaccgagat cgccaatgct aagagctttt ggcggaagg aaaagttta    540 caagcattgg ctatttggcg actgatggat cgttttagct ccatgaaag cgtgacagaa    600 gttaattccg gtgcgaaaga tcttggcgtt attctgttga agaatataa tcctggttat    660 atcggtcccc gtgcaacgaa ggcacaatgt tatgattaca tttttgtcacg tttgtctgag   720 gctattgaag ttttgcccga aacagggaa agcgttcttt atgtgagccg tgattacgcc    780
tatgccctcc gagcaagaat ttacctcgcg ttgggtgaat atggaaaagc tgcagcagat    840
gctaagatgg ttgttgataa gtatcctttg attggtgcag cagatgcttc tgagtttgag    900
aatatttatc gatcagatgc taataatccc gaaattattt ttcgtggttt tgcttctgcg    960
actcttggct cgtttactgc tacgacacta atggtgctg cgccagcagg taaggatata   1020
aaatataatc cgagcgcagt cccttttccaa tgggtagtgg atctttatga aaacgaagat   1080
ttccgcaaat ccgtatatat cgcgaaagtt gtgaaaaagg ataaggggta tttagtaaat   1140
aaattccttg aggacaaggc ttatcgtgat gttcaggata agccaaacct taaagtcgga   1200
gctcgttatt ttagcgttgc tgaggtctac ttaattttgg tagagtctgc tcttcagact   1260 ggagatacccc aacagccga aaaatatctc aaggctttga gtaaagctcg tggagcagaa   1320
gtttcagtcg ttaatatgga agcactgcaa gcagagcgta cgcgtgagct tataggtgag   1380
ggtagtcgtt tgcgtgatat ggtccgctgg agtatcccta ataatcatga tgcttttgag   1440
actcagcctg gtttagaagg ttttgcaaat actactcctt tgaaagctca agctcctgta   1500
ggcttttatg catatacttg ggagttccca cagcgagatc gacaaactaa tccgcagtta   1560
ataaagaact ggccgatata a                                              1581

<210> SEQ ID NO 39
<211> LENGTH: 396
<212> TYPE: PRT
<213> ORGANISM: Artificial Sequence
<220> FEATURE:
<223> OTHER INFORMATION: Synthetic Construct (PG1326 of P.gingivalis
      strain W50)

<400> SEQUENCE: 39

Met His His His His His Ser Ser Gly Leu Val Pro Arg Gly Ser
1               5                   10                  15

Gly Met Lys Glu Thr Ala Ala Lys Phe Glu Arg Gln His Met Asp
                20                  25                  30

Ser Pro Asp Leu Gly Thr Asp Asp Asp Lys Met Leu Cys Glu Asn
            35                  40                  45

Thr Leu Ala Gln Gln Lys Thr Glu Glu Phe Ala Pro Val Ser Asp Leu
50                  55                  60

Arg Ala Glu Ala Tyr Gly Ser Thr Val Phe Leu His Trp Thr Pro Pro
65                  70                  75                  80

Tyr Asp Asn Pro Met Ile Pro Leu Ser Glu Ser Phe Glu Ser Gly Ile
                85                  90                  95
```

```
Pro Ala Ile Trp Lys Thr Ile Asp Ala Asp Gly Asp Gly Tyr Asn Trp
                100                 105                 110

Met His Leu Thr Asn Phe Thr Gly Gln Ser Gly Leu Cys Val Ser Ser
            115                 120                 125

Ala Ser Tyr Ile Gly Gly Val Gly Ala Leu Thr Pro Asp Asn Tyr Leu
        130                 135                 140

Ile Thr Pro Glu Leu Lys Leu Pro Thr Asp Ala Leu Val Glu Ile Ile
145                 150                 155                 160

Tyr Trp Val Cys Thr Gln Asp Leu Thr Ala Pro Ser Glu His Tyr Ala
                165                 170                 175

Val Tyr Ser Ser Thr Gly Asn Asn Ala Ala Asp Phe Val Asn Leu
            180                 185                 190

Leu Tyr Glu Glu Thr Leu Thr Ala Lys Arg Ile Gln Ser Pro Glu Leu
            195                 200                 205

Ile Arg Gly Asn Arg Thr Gln Gly Val Trp Tyr Gln Arg Lys Val Val
        210                 215                 220

Leu Pro Asn Asp Thr Lys Tyr Val Ala Phe Arg His Phe Asn Ser Thr
225                 230                 235                 240

Asp Asn Phe Trp Leu Asn Leu Asp Glu Val Ser Ile Leu Tyr Thr Pro
                245                 250                 255

Leu Pro Arg Arg Ala Pro Cys Pro His Pro Gly Gly Tyr Thr Tyr Ser
            260                 265                 270

Val Phe Arg Asp Gly Gln Lys Ile Ala Ser Gly Leu Ser Ala Leu Ala
        275                 280                 285

Tyr Ile Asp Thr Asp Val Pro Tyr Gly Thr Gln Asp Tyr Cys Val Gln
290                 295                 300

Val Asn Tyr Leu Gln Gly Asp Ser Tyr Lys Val Cys Lys Asn Ile Val
305                 310                 315                 320

Val Ala Asn Ser Ala Asn Ile Tyr Gly Ala Asp Lys Pro Phe Ala Leu
                325                 330                 335

Thr Val Val Gly Lys Thr Ile Val Ala Ser Ala Phe Lys Gly Glu Ile
            340                 345                 350

Thr Leu Tyr Asp Ile Arg Gly Arg Leu Ile Ala Ser Gly Cys Asp Thr
        355                 360                 365

Leu Arg Tyr Lys Ala Glu Asn Gly Phe Tyr Leu Ile Lys Ile Gln Val
        370                 375                 380

Asn Gly Thr Val Tyr Thr Glu Lys Ile Gln Ile Gln
385                 390                 395

<210> SEQ ID NO 40
<211> LENGTH: 1191
<212> TYPE: DNA
<213> ORGANISM: Artificial Sequence
<220> FEATURE:
<223> OTHER INFORMATION: Synthetic Construct (PG1326 of P. gingivalis
      strain W50)

<400> SEQUENCE: 40
atgcaccatc atcatcatca ttcttctggt ctggtgccac gcggttctgg tatgaaagaa      60
accgctgctg ctaaattcga acgccagcac atggacagcc agatctgggt accgatgac     120 gacgacaaga tgttgtgtga aaataccctt gcacaacaaa aaacagagga gtttgcacct    180
gtgtcggatt acgtgcagag agcgtacggc tctaccgttt tcctccactg gactccgccg    240
tatgacaatc gatgattcc tctaagcgag agttttgaat caggtattcc agctatatgg    300
aagaccattg acgcagatgg cgatggctat aattggatgc atttgaccaa tttcacggga    360
```

-continued

```
cagagtggtc tctgtgtctc ttcggcttca tacataggcg gcgtcggagc tttgactccg    420
gacaattatc tgataacacc cgaattaaaa ctacccacag acgcgttggt ggaaataatc    480
tattgggtat gtactcaaga tctcactgct ccatcggagc actatgccgt ttattcctct    540
tctacaggca ataatgctgc tgactttgtt aatctcttat atgaagagac tttgactgcc    600
aaacggatac aatcccccga gttgatccgc ggaaatcgga cacaaggtgt ttggtatcaa    660
agaaaggtgg tactccctaa cgatactaaa tatgttgctt ccgccatttt aattccacg     720 gataatttct ggctcaattt ggatgaagta tctatcctgt ataccectct ccccgaaga     780 gctccgtgtc cgcatccggg tggttacact tattctgtat ccgtgatgg acaaaagata    840 gcgagtggat tgtcggcatt ggcatatatc gatacggatg taccgtatgg gactcaagac    900
tattgtgtcc aagtcaatta tctgcaagga gactcgtata agtctgcaa aaatatagtg     960 gtggcaaatt ctgcaaacat ctatggggcg gataagcctt ttgcgttgac cgtggttggc   1020
aagaccattg tagcgagtgc tttcaaagga gagatcactc tttatgacat tcgtggccgg   1080
ctgatagctt ccggctgcga tacgcttagg tacaaagcgg aaaatggttt ttacctcatt   1140
aaaatacagg taaacggaac tgtctatact gagaaaatcc aaatccaata a            1191
```

<210> SEQ ID NO 41
<211> LENGTH: 6770
<212> TYPE: DNA
<213> ORGANISM: Artificial Sequence
<220> FEATURE:
<223> OTHER INFORMATION: Synthethic Construct (plasmid vector with insert of PG0495 of P.gingivalis W50)

<400> SEQUENCE: 41

```
atgcaccatc atcatcatca ttcttctggt ctggtgccac gcggttctgg tatgaaagaa     60
accgctgctg ctaaattcga acgccagcac atggacagcc cagatctggg taccgatgac    120
gacgacaagt tgcagacaat ggctccaaat tacttccatg ccgatccgca gcaattcaaa    180
cacaggattg taaaagaaaa aagcttctcc tcctactcta attacgaata cggagtcgac    240
aaccgtctgc aaaggatcta ttcggtggat gagtcttcgg gagagatcga acacgaaaga    300
cgattctttt tcaatgaagg cggatatatg attcgtgagg aggaatacga tggaaccgtt    360
cagatacctg tcagaaaatg ggaatttgtc cgcgatgaca agggttatat cactcatttc    420
agcagatact cgcctaaaga tggaagtcag gagttgatag aggatatccg tatcgatttt    480
tcctacgatg ccgatatgaa actgatcaaa gcggatatag atttcttcga cattatggcc    540
aatgtatggg gcgatctgcg cacgacaaaa ctagtctata atgaaaacgg actcttgaaa    600
gagatgattc aaaccgatcc gggaagtgga caagaattca atcgggaaga gcttacatac    660
aataacctca acaaaatagt tgctatcagg tttataccgg gaccggccag tacaggtttg    720
aacgaatttg aattgatata cgaatacgac agtgaaggaa tggatattgt caaagccggg    780
cgtgacgatt tctggtacta ctatgagtac gacaaagaaa tgctcgcttc agagacattc    840
ttcccaaagc cttccatagc ggatttagta tatttcggac ttaaagatta tgtggatttt    900
tcaggactac ccttcaaaaa cagttatact catgtagtag tcaaagaatc tacaaatgaa    960
gtggaagcga tttatgaacc tatctctgta tattccgtag tggtcatcca gcccgaaaat   1020
ggagagataa agctaacggc cgatgggcag cccctgaaca gcggttccac attagtggca   1080
ggccgtcgta ttaaaataca tcccatccct gccgaaggtt acgaagtgga caaggtaatg   1140
gtgaacggag agaatatcga agctccgtat gaattccttc ttgagaaaga tacagaagtg   1200
```

```
acagccctga tgaagaagag caatgccgta ggagaagtcg acaccaaagg cttccatgtc    1260
tatcccatac ccacatcaaa agatttgacg atagagatac cggcagaaat ggtaggcaaa    1320
gtggcatctc ttatagatat gaacggacag attgtttaca gagttacgct taataacatc    1380
ttccagcaga tagatatcag ccatctcaag gcgttttcc tcttgcagat cggtgatatt     1440
cagaaagagt gatcgttcaa taaccgggct tctcctcaac catggcgata tcggatccga    1500
attcgagctc cgtcgacaag cttgcggccg cactcgagca ccaccaccac caccactgag    1560
atccggctgc taacaaagcc cgaaaggaag ctgagttggc tgctgccacc gctgagcaat    1620
aactagcata accccttggg gcctctaaac gggtcttgag ggttttttg ctgaaaggag     1680 gaactatatc cggattggcg aatgggacgc gccctgtagc ggcgcattaa gcgcggcggg    1740
tgtggtggtt acgcgcagcg tgaccgctac acttgccagc gccctagcgc ccgctccttt    1800
cgctttcttc ccttcctttc tcgccacgtt cgccggcttt ccccgtcaag ctctaaatcg    1860
ggggctccct ttagggttcc gatttagtgc tttacggcac ctcgacccca aaaaacttga    1920
ttagggtgat ggttcacgta gtgggccatc gccctgatag acggttttc gccctttgac     1980 gttggagtcc acgttcttta atagtggact cttgttccaa actggaacaa cactcaaccc    2040
tatctcggtc tattctttg atttataagg gattttgccg atttcggcct attggttaaa    2100
aaatgagctg atttaacaaa aatttaacgc gaattttaac aaaatattaa cgtttacaat    2160
ttcaggtggc acttttcggg gaaatgtgcg cggaacccct atttgtttat ttttctaaat    2220
acattcaaat atgtatccgc tcatgaatta attcttagaa aaactcatcg agcatcaaat    2280
gaaactgcaa tttattcata tcaggattat caataccata ttttgaaaa agccgtttct     2340 gtaatgaagg agaaaactca ccgaggcagt tccataggat ggcaagatcc tggtatcggt    2400
ctgcgattcc gactcgtcca acatcaatac aacctattaa tttcccctcg tcaaaaataa    2460
ggttatcaag tgagaaatca ccatgagtga cgactgaatc cggtgagaat ggcaaaagtt    2520
tatgcatttc tttccagact tgttcaacag gccagccatt acgctcgtca tcaaaatcac    2580
tcgcatcaac caaaccgtta ttcattcgtg attgcgcctg agcgagacga atacgcgat    2640 cgctgttaaa aggacaatta caaacaggaa tcgaatgcaa ccggcgcagg aacactgcca    2700
gcgcatcaac aatattttca cctgaatcag gatattcttc taatacctgg aatgctgttt    2760
tcccggggat cgcagtggtg agtaaccatg catcatcagg agtacggata aaatgcttga    2820
tggtcggaag aggcataaat tccgtcagcc agtttagtct gaccatctca tctgtaacat    2880
cattggcaac gctacctttg ccatgtttca gaaacaactc tggcgcatcg gcttcccat    2940 acaatcgata gattgtcgca cctgattgcc cgacattatc gcgagcccat ttatacccat    3000
ataaatcagc atccatgttg gaatttaatc gcggcctaga gcaagacgtt tcccgttgaa    3060
tatggctcat aacacccctt gtattactgt ttatgtaagc agacagtttt attgttcatg    3120
accaaaatcc cttaacgtga gttttcgttc cactgagcgt cagacccgt agaaaagatc      3180 aaaggatctt cttgagatcc ttttttttctg cgcgtaatct gctgcttgca acaaaaaaa    3240 ccaccgctac cagcggtggt ttgtttgccg gatcaagagc taccaactct ttttccgaag    3300
gtaactggct tcagcagagc gcagatacca atactgtcc ttctagtgta gccgtagtta    3360
ggccaccact tcaagaactc tgtagcaccg cctacatacc tcgctctgct aatcctgtta    3420
ccagtggctg ctgccagtgg cgataagtcg tgtcttaccg ggttggactc aagacgatag    3480
ttaccggata aggcgcagcg gtcgggctga acggggggtt cgtgcacaca gcccagcttg    3540
```

```
gagcgaacga cctacaccga actgagatac ctacagcgtg agctatgaga aagcgccacg    3600
cttcccgaag ggagaaaggc ggacaggtat ccggtaagcg gcagggtcgg aacaggagag    3660
cgcacgaggg agcttccagg gggaaacgcc tggtatcttt atagtcctgt cgggtttcgc    3720
cacctctgac ttgagcgtcg atttttgtga tgctcgtcag gggggcggag cctatggaaa    3780
aacgccagca acgcggcctt tttacggttc ctggccttttt gctggccttt tgctcacatg    3840
ttctttcctg cgttatcccc tgattctgtg gataaccgta ttaccgcctt tgagtgagct    3900
gataccgctc gccgcagccg aacgaccgag cgcagcgagt cagtgagcga ggaagcggaa    3960
gagcgcctga tgcggtattt tctccttacg catctgtgcg gtatttcaca ccgcatatat    4020
ggtgcactct cagtacaatc tgctctgatg ccgcatagtt aagccagtat acactccgct    4080
atcgctacgt gactgggtca tggctgcgcc ccgacacccg ccaacacccg ctgacgcgcc    4140
ctgacgggct tgtctgctcc cggcatccgc ttacagacaa gctgtgaccg tctccgggag    4200
ctgcatgtgt cagaggtttt caccgtcatc accgaaacgc gcgaggcagc tgcggtaaag    4260
ctcatcagcg tggtcgtgaa gcgattcaca gatgtctgcc tgttcatccg cgtccagctc    4320
gttgagtttc tccagaagcg ttaatgtctg gcttctgata aagcgggcca tgttaagggc    4380
ggttttttcc tgtttggtca ctgatgcctc cgtgtaaggg ggatttctgt tcatgggggt    4440
aatgataccg atgaaacgag agaggatgct cacgatacgg gttactgatg atgaacatgc    4500
ccggttactg gaacgttgtg agggtaaaca actggcggta tggatgcggc gggaccagag    4560
aaaaatcact cagggtcaat gccagcgctt cgttaataca gatgtaggtg ttccacaggg    4620
tagccagcag catcctgcga tgcagatccg gaacataatg gtgcagggcg ctgacttccg    4680
cgtttccaga ctttacgaaa cacggaaacc gaagaccatt catgttgttg ctcaggtcgc    4740
agacgttttg cagcagcagt cgcttcacgt tcgctcgcgt atcggtgatt cattctgcta    4800
accagtaagg caaccccgcc agcctagccg ggtcctcaac gacaggagca cgatcatgcg    4860
cacccgtggg gccgccatgc cggcgataat ggcctgcttc tcgccgaaac gtttggtggc    4920
gggaccagtg acgaaggctt gagcgagggc gtgcaagatt ccgaataccg caagcgacag    4980
gccgatcatc gtcgcgctcc agcgaaagcg gtcctcgccg aaaatgaccc agagcgctgc    5040
cggcacctgt cctacgagtt gcatgataaa gaagacagtc ataagtgcgg cgacgatagt    5100
catgccccgc gcccaccgga aggagctgac tgggttgaag gctctcaagg gcatcggtcg    5160
agatcccggt gcctaatgag tgagctaact tacattaatt gcgttgcgct cactgcccgc    5220
tttccagtcg ggaaacctgt cgtgccagct gcattaatga atcggccaac gcgcggggag    5280
aggcggtttg cgtattgggc gccagggtgg ttttctcttt caccagtgag acgggcaaca    5340
gctgattgcc cttcaccgcc tggccctgag agagttgcag caagcggtcc acgctggttt    5400
gccccagcag gcgaaaatcc tgtttgatgg tggttaacgg cgggatataa catgagctgt    5460
cttcggtatc gtcgtatccc actaccgaga tgtccgcacc aacgcgcagc ccggactcgg    5520
taatggcgcg cattgcgccc agcgccatct gatcgttggc aaccagcatc gcagtgggaa    5580
cgatgccctc attcagcatt tgcatggttt gttgaaaacc ggacatggca ctccagtcgc    5640
cttcccgttc cgctatcggc tgaatttgat tgcgagtgag atatttatgc cagccagcca    5700
gacgcagacg cgccgagaca gaacttaatg ggcccgctaa cagcgcgatt tgctggtgac    5760
ccaatgcgac cagatgctcc acgcccagtc gcgtaccgtc ttcatgggag aaaataatac    5820
tgttgatggg tgtctggtca gagacatcaa gaaataacgc cggaacatta gtgcaggcag    5880
cttccacagc aatggcatcc tggtcatcca gcggatagtt aatgatcagc ccactgacgc    5940
```

```
gttgcgcgag aagattgtgc accgccgctt tacaggcttc gacgccgctt cgttctacca      6000
tcgacaccac cacgctggca cccagttgat cggcgcgaga tttaatcgcc gcgacaattt      6060
gcgacggcgc gtgcagggcc agactggagg tggcaacgcc aatcagcaac gactgtttgc      6120
ccgccagttg ttgtgccacg cggttgggaa tgtaattcag ctccgccatc gccgcttcca      6180
cttttttccg cgttttcgca gaaacgtggc tggcctggtt caccacgcgg gaaacggtct      6240
gataagagac accggcatac tctgcgacat cgtataacgt tactggtttc acattcacca      6300
ccctgaattg actctcttcc gggcgctatc atgccatacc gcgaaaggtt ttgcgccatt      6360
cgatggtgtc cgggatctcg acgctctccc ttatgcgact cctgcattag gaagcagccc      6420
agtagtaggt tgaggccgtt gagcaccgcc gccgcaagga atggtgcatg caaggagatg      6480
gcgcccaaca gtccccggc cacggggcct gccaccatac ccacgccgaa acaagcgctc      6540
atgagcccga gtggcgagc ccgatcttcc ccatcggtga tgtcggcgat ataggcgcca      6600
gcaaccgcac ctgtggcgcc ggtgatgccg ccacgatgc gtccggcgta gaggatcgag      6660
atcgatctcg atcccgcgaa attaatacga ctcactatag gggaattgtg agcggataac      6720
aattcccctc tagaaataat tttgtttaac tttaagaagg agatatacat                6770

<210> SEQ ID NO 42
<211> LENGTH: 6411
<212> TYPE: DNA
<213> ORGANISM: Artificial Sequence
<220> FEATURE:
<223> OTHER INFORMATION: Synthethic Construct (plasmid vector with
      insert of PG0616 of P.gingivalis W50)

<400> SEQUENCE: 42
atgcaccatc atcatcatca ttcttctggt ctggtgccac gcggttctgg tatgaaagaa        60
accgctgctg ctaaattcga acgccagcac atggacagcc agatctgggt accgatgac       120 gacgacaaga tgcaagagtt gaaaacctct gctgacatga aggttcttt taagaagaat       180 gtggtattgg aggtatttac tgccgaatgg tgcggttact gtccaggtgg aaaagagcgc       240
attgcaaaag caattgaaat gttggatgat gaatataagg agcgtgtttt tcagacattt       300
gttcattata atgatgggat ctcaaaaaaa tggcctcgtg ttggccaact tttcattgca       360
ttggatcaaa cattgggcat tccgggtttt ccgactttt cagtttgccg tatggagaaa       420
aaaggtgaaa tctttcaat aggtgctcca atagcaatta aaataagat tatgaaaggt       480 tttggtgatg gtacagcccc tgcagaggta aaccttaaat tgaccaaagg tgcaacaccg       540
gaagatgtat gtacagctac atttactggt aaagtcgatg ctgacctcat agggaaacct       600
cttatgttga ctgcatatgt attgaaaaac aatatgaagc ctattaatcc gcaaaatgga       660
gctggggatg gatatctcca ccaacatact gtgttaatga ttctctccac agatgtaaaa       720
ggagacgctt taaatattgc agccgatgga agttttacca tcaagaaaga atttaagttg       780
gatggctttg aaattaaaga tacagatgtt cttgcttttcg tacaccatcc aatgtccaat       840
gcggaaaacc attctattat caatgccggg caagaaagcc ttgataaagc agagcctaca       900
gctacagaac aaattgttgc taccccctct gtcaaagcat atgttcagaa tggcaaaatt       960
gttgtagagg aagagtattc aagatggaa gtattcaatg caactggtca acttgtcaaa      1020
aatgaatccc ttgtccccgg tgtctatgtt gtccgtataa cggcaaacgg tgtaatgtat      1080
ttccttaaag tcttggttcc ttgaccgggc ttctcctcaa ccatggcgat atcggatccg      1140
aattcgagct ccgtcgacaa gcttgcggcc gcactcgagc accaccacca ccaccactga      1200
```

```
gatccggctg ctaacaaagc ccgaaaggaa gctgagttgg ctgctgccac cgctgagcaa    1260
taactagcat aaccccttgg ggcctctaaa cgggtcttga ggggttttt gctgaaagga     1320
ggaactatat ccggattggc gaatgggacg cgccctgtag cggcgcatta agcgcggcgg    1380
gtgtggtggt tacgcgcagc gtgaccgcta cacttgccag cgccctagcg cccgctcctt    1440
tcgctttctt cccttccttt ctcgccacgt tcgccggctt tccccgtcaa gctctaaatc    1500
gggggctccc tttagggttc cgatttagtg ctttacggca cctcgacccc aaaaaacttg    1560
attagggtga tggttcacgt agtgggccat cgccctgata cggttttt cgccctttga     1620
cgttggagtc cacgttcttt aatagtggac tcttgttcca aactggaaca cactcaacc     1680
ctatctcggt ctattctttt gatttataag gattttgcc gatttcggcc tattggttaa     1740
aaaatgagct gatttaacaa aaatttaacg cgaattttaa caaatatta acgtttacaa     1800
tttcaggtgg cacttttcgg ggaaatgtgc gcggaacccc tatttgttta tttttctaaa    1860
tacattcaaa tatgtatccg ctcatgaatt aattcttaga aaaactcatc gagcatcaaa    1920
tgaaactgca atttattcat atcaggatta tcaataccat atttttgaaa aagccgtttc    1980
tgtaatgaag gagaaaactc accgaggcag ttccatagga tggcaagatc ctggtatcgg    2040
tctgcgattc cgactcgtcc aacatcaata caacctatta atttcccctc gtcaaaaata    2100
aggttatcaa gtgagaaatc accatgagtg acgactgaat ccggtgagaa tggcaaaagt    2160
ttatgcatt ctttccagac ttgttcaaca ggccagccat tacgctcgtc atcaaaatca     2220
ctcgcatcaa ccaaaccgtt attcattcgt gattgcgcct gagcgagacg aaatacgcga    2280
tcgctgttaa aaggacaatt acaaacagga atcgaatgca accggcgcag gaacactgcc    2340
agcgcatcaa caatattttc acctgaatca ggatattctt ctaatacctg gaatgctgtt    2400
ttcccgggga tcgcagtggt gagtaaccat gcatcatcag gagtacggat aaaatgcttg    2460
atggtcggaa gaggcataaa ttccgtcagc cagtttagtc tgaccatctc atctgtaaca    2520
tcattggcaa cgctacctt gccatgtttc agaaacaact ctggcgcatc gggcttccca     2580
tacaatcgat agattgtcgc acctgattgc ccgacattat cgcgagccca tttatccca    2640
tataaatcag catccatgtt ggaatttaat cgcggcctag agcaagacgt ttcccgttga    2700
atatggctca taacacccct tgtattactg tttatgtaag cagacagttt tattgttcat    2760
gaccaaaatc ccttaacgtg agttttcgtt ccactgagcg tcagaccccg tagaaaagat    2820
caaaggatct tcttgagatc cttttttct gcgcgtaatc tgctgcttgc aaacaaaaaa     2880
accaccgcta ccagcggtgg tttgtttgcc ggatcaagag ctaccaactc ttttccgaa     2940
ggtaactggc ttcagcagag cgcagatacc aaatactgtc cttctagtgt agccgtagtt    3000
aggccaccac ttcaagaact ctgtagcacc gcctacatac ctcgctctgc taatcctgtt    3060
accagtggct gctgccagtg gcgataagtc gtgtcttacc gggttggact caagacgata    3120
gttaccggat aaggcgcagc ggtcgggctg aacgggggt tcgtgcacac agcccagctt     3180
ggagcgaacg acctacaccg aactgagata cctacagcgt gagctatgag aaagcgccac    3240
gcttcccgaa gggagaaagg cggacaggta tccggtaagc ggcagggtcg aacaggaga     3300
gcgcacgagg gagcttccag ggggaaacgc ctggtatctt tatagtcctg tcgggtttcg    3360
ccacctctga cttgagcgtc gatttttgtg atgctcgtca gggggcgga gcctatggaa     3420
aaacgccagc aacgcggcct ttttacggtt cctggccttt tgctggcctt ttgctcacat    3480
gttctttcct gcgttatccc ctgattctgt ggataaccgt attaccgcct ttgagtgagc    3540
```

```
tgataccgct cgccgcagcc gaacgaccga gcgcagcgag tcagtgagcg aggaagcgga    3600
agagcgcctg atgcggtatt ttctccttac gcatctgtgc ggtatttcac accgcatata    3660
tggtgcactc tcagtacaat ctgctctgat gccgcatagt taagccagta tacactccgc    3720
tatcgctacg tgactgggtc atggctgcgc cccgacaccc gccaacaccc gctgacgcgc    3780
cctgacgggc ttgtctgctc ccggcatccg cttacagaca agctgtgacc gtctccggga    3840
gctgcatgtg tcagaggttt tcaccgtcat caccgaaacg cgcgaggcag ctgcggtaaa    3900
gctcatcagc gtggtcgtga agcgattcac agatgtctgc ctgttcatcc gcgtccagct    3960
cgttgagttt ctccagaagc gttaatgtct ggcttctgat aaagcgggcc atgttaaggg    4020
cggttttttc ctgtttggtc actgatgcct ccgtgtaagg gggatttctg ttcatggggg    4080
taatgatacc gatgaaacga gagaggatgc tcacgatacg ggttactgat gatgaacatg    4140
cccggttact ggaacgttgt gagggtaaac aactggcggt atggatgcgg cgggaccaga    4200
gaaaaatcac tcagggtcaa tgccagcgct tcgttaatac agatgtaggt gttccacagg    4260
gtagccagca gcatcctgcg atgcagatcc ggaacataat ggtgcagggc gctgacttcc    4320
gcgtttccag actttacgaa acacggaaac cgaagaccat tcatgttgtt gctcaggtcg    4380
cagacgtttt gcagcagcag tcgcttcacg ttcgctcgcg tatcggtgat tcattctgct    4440
aaccagtaag gcaaccccgc cagcctagcc gggtcctcaa cgacaggagc acgatcatgc    4500
gcacccgtgg ggccgccatg ccggcgataa tggcctgctt ctcgccgaaa cgtttggtgg    4560
cgggaccagt gacgaaggct tgagcgaggg cgtgcaagat tccgaatacc gcaagcgaca    4620
ggccgatcat cgtcgcgctc cagcgaaagc ggtcctcgcc gaaaatgacc cagagcgctg    4680
ccggcacctg tcctacgagt tgcatgataa agaagacagt cataagtgcg gcgacgatag    4740
tcatgccccg cgcccaccgg aaggagctga ctgggttgaa ggctctcaag gcatcggtc     4800 gagatcccgg tgcctaatga gtgagctaac ttacattaat tgcgttgcgc tcactgcccg    4860
ctttccagtc gggaaacctg tcgtgccagc tgcattaatg aatcggccaa cgcgcgggga    4920
gaggcggttt gcgtattggg cgccagggtg ttttttcttt tcaccagtga cgggcaac     4980 agctgattgc ccttcaccgc ctggccctga gagagttgca gcaagcggtc cacgctggtt    5040
tgccccagca ggcgaaaatc ctgtttgatg gtggttaacg gcgggatata acatgagctg    5100
tcttcggtat cgtcgtatcc cactaccgag atgtccgcac caacgcgcag cccggactcg    5160
gtaatggcgc gcattgcgcc cagcgccatc tgatcgttgg caaccagcat cgcagtggga    5220
acgatgccct cattcagcat ttgcatggtt tgttgaaaac cggacatggc actccagtcg    5280
ccttcccgtt ccgctatcgg ctgaatttga ttgcgagtga gatatttatg ccagccagcc    5340
agacgcagac gcgccgagac agaacttaat gggcccgcta acagcgcgat ttgctggtga    5400
cccaatgcga ccagatgctc cacgcccagt cgcgtaccgt cttcatggga gaaaataata    5460
ctgttgatgg gtgtctggtc agagacatca agaaataacg ccggaacatt agtgcaggca    5520
gcttccacag caatggcatc ctggtcatcc agcggatagt taatgatcag cccactgacg    5580
cgttgcgcga agattgtg caccgccgct ttacaggctt cgacgccgct tcgttctacc    5640
atcgacacca ccacgctggc acccagttga tcggcgcgag atttaatcgc cgcgacaatt    5700
tgcgacggcg cgtgcagggc cagactggag gtggcaacgc caatcagcaa cgactgtttg    5760
cccgccagtt gttgtgccac gcggttggga atgtaattca gctccgccat cgccgcttcc    5820
acttttcccc gcgttttcgc agaaacgtgg ctggcctggt tcaccacgcg ggaaacggtc    5880
tgataagaga caccggcata ctctgcgaca tcgtataacg ttactggttt cacattcacc    5940
```

```
acctgaatt gactctcttc cgggcgctat catgccatac cgcgaaaggt tttgcgccat    6000
tcgatggtgt ccgggatctc gacgctctcc cttatgcgac tcctgcatta ggaagcagcc    6060
cagtagtagg ttgaggccgt tgagcaccgc cgccgcaagg aatggtgcat gcaaggagat    6120 ggcgccaac agtcccccgg ccacggggcc tgccaccata cccacgccga aacaagcgct     6180
catgagcccg aagtggcgag cccgatcttc cccatcggtg atgtcggcga tataggcgcc    6240
agcaaccgca cctgtggcgc cggtgatgcc ggccacgatg cgtccggcgt agaggatcga    6300
gatcgatctc gatcccgcga attaatacg actcactata ggggaattgt gagcggataa     6360
caattcccct ctagaaataa ttttgtttaa ctttaagaag gagatataca t             6411
```

<210> SEQ ID NO 43
<211> LENGTH: 6549
<212> TYPE: DNA
<213> ORGANISM: Artificial Sequence
<220> FEATURE:
<223> OTHER INFORMATION: Synthetic Construct (plasmid vector with insert
      of PG0654 of P.gingivalis W50)

<400> SEQUENCE: 43

```
atgcaccatc atcatcatca ttcttctggt ctggtgccac gcggttctgg tatgaaagaa      60
accgctgctg ctaaattcga acgccagcac atggacagcc agatctggg taccgatgac      120 gacgacaaga tgcagtcacc ccgaatccct caagtggatg tacacactcg catcgcaaga    180
aatgcccgtt atcgactgga caagatcagt gtcccggatt ctcgtcagat attcgattac    240
ttctataaag aagaaacgat acccactaaa atacaaacga ccacaggagg tgcaattaca    300
agcatcgatt cgcttttcta tgaagacgac aggttggttc aggtgcgcta ttttgacaat    360
aaccttgaat aaaacaagc ggagaagtat gtatacgacg ttctaagct ggtccttcga     420 gaaattcgca agtcgccgac agacgaaacg ccaataaaga agttagcta tcactatctc    480 tgtggcagcg atatgccttt tgagattacg acagagatga gcgatggcta ttttgaaagc    540
catacgctta actatctgaa tggaaagatt gcccgaatag atatcatgac tcaacagaac    600
ccatcggccg aattgatcga aacgggtaga atggtatatg agtttgatgc caataatgat    660
gctgtactgc ttcgtgacag tgtatttctt cctcttcaaa acaagtgggt agaaatgttt     720 actaccgtt atacatacga caataagcat aattgtattc gttgggaaca agacgaattc     780
ggcaccctca cccttgccaa caacttcgaa tacgacacca ctatccctct gtcgtctgta    840
ttgtccccca cgcatgagga gttcttccgt cctcttcttc ccaattttat gaagcatatg    900
cgtacgaagc aaacgtattt caataactcc ggagaaggct tgtcagaggt atgcgattac    960
aactacttct ataccgatat gcagggtaat gcactgaccg atgttgccgt gaacgaatcg    1020
atcaagattt atcctcgtcc tgccacggat tttctgcgta tagaaggttc gcaactgctt    1080
cgcctttcgc tattcgacat gaacgggaag ctcatcagag ctaccgaatt gacaggcgat    1140
ttggccatta tcggagttgc atctcttccg agaggcactt acatcgcaga ataactgct     1200 gcaaacagca aaaccatacg tgcaaaagta tcgctcagat aaccgggctt ctcctcaacc    1260
atggcgatat cggatccgaa ttcgagctcc gtcgacaagc ttgcggccgc actcgagcac    1320
caccaccacc accactgaga tccggctgct aacaaagccc gaaaggaagc tgagttggct    1380
gctgccaccg ctgagcaata actagcataa ccccttgggg cctctaaacg ggtcttgagg    1440
ggttttttgc tgaaaggagg aactatatcc ggattggcga atgggacgcg ccctgtagcg    1500
gcgcattaag cgcggcgggt gtggtggtta cgcgcagcgt gaccgctaca cttgccagcg    1560
```

```
ccctagcgcc cgctcctttc gctttcttcc cttcctttct cgccacgttc gccggctttc   1620
cccgtcaagc tctaaatcgg gggctccctt tagggttccg atttagtgct ttacggcacc   1680
tcgaccccaa aaacttgat tagggtgatg gttcacgtag tgggccatcg ccctgataga   1740 cggttttcg ccctttgacg ttggagtcca cgttctttaa tagtggactc ttgttccaaa   1800
ctggaacaac actcaaccct atctcggtct attcttttga tttataaggg attttgccga   1860
tttcggccta ttggttaaaa aatgagctga tttaacaaaa atttaacgcg aattttaaca   1920
aaatattaac gtttacaatt tcaggtggca cttttcgggg aaatgtgcgc ggaacccta   1980 tttgtttatt tttctaaata cattcaaata tgtatccgct catgaattaa ttcttagaaa   2040
aactcatcga gcatcaaatg aaactgcaat ttattcatat caggattatc aataccatat   2100
ttttgaaaaa gccgtttctg taatgaagga gaaaactcac cgaggcagtt ccataggatg   2160
gcaagatcct ggtatcggtc tgcgattccg actcgtccaa catcaataca acctattaat   2220
ttcccctcgt caaaataag gttatcaagt gagaaatcac catgagtgac gactgaatcc   2280
ggtgagaatg gcaaaagttt atgcatttct ttccagactt gttcaacagg ccagccatta   2340
cgctcgtcat caaaatcact cgcatcaacc aaaccgttat tcattcgtga ttgcgcctga   2400
gcgagacgaa atacgcgatc gctgttaaaa ggacaattac aaacaggaat cgaatgcaac   2460
cggcgcagga acactgccag cgcatcaaca atattttcac ctgaatcagg atattcttct   2520
aatacctgga atgctgtttt cccggggatc gcagtggtga gtaaccatgc atcatcagga   2580
gtacggataa aatgcttgat ggtcggaaga ggcataaatt ccgtcagcca gtttagtctg   2640
accatctcat ctgtaacatc attggcaacg ctacctttgc catgtttcag aaacaactct   2700
ggcgcatcgg gcttcccata caatcgatag attgtcgcac ctgattgccc gacattatcg   2760
cgagcccatt tatacccata taaatcagca tccatgttgg aatttaatcg cggcctagag   2820
caagacgttt cccgttgaat atggctcata acacccctg tattactgtt tatgtaagca   2880
gacagtttta ttgttcatga ccaaaatccc ttaacgtgag ttttcgttcc actgagcgtc   2940 agacccgta gaaagatca aaggatcttc ttgagatcct tttttctgc gcgtaatctg   3000 ctgcttgcaa acaaaaaaac caccgctacc agcggtggtt tgtttgccgg atcaagagct   3060
accaactctt tttccgaagg taactggctt cagcagagcg cagataccaa atactgtcct   3120
tctagtgtag ccgtagttag gccaccactt caagaactct gtagcaccgc ctacatacct   3180
cgctctgcta atcctgttac cagtggctgc tgccagtggc gataagtcgt gtcttaccgg   3240
gttggactca agacgatagt taccggataa ggcgcagcgg tcgggctgaa cggggggttc   3300
gtgcacacag cccagcttgg agcgaacgac ctacaccgaa ctgagatacc tacagcgtga   3360
gctatgagaa agcgccacgc ttcccgaagg agaaaggcg acaggtatc cggtaagcgg   3420 cagggtcgga acaggagagc gcacgaggga gcttccaggg ggaaacgcct ggtatcttta   3480
tagtcctgtc gggtttcgcc acctctgact tgagcgtcga ttttgtgat gctcgtcagg   3540 ggggcggagc ctatggaaaa acgccagcaa cgcggccttt ttacggttcc tggccttttg   3600
ctggcctttt gctcacatgt tctttcctgc gttatcccct gattctgtgg ataaccgtat   3660
taccgccttt gagtgagctg ataccgctcg ccgcagccga acgaccgagc gcagcgagtc   3720
agtgagcgag gaagcggaag agcgcctgat gcggtatttt ctccttacgc atctgtgcgg   3780
tatttcacac cgcatatatg gtgcactctc agtacaatct gctctgatgc cgcatagtta   3840
agccagtata cactccgcta tcgctacgtg actgggtcat ggctgcgccc cgacacccgc   3900
```

```
caacacccgc tgacgcgccc tgacgggctt gtctgctccc ggcatccgct tacagacaag    3960
ctgtgaccgt ctccgggagc tgcatgtgtc agaggttttc accgtcatca ccgaaacgcg    4020
cgaggcagct gcggtaaagc tcatcagcgt ggtcgtgaag cgattcacag atgtctgcct    4080
gttcatccgc gtccagctcg ttgagtttct ccagaagcgt taatgtctgg cttctgataa    4140
agcgggccat gttaagggcg gttttttcct gtttggtcac tgatgcctcc gtgtaagggg    4200
gatttctgtt catggggta atgataccga tgaaacgaga gaggatgctc acgatacggg     4260
ttactgatga tgaacatgcc cggttactgg aacgttgtga gggtaaacaa ctggcggtat    4320
ggatgcggcg ggaccagaga aaaatcactc agggtcaatg ccagcgcttc gttaatacag    4380
atgtaggtgt tccacagggt agccagcagc atcctgcgat gcagatccgg aacataatgg    4440
tgcagggcgc tgacttccgc gtttccagac tttacgaaac acggaaaccg aagaccattc    4500
atgttgttgc tcaggtcgca gacgttttgc agcagcagtc gcttcacgtt cgctcgcgta    4560
tcggtgattc attctgctaa ccagtaaggc aaccccgcca gcctagccgg gtcctcaacg    4620
acaggagcac gatcatgcgc acccgtgggg ccgccatgcc ggcgataatg gcctgcttct    4680
cgccgaaacg tttggtggcg ggaccagtga cgaaggcttg agcgagggcg tgcaagattc    4740
cgaataccgc aagcgacagg ccgatcatcg tcgcgctcca gcgaaagcgg tcctcgccga    4800
aaatgaccca gagcgctgcc ggcacctgtc ctacgagttg catgataaag aagacagtca    4860
taagtgcggc gacgatagtc atgccccgcg cccaccggaa ggagctgact gggttgaagg    4920
ctctcaaggg catcggtcga gatcccggtg cctaatgagt gagctaactt acattaattg    4980
cgttgcgctc actgcccgct ttccagtcgg gaaacctgtc gtgccagctg cattaatgaa    5040
tcggccaacg cgcggggaga ggcggtttgc gtattgggcg ccagggtggt ttttcttttc    5100
accagtgaga cgggcaacag ctgattgccc ttcaccgcct ggccctgaga gagttgcagc    5160
aagcggtcca cgctggtttg ccccagcagg cgaaaatcct gtttgatggt ggttaacggc    5220
gggatataac atgagctgtc ttcggtatcg tcgtatccca ctaccgagat gtccgcacca    5280
acgcgcagcc cggactcggt aatggcgcgc attgcgccca gcgccatctg atcgttggca    5340
accagcatcg cagtgggaac gatgccctca ttcagcattt gcatggtttg ttgaaaaccg    5400
gacatggcac tccagtcgcc ttcccgttcc gctatcggct gaatttgatt gcgagtgaga    5460
tatttatgcc agccagccag acgcagacgc gccgagacag aacttaatgg gcccgctaac    5520
agcgcgattt gctggtgacc caatgcgacc agatgctcca cgcccagtcg cgtaccgtct    5580
tcatgggaga aaataatact gttgatgggt gtctggtcag agacatcaag aaataacgcc    5640
ggaacattag tgcaggcagc ttccacagca atggcatcct ggtcatccag cggatagtta    5700
atgatcagcc cactgacgcg ttgcgcgaga agattgtgca ccgccgcttt acaggcttcg    5760
acgccgcttc gttctaccat cgacaccacc acgctggcac ccagttgatc ggcgcgagat    5820
ttaatcgccg cgacaatttg cgacggcgcg tgcagggcca gactggaggt ggcaacgcca    5880
atcagcaacg actgtttgcc cgccagttgt tgtgccacgc ggttgggaat gtaattcagc    5940
tccgccatcg ccgcttccac ttttttcccgc gttttcgcag aaacgtggct ggcctggttc    6000
accacgcggg aaacggtctg ataagagaca ccggcatact ctgcgacatc gtataacgtt    6060
actggtttca cattcaccac cctgaattga ctctcttccg ggcgctatca tgccataccg    6120
cgaaaggttt tgcgccattc gatggtgtcc gggatctcga cgctctccct tatgcgactc    6180
ctgcattagg aagcagccca gtagtaggtt gaggccgttg agcaccgccg ccgcaaggaa    6240
tggtgcatgc aaggagatgg cgcccaacag tcccccggcc acggggcctg ccaccatacc    6300
```

```
cacgccgaaa caagcgctca tgagcccgaa gtggcgagcc cgatcttccc catcggtgat    6360
gtcggcgata taggcgccag caaccgcacc tgtggcgccg gtgatgccgg ccacgatgcg    6420
tccggcgtag aggatcgaga tcgatctcga tcccgcgaaa ttaatacgac tcactatagg    6480
ggaattgtga gcggataaca attcccctct agaaataatt ttgtttaact ttaagaagga    6540
gatatacat                                                           6549
```

<210> SEQ ID NO 44
<211> LENGTH: 6657
<212> TYPE: DNA
<213> ORGANISM: Artificial Sequence
<220> FEATURE:
<223> OTHER INFORMATION: Synthetic Construct (plasmid vector with insert of PG1374 of P.gingivalis W50)

<400> SEQUENCE: 44

```
atgcaccatc atcatcatca ttcttctggt ctggtgccac gcggttctgg tatgaaagaa      60
accgctgctg ctaaattcga acgccagcac atggacagcc agatctggg taccgatgac     120 gacgacaaga tgcagtttgt tccggctccc accacaggga ttcgcatgtc tgtcactaca     180
accaaggccg taggcgaaaa aatcgaattg ttggttcatt ccatagagaa gaaaggcatc     240
tggatcgatc tcaatgggga tgccacttac caacaaggag aggaaataac cgtattcgat     300
gaggcatacc acgaatacac gatcgggacg caaacccctca ctatctatgg taatacgacc    360
cgattgggct gtcgatctac cggtgcaacg gctgtcgatg taacgaaaaa ccctaatctg     420
acctatctcg catgcccgaa aaataatctg aaatcattgg acttgacgca aaacccaaag     480
ttgctgcgag tttggtgcga ctctaacgaa atagaaagtt tggacctgag tggcaatccg     540
gctttgatca tcctcggctg tgacaggaat aagctgactg agctgaagac cgataacaac     600
cccaagttgg cctctctttg gtgttctgat aataacctga cggagttgga actcagtgcc     660
aatcctcgtc tcaatgatct ttggtgcttc ggtaatcgga tcacgaaact cgatctgagt     720
gccaatcctc tattggtaac actttggtgc agtgacaatg agctttcgac cttggatctt     780
tccaagaatt cggacgttgc ttacctttgg tgttcatcga acaaacttac atccttgaat     840
ctgtcggggg tgaagggact gagtgttttg gtttgtcatt ccaatcagat cgcaggtgaa     900
gaaatgacga agtggtgaa tgctttgccc acactatctc ccggcgcagg cgctcagagc      960
aagttcgtcg ttgtagacct caaggacact gatgagaaga atatctgtac cgtaaaggat    1020
gtggaaaaag ctaaaagtaa gaactggcga gtatttgact caacggtga ttctgacaat     1080 atgcttccat acgaaggaag tccgacatcg aacttggcag tagatgctcc cactgtcagg    1140
atatatccca atccggtagg aagatatgcg ctcgtcgaga tccccgagtc tcttttaggg    1200
caggaagctg ctttatacga tatgaatggg gtaaaagtct atagtttcgc ggtagagtct    1260
cttcgtcaga acattgacct gacacatctt cccgacggca cttatttctt ccgtctcgat    1320
aactatacca ctaagctcat caaacagtaa ccgggcttct cctcaaccat ggcgatatcg    1380
gatccgaatt cgagctccgt cgacaagctt gcggccgcac tcgagcacca ccaccaccac    1440
cactgagatc cggctgctaa caaagcccga aaggaagctg agttggctgc tgccaccgct    1500
gagcaataac tagcataacc ccttggggcc tctaaacggg tcttgagggg ttttttgctg    1560
aaaggaggaa ctatatccgg attggcgaat gggacgcgcc ctgtagcggc gcattaagcg    1620
cggcgggtgt ggtggttacg cgcagcgtga ccgctacact tgccagcgcc ctagcgcccg    1680
ctcctttcgc tttcttccct tcctttctcg ccacgttcgc cggctttccc cgtcaagctc    1740
```

```
taaatcgggg gctcccttta gggttccgat ttagtgcttt acggcacctc gaccccaaaa   1800
aacttgatta gggtgatggt tcacgtagtg ggccatcgcc ctgatagacg ttttttcgcc   1860
ctttgacgtt ggagtccacg ttctttaata gtggactctt gttccaaact ggaacaacac   1920
tcaaccctat ctcggtctat tcttttgatt tataagggat tttgccgatt tcggcctatt   1980
ggttaaaaaa tgagctgatt taacaaaaat ttaacgcgaa ttttaacaaa atattaacgt   2040
ttacaatttc aggtggcact tttcggggaa atgtgcgcgg aaccccctatt tgtttatttt   2100 tctaaataca ttcaaatatg tatccgctca tgaattaatt cttagaaaaa ctcatcgagc   2160
atcaaatgaa actgcaattt attcatatca ggattatcaa taccatattt ttgaaaaagc   2220
cgtttctgta atgaaggaga aaactcaccg aggcagttcc ataggatggc aagatcctgg   2280
tatcggtctg cgattccgac tcgtccaaca tcaatacaac ctattaattt ccctcgtca    2340 aaaataaggt tatcaagtga aaatcacca tgagtgacga ctgaatccgg tgagaatggc    2400
aaaagtttat gcatttcttt ccagacttgt tcaacaggcc agccattacg ctcgtcatca   2460
aaatcactcg catcaaccaa accgttattc attcgtgatt gcgcctgagc gagacgaaat   2520
acgcgatcgc tgttaaaagg acaattacaa acaggaatcg aatgcaaccg cgcaggaac    2580 actgccagcg catcaacaat attttcacct gaatcaggat attcttctaa tacctggaat   2640
gctgttttcc cggggatcgc agtggtgagt aaccatgcat catcaggagt acggataaaa   2700
tgcttgatgg tcggaagagg cataaattcc gtcagccagt ttagtctgac catctcatct   2760
gtaacatcat tggcaacgct accttttgcca tgtttcagaa acaactctgg cgcatcgggc   2820
ttcccataca atcgatagat tgtcgcacct gattgcccga cattatcgcg agcccattta   2880
tacccatata aatcagcatc catgttggaa tttaatcgcg gcctagagca agacgtttcc   2940
cgttgaatat ggctcataac accccttgta ttactgttta tgtaagcaga cagttttatt   3000
gttcatgacc aaaatccctt aacgtgagtt ttcgttccac tgagcgtcag accccgtaga   3060
aaagatcaaa ggatcttctt gagatccttt ttttctgcgc gtaatctgct gcttgcaaac   3120
aaaaaaacca ccgctaccag cggtggtttg tttgccggat caagagctac caactctttt   3180
tccgaaggta actggcttca gcagagcgca gataccaaat actgtccttc tagtgtagcc   3240
gtagttaggc caccacttca agaactctgt agcaccgcct acatacctcg ctctgctaat   3300
cctgttacca gtggctgctg ccagtggcga taagtcgtgt cttaccgggt tggactcaag   3360
acgatagtta ccggataagg cgcagcggtc gggctgaacg gggggttcgt gcacacagcc   3420
cagcttggag cgaacgacct acaccgaact gagatacta cagcgtgagc tatgagaaag   3480
cgccacgctt cccgaaggga aaaggcgga caggtatccg gtaagcggca gggtcggaac   3540
aggagagcgc acgagggagc ttccaggggg aaacgcctgg tatctttata gtcctgtcgg   3600
gtttcgccac ctctgacttg agcgtcgatt tttgtgatgc tcgtcagggg gcggagcct    3660 atggaaaaac gccagcaacg cggcctttt acggttcctg ccttttgct ggccttttgc     3720 tcacatgttc tttcctgcgt tatcccctga ttctgtggat aaccgtatta ccgcctttga   3780
gtgagctgat accgctcgcc gcagccgaac gaccgagcgc agcgagtcag tgagcgagga   3840
agcggaagag cgcctgatgc ggtattttct ccttacgcat ctgtgcggta tttcacaccg   3900
catatatggt gcactctcag tacaatctgc tctgatgccg catagttaag ccagtataca   3960
ctccgctatc gctacgtgac tgggtcatgg ctgcgcccg acaccgcca acacccgctg     4020 acgcgccctg acgggcttgt ctgctcccgg catccgctta cagacaagct gtgaccgtct   4080
```

```
ccgggagctg catgtgtcag aggttttcac cgtcatcacc gaaacgcgcg aggcagctgc    4140
ggtaaagctc atcagcgtgg tcgtgaagcg attcacagat gtctgcctgt tcatccgcgt    4200
ccagctcgtt gagtttctcc agaagcgtta atgtctggct tctgataaag cgggccatgt    4260
taagggcggt ttttcctgt ttggtcactg atgcctccgt gtaagggga tttctgttca    4320
tgggggtaat gataccgatg aaacgagaga ggatgctcac gatacgggtt actgatgatg    4380
aacatgcccg gttactggaa cgttgtgagg gtaaacaact gcggtatgg atgcggcggg    4440
accagagaaa aatcactcag ggtcaatgcc agcgcttcgt taatacagat gtaggtgttc    4500
cacagggtag ccagcagcat cctgcgatgc agatccggaa cataatggtg cagggcgctg    4560
acttccgcgt ttccagactt tacgaaacac ggaaaccgaa gaccattcat gttgttgctc    4620
aggtcgcaga cgttttgcag cagcagtcgc ttcacgttcg ctcgcgtatc ggtgattcat    4680
tctgctaacc agtaaggcaa ccccgccagc ctagccgggt cctcaacgac aggagcacga    4740
tcatgcgcac ccgtggggcc gccatgccgg cgataatggc ctgcttctcg ccgaaacgtt    4800
tggtggcggg accagtgacg aaggcttgag cgagggcgtg caagattccg aataccgcaa    4860
gcgacaggcc gatcatcgtc gcgctccagc gaaagcggtc ctcgccgaaa atgacccaga    4920
gcgctgccgg cacctgtcct acgagttgca tgataaagaa gacagtcata agtgcggcga    4980
cgatagtcat gccccgcgcc caccggaagg agctgactgg gttgaaggct ctcaagggca    5040
tcggtcgaga tcccggtgcc taatgagtga gctaacttac attaattgcg ttgcgctcac    5100
tgcccgcttt ccagtcggga aacctgtcgt gccagctgca ttaatgaatc ggccaacgcg    5160
cggggagagg cggtttgcgt attgggcgcc agggtggttt ttcttttcac cagtgagacg    5220
ggcaacagct gattgcccct caccgcctgg ccctgagaga gttgcagcaa gcggtccacg    5280
ctggtttgcc ccagcaggcg aaaatcctgt ttgatggtgg ttaacggcgg gatataacat    5340
gagctgtctt cggtatcgtc gtatcccact accgagatgt ccgcaccaac gcgcagcccg    5400
gactcggtaa tggcgcgcat tgcgcccagc gccatctgat cgttggcaac cagcatcgca    5460
gtgggaacga tgccctcatt cagcatttgc atggtttgtt gaaaaccgga catggcactc    5520
cagtcgcctt cccgttccgc tatcggctga atttgattgc gagtgagata tttatgccag    5580
ccagccagac gcagacgcgc cgagacagaa cttaatgggc ccgctaacag cgcgatttgc    5640
tggtgaccca atgcgaccag atgctccacg cccagtcgcg taccgtcttc atgggagaaa    5700
ataatactgt tgatgggtgt ctggtcagag acatcaagaa ataacgccgg aacattagtg    5760
caggcagctt ccacagcaat ggcatcctgg tcatccagcg gatagttaat gatcagccca    5820
ctgacgcgtt gcgcgagaag attgtgcacc gccgctttac aggcttcgac gccgcttcgt    5880
tctaccatcg acaccaccac gctggcaccc agttgatcgg cgcgagattt aatcgccgcg    5940
acaatttgcg acggcgcgtg cagggccaga ctggaggtgg caacgccaat cagcaacgac    6000
tgtttgcccg ccagttgttg tgccacgcgg ttgggaatgt aattcagctc cgccatcgcc    6060
gcttccactt tttcccgcgt tttcgcagaa acgtggctgg cctggttcac cacgcgggaa    6120
acggtctgat aagagacacc ggcatactct gcgacatcgt ataacgttac tggtttcaca    6180
ttcaccaccc tgaattgact ctcttccggg cgctatcatg ccataccgcg aaaggttttg    6240
cgccattcga tggtgtccgg gatctcgacg ctctccctta tgcgactcct gcattaggaa    6300
gcagcccagt agtaggttga ggccgttgag caccgccgcc gcaaggaatg gtgcatgcaa    6360
ggagatggcg cccaacagtc ccccggccac ggggcctgcc accataccca gccgaaaca    6420
agcgctcatg agcccgaagt ggcgagcccg atcttcccca tcggtgatgt cggcgatata    6480
```

-continued

```
ggcgccagca accgcacctg tggcgccggt gatgccggcc acgatgcgtc cggcgtagag      6540
gatcgagatc gatctcgatc ccgcgaaatt aatacgactc actataggg aattgtgagc       6600 ggataacaat tcccctctag aaataatttt gtttaacttt aagaaggaga tatacat         6657
```

<210> SEQ ID NO 45
<211> LENGTH: 6596
<212> TYPE: DNA
<213> ORGANISM: Artificial Sequence
<220> FEATURE:
<223> OTHER INFORMATION: Synthetic Construct (plasmid vector with insert of PG1798 of P.gingivalis W50)

<400> SEQUENCE: 45

```
atgcaccatc atcatcatca ttcttctggt ctggtgccac gcggttctgg tatgaaagaa        60
accgctgctg ctaaattcga acgccagcac atggacagcc agatctggg taccgatgac        120 gacgacaaga tgcaaaccaa ggacaattct tcttacaaac cttttcgaa agaagatatt        180 gccggaggag tttactctct cccgactcaa atcgtgcgc agaaggacaa tgccgagtgg        240
cttcttacag cgaccgtctc cacaaaccag tctgcagata ctcactttat cttcgatgag        300
aacaaccgct atatcgctcg tgacataaaa gccaatgggg taagaaaatc cacggactcc        360
atttactacg atgccaacgg gcgaatatcg catgtggatc tttatatctc gttcagtggc        420
ggagagcctg cactcgacac ccgattcaag tacacctatg atgacgaggg aaagatgacc        480
gtgagggaag tattcatgct ggtaatggat ccgaatacac ctatctcacg cttggaatat        540
cattatgatg cacagggcag actgacccac tggatttctt ttgctttcgg ggcagaatcc        600
caaaagaata cgtatcacta taatgaaaaa ggtctgttgg tcagcgaagt gctgagcaat        660
gcaatgggga caacctattc agacaccggc aaaacggaat acagctatga cgatgcagat        720
aatatggtga aggccgagta cttcgtcgtc cagcaaggaa aggcatggca agtactcaaa        780
agagaggaat acacctatga ggacaatatc tgcatacaat atttggctat taacggtacc        840
gacacaaagg tgtacaagcg agacatcgag agcgataagt ccatctccgc aaatgtcatt        900
gacattccgt caatgccgga acagacctgg cctaatatgt acggattcaa cgcaaagcga        960
ctgaaagaga cttattcctc ctacgaagga gatgtggcta ctcctatatt cgactatatc       1020
tatacgtaca aggctcttac ctcaatggca acaccttcga cagaagctca ggtagcagtc       1080
tatctcaatc cgtcaacgga ccggttagtg attctggcca acggcatcac acatctgagc       1140
atgtacgact gcagggtaa gcttatccgt gattgtgcct tgagcggcga taaggtggaa       1200
atgggtgtcg gatctttgac caaagggaca tacctgctta agtgaatac ggatcaggga        1260 gcctttgtga gaaaagtcgt gttcgatgac cgggcttctc ctcaaccatg gcgatatcgg       1320
atccgaattc gagctccgtc gacaagcttg cggccgcact cgagcaccac caccaccacc       1380
actgagatcc ggctgctaac aaagcccgaa aggaagctga gttggctgct gccaccgctg       1440
agcaataact agcataaccc cttggggcct ctaaacgggt cttgagggt tttttgctga        1500 aaggaggaac tatatccgga ttggcgaatg gacgcgcccc tgtagcggcg cattaagcgc       1560
ggcgggtgtg gtggttacgc gcagcgtgac cgctacactt gccagcgccc tagcgcccgc       1620
tcctttcgct ttcttccctt cctttctcgc cacgttcgcc ggctttcccc gtcaagctct       1680
aaatcggggg ctcccttag ggttccgatt tagtgcttta cggcacctcg accccaaaaa        1740
acttgattag ggtgatggtt cacgtagtgg gccatcgccc tgatagacgg ttttcgccc       1800 tttgacgttg gagtccacgt tctttaatag tggactcttg ttccaaactg gaacaacact       1860
```

| | |
|---|---|
| caaccctatc tcggtctatt cttttgattt ataagggatt ttgccgattt cggcctattg | 1920 |
| gttaaaaaat gagctgattt aacaaaaatt taacgcgaat tttaacaaaa tattaacgtt | 1980 |
| tacaatttca ggtggcactt ttcggggaaa tgtgcgcgga acccctattt gtttattttt | 2040 |
| ctaaatacat tcaaatatgt atccgctcat gaattaattc ttagaaaaac tcatcgagca | 2100 |
| tcaaatgaaa ctgcaattta ttcatatcag gattatcaat accatatttt tgaaaaagcc | 2160 |
| gtttctgtaa tgaaggagaa aactcaccga ggcagttcca taggatggca agatcctggt | 2220 |
| atcggtctgc gattccgact cgtccaacat caatacaacc tattaatttc ccctcgtcaa | 2280 |
| aaataaggtt atcaagtgag aaatcaccat gagtgacgac tgaatccggt gagaatggca | 2340 |
| aaagtttatg catttctttc cagacttgtt caacaggcca gccattacgc tcgtcatcaa | 2400 |
| aatcactcgc atcaaccaaa ccgttattca ttcgtgattg cgcctgagcg agacgaaata | 2460 |
| cgcgatcgct gttaaaagga caattacaaa caggaatcga atgcaaccgg cgcaggaaca | 2520 |
| ctgccagcgc atcaacaata ttttcacctg aatcaggata ttcttctaat acctggaatg | 2580 |
| ctgtttttcc ggggatcgca gtggtgagta accatgcatc atcaggagta cggataaaat | 2640 |
| gcttgatggt cggaagaggc ataaattccg tcagccagtt tagtctgacc atctcatctg | 2700 |
| taacatcatt ggcaacgcta cctttgccat gtttcagaaa caactctggc gcatcgggct | 2760 |
| tcccatacaa tcgatagatt gtcgcacctg attgcccgac attatcgcga gcccatttat | 2820 |
| acccatataa atcagcatcc atgttggaat ttaatcgcgg cctagagcaa gacgtttccc | 2880 |
| gttgaatatg gctcataaca ccccttgtat tactgtttat gtaagcagac agttttattg | 2940 |
| ttcatgacca aaatccctta cgtgagtttt cgttccact gagcgtcaga ccccgtagaa | 3000 |
| aagatcaaag gatcttcttg agatcctttt tttctgcgcg taatctgctg cttgcaaaca | 3060 |
| aaaaaaccac cgctaccagc ggtggtttgt ttgccggatc aagagctacc aactcttttt | 3120 |
| ccgaaggtaa ctggcttcag cagagcgcag ataccaaata ctgtccttct agtgtagccg | 3180 |
| tagttaggcc accacttcaa gaactctgta gcaccgccta catacctcgc tctgctaatc | 3240 |
| ctgttaccag tggctgctgc cagtggcgat aagtcgtgtc ttaccgggtt ggactcaaga | 3300 |
| cgatagttac cggataaggc gcagcggtcg ggctgaacgg ggggttcgtg cacacagccc | 3360 |
| agcttggagc gaacgaccta caccgaactg agatacctac agcgtgagct atgagaaagc | 3420 |
| gccacgcttc ccgaagggag aaaggcggac aggtatccgg taagcggcag gtcggaaca | 3480 |
| ggagagcgca cgagggagct tccaggggga aacgcctggt atctttatag tcctgtcggg | 3540 |
| tttcgccacc tctgacttga gcgtcgattt ttgtgatgct cgtcagggggg cggagccta | 3600 |
| tggaaaaacg ccagcaacgc ggccttttta cggttcctgg ccttttgctg ccttttgct | 3660 |
| cacatgttct ttcctgcgtt atcccctgat tctgtggata accgtattac cgcctttgag | 3720 |
| tgagctgata ccgctcgccg cagccgaacg accgagcgca gcgagtcagt gagcgaggaa | 3780 |
| gcggaagagc gcctgatgcg gtattttctc cttacgcatc tgtgcggtat ttcacaccgc | 3840 |
| atatatggtg cactctcagt acaatctgct ctgatgccgc atagttaagc cagtatacac | 3900 |
| tccgctatcg ctacgtgact gggtcatggc tgcgccccga cacccgccaa cacccgctga | 3960 |
| cgcgccctga cgggcttgtc tgctcccggc atccgcttac agacaagctg tgaccgtctc | 4020 |
| cgggagctgc atgtgtcaga ggttttcacc gtcatcaccg aaacgcgcga ggcagctgcg | 4080 |
| gtaaagctca tcagcgtggt cgtgaagcga ttcacagatg tctgcctgtt catccgcgtc | 4140 |
| cagctcgttg agtttctcca gaagcgttaa tgtctggctt ctgataaagc gggccatgtt | 4200 |

```
aagggcggtt ttttcctgtt tggtcactga tgcctccgtg taagggggat ttctgttcat    4260
gggggtaatg ataccgatga aacgagagag gatgctcacg atacgggtta ctgatgatga    4320
acatgcccgg ttactggaac gttgtgaggg taaacaactg gcggtatgga tgcggcggga    4380
ccagagaaaa atcactcagg gtcaatgcca gcgcttcgtt aatacagatg taggtgttcc    4440
acagggtagc cagcagcatc ctgcgatgca gatccggaac ataatggtgc agggcgctga    4500
cttccgcgtt tccagacttt acgaaacacg gaaaccgaag accattcatg ttgttgctca    4560
ggtcgcagac gttttgcagc agcagtcgct tcacgttcgc tcgcgtatcg gtgattcatt    4620
ctgctaacca gtaaggcaac cccgccagcc tagccgggtc ctcaacgaca ggagcacgat    4680
catgcgcacc cgtggggccg ccatgccggc gataatggcc tgcttctcgc cgaaacgttt    4740
ggtggcggga ccagtgacga aggcttgagc gagggcgtgc aagattccga ataccgcaag    4800
cgacaggccg atcatcgtcg cgctccagcg aaagcggtcc tcgccgaaaa tgacccagag    4860
cgctgccggc acctgtccta cgagttgcat gataaagaag acagtcataa gtgcggcgac    4920
gatagtcatg ccccgcgccc accggaagga gctgactggg ttgaaggctc tcaagggcat    4980
cggtcgagat cccggtgcct aatgagtgag ctaacttaca ttaattgcgt tgcgctcact    5040
gcccgctttc cagtcgggaa acctgtcgtg ccagctgcat taatgaatcg gccaacgcgc    5100
ggggagaggc ggtttgcgta ttgggcgcca gggtggtttt tcttttcacc agtgagacgg    5160
gcaacagctg attgcccttc accgcctggc cctgagagag ttgcagcaag cggtccacgc    5220
tggtttgccc cagcaggcga aaatcctgtt tgatggtggt taacggcggg atataacatg    5280
agctgtcttc ggtatcgtcg tatcccacta ccgagatgtc cgcaccaacg cgcagcccgg    5340
actcggtaat ggcgcgcatt gcgcccagcg ccatctgatc gttggcaacc agcatcgcag    5400
tgggaacgat gccctcattc agcatttgca tggtttgttg aaaaccggac atggcactcc    5460
agtcgccttc ccgttccgct atcggctgaa tttgattgcg agtgagatat ttatgccagc    5520
cagccagacg cagacgcgcc gagacagaac ttaatgggcc cgctaacagc gcgatttgct    5580
ggtgacccaa tgcgaccaga tgctccacgc ccagtcgcgt accgtcttca tgggagaaaa    5640
taatactgtt gatgggtgtc tggtcagaga catcaagaaa taacgccgga acattagtgc    5700
aggcagcttc cacagcaatg gcatcctggt catccagcgg atagttaatg atcagcccac    5760
tgacgcgttg cgcgagaaga ttgtgcaccg ccgctttaca ggcttcgacg ccgcttcgtt    5820
ctaccatcga caccaccacg ctggcaccca gttgatcggc gcgagattta atcgccgcga    5880
caatttgcga cggcgcgtgc agggccagac tggaggtggc aacgccaatc agcaacgact    5940
gtttgcccgc cagttgttgt gccacgcggt tgggaatgta attcagctcc gccatcgccg    6000
cttccacttt ttcccgcgtt ttcgcagaaa cgtggctggc ctggttcacc acgcgggaaa    6060
cggtctgata agagacaccg gcatactctg cgacatcgta taacgttact ggtttcacat    6120
tcaccaccct gaattgactc tcttccgggc gctatcatgc cataccgcga aaggttttgc    6180
gccattcgat ggtgtccggg atctcgacgc tctcccttat gcgactcctg cattaggaag    6240
cagcccagta gtaggttgag gccgttgagc accgccgccg caaggaatgg tgcatgcaag    6300 gagatgcgc caacagtcc cccggccacg gggcctgcca ccatacccac gccgaaacaa    6360
gcgctcatga gcccgaagtg gcgagcccga tcttccccat cggtgatgtc ggcgatatag    6420
gcgccagcaa ccgcacctgt ggcgccggtg atgccggcca cgatgcgtcc ggcgtagagg    6480
atcgagatcg atctcgatcc cgcgaaatta atacgactca ctataggga attgtgagcg    6540 gataacaatt cccctctaga aataattttg tttaacttta agaaggagat atacat         6596
```

<210> SEQ ID NO 46
<211> LENGTH: 6597
<212> TYPE: DNA
<213> ORGANISM: Artificial Sequence
<220> FEATURE:
<223> OTHER INFORMATION: Synthetic Construct (plasmid vector with insert of PG1798 of P. gingivalis W50)

<400> SEQUENCE: 46

```
atgcaccatc atcatcatca ttcttctggt ctggtgccac gcggttctgg tatgaaagaa      60
accgctgctg ctaaattcga acgccagcac atggacagcc agatctggg taccgatgac     120
gacgacaaga tgcaaaccaa ggacaattct tcttacaaac cttttcgaa agaagatatt     180
gccggaggag tttactctct cccgactcaa atcgtgcgc agaaggacaa tgccgagtgg     240
cttcttacag cgaccgtctc cacaaaccag tctgcagata ctcactttat cttcgatgag     300
aacaaccgct atatcgctcg tgacataaaa gccaatgggg taagaaaatc cacggactcc     360
atttactacg atgccaacgg gcgaatatcg catgtggatc tttatatctc gttcagtggc     420
ggagagcctg cactcgacac ccgattcaag tacacctatg atgacgaggg aaagatgacc     480
gtgagggaag tattcatgct ggtaatggat ccgaatacac ctatctcacg cttgaatat     540
cattatgatg cacagggcag actgacccac tggatttctt ttgctttcgg ggcagaatcc     600
caaaagaata cgtatcacta taatgaaaaa ggtctgttgg tcagcgaagt gctgagcaat     660
gcaatgggga caacctattc agacaccggc aaaacggaat acagctatga cgatgcagat     720
aatatggtga aggccgagta cttcgtcgtc cagcaaggaa aggcatggca agtactcaaa     780
agagaggaat acacctatga ggacaatatc tgcatacaat atttggctat taacggtacc     840
gacacaaagg tgtacaagcg agacatcgag agcgataagt ccatctccgc aaatgtcatt     900
gacattccgt caatgccgga acagacctgg cctaatatgt acggattcaa cgcaaagcga     960
ctgaaagaga cttattcctc ctacgaagga gatgtggcta ctcctatatt cgactatatc    1020
tatacgtaca aggctcttac ctcaatggca acaccttcga cagaagctca ggtagcagtc    1080
tatctcaatc cgtcaacgga ccggttagtg attctggcca acggcatcac acatctgagc    1140
atgtacgact tgcagggtaa gcttatccgt gattgtgcct tgagcggcga taaggtggaa    1200
atgggtgtcg atctttgac caaagggaca tacctgctta agtgaatac ggatcaggga    1260
gccttttgtga gaaaagtcgt gattcgatga ccgggcttct cctcaaccat ggcgatatcg    1320
gatccgaatt cgagctccgt cgacaagctt gcggccgcac tcgagcacca ccaccaccac    1380
cactgagatc cggctgctaa caaagcccga aggaagctg agttggctgc tgccaccgct    1440
gagcaataac tagcataacc ccttggggcc tctaaacggg tcttgagggg ttttttgctg    1500
aaaggaggaa ctatatccgg attggcgaat gggacgcgcc ctgtagcggc gcattaagcg    1560
cggcgggtgt ggtggttacg cgcagcgtga ccgctacact tgccagcgcc ctagcgcccg    1620
ctcctttcgc tttcttccct tcctttctcg ccacgttcgc cggctttccc cgtcaagctc    1680
taaatcgggg gctcccttta gggttccgat ttagtgcttt acggcacctc gaccccaaaa    1740
aacttgatta gggtgatggt tcacgtagtg gccatcgcc ctgatagacg ttttttcgcc    1800
ctttgacgtt ggagtccacg ttctttaata gtggactctt gttccaaact ggaacaacac    1860
tcaaccctat ctcggtctat tcttttgatt tataagggat tttgccgatt tcggcctatt    1920
ggttaaaaaa tgagctgatt taacaaaaat ttaacgcgaa tttaacaaa atattaacgt    1980
ttacaattc aggtggcact tttcggggaa atgtgcgcgg aacccctatt tgtttatttt    2040
```

```
tctaaataca ttcaaatatg tatccgctca tgaattaatt cttagaaaaa ctcatcgagc    2100
atcaaatgaa actgcaattt attcatatca ggattatcaa taccatattt ttgaaaaagc    2160
cgtttctgta atgaaggaga aaactcaccg aggcagttcc ataggatggc aagatcctgg    2220
tatcggtctg cgattccgac tcgtccaaca tcaatacaac ctattaattt ccctcgtca     2280 aaaataaggt tatcaagtga gaaatcacca tgagtgacga ctgaatccgg tgagaatggc    2340
aaaagtttat gcatttcttt ccagacttgt tcaacaggcc agccattacg ctcgtcatca    2400
aaatcactcg catcaaccaa accgttattc attcgtgatt gcgcctgagc gagacgaaat    2460
acgcgatcgc tgttaaaagg acaattacaa acaggaatcg aatgcaaccg cgcaggaac     2520 actgccagcg catcaacaat attttcacct gaatcaggat attcttctaa tacctggaat    2580
gctgttttcc cggggatcgc agtggtgagt aaccatgcat catcaggagt acggataaaa    2640
tgcttgatgg tcggaagagg cataaattcc gtcagccagt ttagtctgac catctcatct    2700
gtaacatcat tggcaacgct acctttgcca tgtttcagaa acaactctgg cgcatcgggc    2760
ttcccataca atcgatagat tgtcgcacct gattgcccga cattatcgcg agcccattta    2820
tacccatata aatcagcatc catgttggaa tttaatcgcg gcctagagca agacgtttcc    2880
cgttgaatat ggctcataac accccttgta ttactgttta tgtaagcaga cagttttatt    2940
gttcatgacc aaaatccctt aacgtgagtt ttcgttccac tgagcgtcag accccgtaga    3000
aaagatcaaa ggatcttctt gagatccttt ttttctgcgc gtaatctgct gcttgcaaac    3060
aaaaaaacca ccgctaccag cggtggtttg tttgccggat caagagctac caactctttt    3120
tccgaaggta actggcttca gcagagcgca gataccaaat actgtccttc tagtgtagcc    3180
gtagttaggc caccacttca agaactctgt agcaccgcct acatacctcg ctctgctaat    3240
cctgttacca gtggctgctg ccagtggcga taagtcgtgt cttaccgggt tggactcaag    3300
acgatagtta ccggataagg cgcagcggtc gggctgaacg gggggttcgt gcacacagcc    3360
cagcttggag cgaacgacct acaccgaact gagataccta cagcgtgagc tatgagaaag    3420
cgccacgctt cccgaaggga gaaaggcgga caggtatccg gtaagcggca gggtcggaac    3480
aggagagcgc acgagggagc ttccaggggg aaacgcctgg tatctttata gtcctgtcgg    3540
gtttcgccac ctctgacttg agcgtcgatt tttgtgatgc tcgtcagggg gcggagccta    3600
atggaaaaac gccagcaacg cggccttttt acggttcctg gccttttgct ggccttttgc    3660
tcacatgttc tttcctgcgt tatcccctga ttctgtggat aaccgtatta ccgcctttga    3720
gtgagctgat accgctcgcc gcagccgaac gaccgagcgc agcgagtcag tgagcgagga    3780
agcggaagag cgcctgatgc ggtattttct ccttacgcat ctgtgcggta tttcacaccg    3840
catatatggt gcactctcag tacaatctgc tctgatgccg catagttaag ccagtataca    3900
ctccgctatc gctacgtgac tgggtcatgg ctgcgccccg acacccgcca cacccgctg     3960 acgcgccctg acgggcttgt ctgctcccgg catccgctta cagacaagct gtgaccgtct    4020
ccgggagctg catgtgtcag aggttttcac cgtcatcacc gaaacgcgcg aggcagctgc    4080
ggtaaagctc atcagcgtgg tcgtgaagcg attcacagat gtctgcctgt tcatccgcgt    4140
ccagctcgtt gagtttctcc agaagcgtta atgtctggct tctgataaag cgggccatgt    4200
taagggcggt ttttttcctgt ttggtcactg atgcctccgt gtaaggggga tttctgttca    4260
tgggggtaat gataccgatg aaacgagaga ggatgctcac gatacgggtt actgatgatg    4320
aacatgcccg gttactggaa cgttgtgagg gtaaacaact ggcggtatgg atgcggcggg    4380
```

```
accagagaaa aatcactcag ggtcaatgcc agcgcttcgt taatacagat gtaggtgttc    4440
cacagggtag ccagcagcat cctgcgatgc agatccggaa cataatggtg cagggcgctg    4500
acttccgcgt ttccagactt tacgaaacac ggaaaccgaa gaccattcat gttgttgctc    4560
aggtcgcaga cgttttgcag cagcagtcgc ttcacgttcg ctcgcgtatc ggtgattcat    4620
tctgctaacc agtaaggcaa ccccgccagc ctagccgggt cctcaacgac aggagcacga    4680
tcatgcgcac ccgtggggcc gccatgccgg cgataatggc ctgcttctcg ccgaaacgtt    4740
tggtggcggg accagtgacg aaggcttgag cgagggcgtg caagattccg aataccgcaa    4800
gcgacaggcc gatcatcgtc gcgctccagc gaaagcggtc ctcgccgaaa atgacccaga    4860
gcgctgccgg cacctgtcct acgagttgca tgataaagaa gacagtcata agtgcggcga    4920
cgatagtcat gccccgcgcc caccggaagg agctgactgg gttgaaggct ctcaagggca    4980
tcggtcgaga tcccggtgcc taatgagtga gctaacttac attaattgcg ttgcgctcac    5040
tgcccgcttt ccagtcggga aacctgtcgt gccagctgca ttaatgaatc ggccaacgcg    5100
cggggagagg cggtttgcgt attgggcgcc agggtggttt tcttttcac cagtgagacg    5160
ggcaacagct gattgcccct caccgcctgg ccctgagaga gttgcagcaa gcggtccacg    5220
ctggtttgcc ccagcaggcg aaaatcctgt ttgatggtgg ttaacggcgg gatataacat    5280
gagctgtctt cggtatcgtc gtatcccact accgagatgt ccgcaccaac gcgcagcccg    5340
gactcggtaa tggcgcgcat tgcgcccagc gccatctgat cgttggcaac cagcatcgca    5400
gtgggaacga tgccctcatt cagcatttgc atggtttgtt gaaaaccgga catggcactc    5460
cagtcgcctt cccgttccgc tatcggctga atttgattgc gagtgagata tttatgccag    5520
ccagccagac gcagacgcgc cgagacagaa cttaatgggc ccgctaacag cgcgatttgc    5580
tggtgaccca atgcgaccag atgctccacg cccagtcgcg taccgtcttc atgggagaaa    5640
ataatactgt tgatgggtgt ctggtcagag acatcaagaa ataacgccgg aacattagtg    5700
caggcagctt ccacagcaat ggcatcctgg tcatccagcg gatagttaat gatcagccca    5760
ctgacgcgtt gcgcgagaag attgtgcacc gccgctttac aggcttcgac gccgcttcgt    5820
tctaccatcg acaccaccac gctggcaccc agttgatcgg cgcgagattt aatcgccgcg    5880
acaatttgcg acggcgcgtg cagggccaga ctggaggtgg caacgccaat cagcaacgac    5940
tgtttgcccg ccagttgttg tgccacgcgg ttgggaatgt aattcagctc cgccatcgcc    6000
gcttccactt tttcccgcgt tttcgcagaa acgtggctgg cctggttcac cacgcgggaa    6060
acggtctgat aagagacacc ggcatactct gcgacatcgt ataacgttac tggtttcaca    6120
ttcaccaccc tgaattgact ctcttccggg cgctatcatg ccataccgcg aaaggttttg    6180
cgccattcga tggtgtccgg gatctcgacg ctctccctta tgcgactcct gcattaggaa    6240
gcagcccagt agtaggttga ggccgttgag caccgccgcc gcaaggaatg gtgcatgcaa    6300
ggagatggcg cccaacagtc ccccggccac ggggcctgcc accatacccca gccgaaaca    6360
agcgctcatg agcccgaagt ggcgagcccg atcttcccca tcggtgatgt cggcgatata    6420
ggcgccagca accgcacctg tggcgccggt gatgccggcc acgatgcgtc cggcgtagag    6480
gatcgagatc gatctcgatc ccgcgaaatt aatacgactc actataggggg aattgtgagc    6540
ggataacaat tcccctctag aaataatttt gtttaacttt aagaaggaga tatacat     6597
```

<210> SEQ ID NO 47
<211> LENGTH: 6102
<212> TYPE: DNA
<213> ORGANISM: Artificial Sequence
<220> FEATURE:
<223> OTHER INFORMATION: Synthetic Construct (plasmid vector with insert of PG2172 of P.gingivalis W50)

<400> SEQUENCE: 47

| | | | | | |
|---|---|---|---|---|---|
| atgcaccatc | atcatcatca | ttcttctggt | ctggtgccac | gcggttctgg | tatgaaagaa | 60 |
| accgctgctg | ctaaattcga | acgccagcac | atggacagcc | agatctggg | taccgatgac | 120 |
| gacgacaaga | tgcaagttgt | gatcaaggtg | ggagatgcca | tcttggaaaa | caatgccact | 180 |
| gtggacatta | ctgctttcac | aacagaagat | ggtacggaag | agatgaaatt | tgaaggaatg | 240 |
| gttatcaacc | aatccgctac | acctatcaat | gtaatcggca | agattaccaa | gcaagaaatg | 300 |
| atcggtgatg | acactttgc | tttgtgcttt | ggtcagtgta | tggggccgaa | tgtatctgta | 360 |
| tccccccattg | tggaggctct | tgatggtgaa | ggagagtacg | tctctttgca | ttataaattt | 420 |
| cccgtgtcca | atgaagggca | tacgggagct | ttcacttta | gctgcttccc | cgagagtggt | 480 |
| gctcccggca | cagaattggc | tacagtgaac | attaacttca | agtacaaagg | cggtggaacc | 540 |
| ggtttgacta | atatcgggct | agggcgtata | gctcttatcc | agagcggtaa | tacttgcacc | 600 |
| cttcagtaca | acagcaatgg | caagcgtctt | gcccttgaag | tgtacaatct | cttaggcgta | 660 |
| aaggtattta | cctctcagct | gcccgcagga | tccggctctt | atacgctgcc | ggtgcgtctg | 720 |
| cagcgtggtg | tgcatatctt | ccgcatcaca | gaaggaggta | agcctgcgtt | tgttcagaag | 780 |
| tatctgatta | agtaaccggg | cttctcctca | accatggcga | tatcggatcc | gaattcgagc | 840 |
| tccgtcgaca | agcttgcggc | cgcactcgag | caccaccac | caccactg | agatccggct | 900 |
| gctaacaaag | cccgaaagga | agctgagttg | gctgctgcca | ccgctgagca | ataactagca | 960 |
| taaccccttg | gggcctctaa | acgggtcttg | aggggttttt | tgctgaaagg | aggaactata | 1020 |
| tccggattgg | cgaatgggac | gcgccctgta | gcggcgcatt | aagcgcggcg | ggtgtggtgg | 1080 |
| ttacgcgcag | cgtgaccgct | acacttgcca | gcgccctagc | gcccgctcct | ttcgctttct | 1140 |
| tcccttcctt | tctcgccacg | ttcgccggct | ttccccgtca | agctctaaat | cggggggctcc | 1200 |
| ctttagggtt | ccgatttagt | gctttacggc | acctcgaccc | caaaaaactt | gattagggtg | 1260 |
| atggttcacg | tagtgggcca | tcgccctgat | agacggtttt | tcgccctttg | acgttggagt | 1320 |
| ccacgttctt | taatagtgga | ctcttgttcc | aaactggaac | aacactcaac | cctatctcgg | 1380 |
| tctattcttt | tgatttataa | gggattttgc | cgatttcggc | ctattggtta | aaaaatgagc | 1440 |
| tgatttaaca | aaaatttaac | gcgaatttta | acaaaatatt | aacgtttaca | atttcaggtg | 1500 |
| gcacttttcg | gggaaatgtg | cgcggaaccc | ctatttgttt | atttttctaa | atacattcaa | 1560 |
| atatgtatcc | gctcatgaat | taattcttag | aaaaactcat | cgagcatcaa | atgaaactgc | 1620 |
| aatttattca | tatcaggatt | atcaatacca | tatttttgaa | aaagccgttt | ctgtaatgaa | 1680 |
| ggagaaaact | caccgaggca | gttccatagg | atggcaagat | cctggtatcg | gtctgcgatt | 1740 |
| ccgactcgtc | caacatcaat | acaacctatt | aatttcccct | cgtcaaaaat | aaggttatca | 1800 |
| agtgagaaat | caccatgagt | gacgactgaa | tccggtgaga | atggcaaaag | tttatgcatt | 1860 |
| tctttccaga | cttgttcaac | aggccagcca | ttacgctcgt | catcaaaatc | actcgcatca | 1920 |
| accaaaccgt | tattcattcg | tgattgcgcc | tgagcgagac | gaaatacgcg | atcgctgtta | 1980 |
| aaaggacaat | tacaaacagg | aatcgaatgc | aaccggcgca | ggaacactgc | cagcgcatca | 2040 |
| acaatatttt | cacctgaatc | aggatattct | tctaatacct | ggaatgctgt | ttcccgggg | 2100 |
| atcgcagtgg | tgagtaacca | tgcatcatca | ggagtacgga | taaaatgctt | gatggtcgga | 2160 |
| agaggcataa | attccgtcag | ccagtttagt | ctgaccatct | catctgtaac | atcattggca | 2220 |

```
acgctacctt tgccatgttt cagaaacaac tctggcgcat cgggcttccc atacaatcga    2280
tagattgtcg cacctgattg cccgacatta tcgcgagccc atttataccc atataaatca    2340
gcatccatgt tggaatttaa tcgcggccta gagcaagacg tttcccgttg aatatggctc    2400
ataacacccc ttgtattact gtttatgtaa gcagacagtt ttattgttca tgaccaaaat    2460
cccttaacgt gagttttcgt tccactgagc gtcagacccc gtagaaaaga tcaaggatc     2520 ttcttgagat cctttttttc tgcgcgtaat ctgctgcttg caaacaaaaa aaccaccgct    2580
accagcggtg gtttgtttgc cggatcaaga gctaccaact cttttccga aggtaactgg     2640 cttcagcaga gcgcagatac caaatactgt ccttctagtg tagccgtagt taggccacca    2700
cttcaagaac tctgtagcac cgcctacata cctcgctctg ctaatcctgt taccagtggc    2760
tgctgccagt ggcgataagt cgtgtcttac cgggttggac tcaagacgat agttaccgga    2820
taaggcgcag cggtcgggct gaacgggggg ttcgtgcaca cagcccagct tggagcgaac    2880
gacctacacc gaactgagat acctacagcg tgagctatga gaaagcgcca cgcttcccga    2940
agggagaaag gcggacaggt atccggtaag cggcagggtc ggaacaggag agcgcacgag    3000
ggagcttcca gggggaaacg cctggtatct ttatagtcct gtcgggtttc gccacctctg    3060
acttgagcgt cgatttttgt gatgctcgtc aggggggcgg agcctatgga aaaacgccag    3120
caacgcggcc ttttacggt tcctggcctt ttgctggcct tttgctcaca tgttctttcc     3180
tgcgttatcc cctgattctg tggataaccg tattaccgcc tttgagtgag ctgataccgc    3240
tcgccgcagc cgaacgaccg agcgcagcga gtcagtgagc gaggaagcgg aagagcgcct    3300
gatgcggtat tttctcctta cgcatctgtg cggtatttca caccgcatat atggtgcact    3360
ctcagtacaa tctgctctga tgccgcatag ttaagccagt atacactccg ctatcgctac    3420
gtgactgggt catggctgcg ccccgacacc cgccaacacc cgctgacgcg ccctgacggg    3480
cttgtctgct cccggcatcc gcttacagac aagctgtgac cgtctccggg agctgcatgt    3540
gtcagaggtt ttcaccgtca tcaccgaaac gcgcgaggca gctgcggtaa agctcatcag    3600
cgtggtcgtg aagcgattca cagatgtctg cctgttcatc cgcgtccagc tcgttgagtt    3660
tctccagaag cgttaatgtc tggcttctga taaagcgggc catgttaagg gcggttttt     3720 cctgtttggt cactgatgcc tccgtgtaag ggggatttct gttcatgggg gtaatgatac    3780
cgatgaaacg agagaggatg ctcacgatac gggttactga tgatgaacat gcccggttac    3840
tggaacgttg tgagggtaaa caactggcgg tatggatgcg gcgggaccag agaaaaatca    3900
ctcagggtca atgccagcgc ttcgttaata cagatgtagg tgttccacag ggtagccagc    3960
agcatcctgc gatgcagatc cggaacataa tggtgcaggg cgctgacttc cgcgtttcca    4020
gactttacga aacacggaaa ccgaagacca ttcatgttgt tgctcaggtc gcagacgttt    4080
tgcagcagca gtcgcttcac gttcgctcgc gtatcggtga ttcattctgc taaccagtaa    4140
ggcaaccccg ccagcctagc cgggtcctca acgacaggag cacgatcatg cgcacccgtg    4200
gggccgccat gccggcgata atggcctgct tctcgccgaa acgtttggtg gcgggaccag    4260
tgacgaaggc ttgagcgagg gcgtgcaaga ttccgaatac cgcaagcgac aggccgatca    4320
tcgtcgcgct ccagcgaaag cggtcctcgc cgaaaatgac ccagagcgct gccggcacct    4380
gtcctacgag ttgcatgata aagaagacag tcataagtgc ggcgacgata gtcatgcccc    4440
gcgcccaccg gaaggagctg actgggttga aggctctcaa gggcatcggt cgagatcccg    4500
gtgcctaatg agtgagctaa cttacattaa ttgcgttgcg ctcactgccc gctttccagt    4560
```

-continued

```
cgggaaacct gtcgtgccag ctgcattaat gaatcggcca acgcgcgggg agaggcggtt    4620
tgcgtattgg gcgccagggt ggttttcctt ttcaccagtg agacgggcaa cagctgattg    4680
cccttcaccg cctggccctg agagagttgc agcaagcggt ccacgctggt ttgccccagc    4740
aggcgaaaat cctgtttgat ggtggttaac ggcgggatat aacatgagct gtcttcggta    4800
tcgtcgtatc ccactaccga gatgtccgca ccaacgcgca gcccggactc ggtaatggcg    4860
cgcattgcgc ccagcgccat ctgatcgttg caaccagca tcgcagtggg aacgatgccc    4920
tcattcagca tttgcatggt tgttgaaaa ccggacatgg cactccagtc gccttcccgt    4980
tccgctatcg gctgaatttg attgcgagtg agatatttat gccagccagc cagacgcaga    5040
cgcgccgaga cagaacttaa tgggcccgct aacagcgcga tttgctggtg acccaatgcg    5100
accagatgct ccacgcccag tcgcgtaccg tcttcatggg agaaaataat actgttgatg    5160
ggtgtctggt cagagacatc aagaaataac gccggaacat tagtgcaggc agcttccaca    5220
gcaatggcat cctggtcatc cagcggatag ttaatgatca gcccactgac gcgttgcgcg    5280
agaagattgt gcaccgccgc tttacaggct tcgacgccgc ttcgttctac catcgacacc    5340
accacgctgg cacccagttg atcggcgcga gatttaatcg ccgcgacaat ttgcgacggc    5400
gcgtgcaggg ccagactgga ggtggcaacg ccaatcagca acgactgttt gcccgccagt    5460
tgttgtgcca cgcggttggg aatgtaattc agctccgcca tcgccgcttc cactttttcc    5520
cgcgttttcg cagaaacgtg gctggcctgg ttcaccacgc gggaaacggt ctgataagag    5580
acaccggcat actctgcgac atcgtataac gttactggtt tcacattcac caccctgaat    5640
tgactctctt ccgggcgcta tcatgccata ccgcgaaagg ttttgcgcca ttcgatggtg    5700
tccgggatct cgacgctctc ccttatgcga ctcctgcatt aggaagcagc ccagtagtag    5760
gttgaggccg ttgagcaccg ccgccgcaag gaatggtgca tgcaaggaga tggcgcccaa    5820
cagtcccccg gccacggggc ctgccaccat acccacgccg aaacaagcgc tcatgagccc    5880
gaagtggcga gcccgatctt ccccatcggt gatgtcggcg ataggcgc cagcaaccgc    5940 acctgtggcg ccggtgatgc cggccacgat gcgtccggcg tagaggatcg agatcgatct    6000
cgatcccgcg aaattaatac gactcactat aggggaattg tgagcggata acaattcccc    6060
tctagaaata attttgttta actttaagaa ggagatatac at                       6102
```

<210> SEQ ID NO 48
<211> LENGTH: 6201
<212> TYPE: DNA
<213> ORGANISM: Artificial Sequence
<220> FEATURE:
<223> OTHER INFORMATION: Synthetic Construct (plasmid vector with insert
     of PG1795 of P.gingivalis W50)

<400> SEQUENCE: 48

```
atgcaccatc atcatcatca ttcttctggt ctggtgccac gcggttctgg tatgaaagaa      60
accgctgctg ctaaattcga acgccagcac atggacagcc agatctgggt accgatgac    120 gacgacaaga tgcagtcttt gagcacaatc aaagtacaga acaattcagt acagcaacct    180
cgtgaggaag ccactattca ggtttgtgga gaattggcag agcaagttga ctgcattggg    240
acaggtaatt ctgcaatcat agccgctgca gcgaaatttg aaagcgatga tctcgaaagc    300
tatgttggct gggagatcat gagtgttgat ttcttccctg gatataaagc gtgcaagtac    360
acatctgcag tctgggctga tgatatgacc attttgggcc aatcagaaga tagtgatccc    420
gaaatgcaga ctatcaacaa tcttgctctc aagactagtg tcaagattga agccggcaag    480
```

| | | | | | |
|---|---|---|---|---|---|
| aattacatag | ttggttatat | tgctaatacc | gcaggtggac | atcctatcgg | atgtgatcag | 540 |
| ggccctgccg | ttgatggtta | tggagatttg | gtttctatat | cagaagatgg | tggtgctact | 600 |
| ttccctccgt | tcgaatctct | tcatcaagca | gttcctacct | taaattacaa | catctatgtc | 660 |
| gttgttcatt | tgaagaaggg | tgaaggtgtt | gaggctgttc | ttaccaacga | caaggctaat | 720 |
| gcttatgttc | agaatggcgt | tatctatgta | gccggagcta | atggtcgtca | ggtatctctg | 780 |
| ttcgacatga | acgtaaggt | tgtttatacc | ggcgttagcg | aaacgattgc | agctcctcag | 840 |
| aagggcatgt | atatcctccg | tgtaggtgct | aagagcatca | agctggctat | ctaaccgggc | 900 |
| ttctcctcaa | ccatggcgat | atcggatccg | aattcgagct | ccgtcgacaa | gcttgcggcc | 960 |
| gcactcgagc | accaccacca | ccaccactga | gatccggctg | ctaacaaagc | ccgaaaggaa | 1020 |
| gctgagttgg | ctgctgccac | cgctgagcaa | taactagcat | aaccccttgg | ggcctctaaa | 1080 |
| cgggtcttga | ggggttttt | gctgaaagga | ggaactatat | ccggattggc | gaatgggacg | 1140 |
| cgccctgtag | cggcgcatta | agcgcggcgg | gtgtggtggt | tacgcgcagc | gtgaccgcta | 1200 |
| cacttgccag | cgccctagcg | cccgctcctt | tcgctttctt | cccttccttt | ctcgccacgt | 1260 |
| tcgccggctt | tccccgtcaa | gctctaaatc | ggggctccc | tttagggttc | cgatttagtg | 1320 |
| ctttacggca | cctcgacccc | aaaaaacttg | attagggtga | tggttcacgt | agtgggccat | 1380 |
| cgccctgata | gacggttttt | cgccctttga | cgttggagtc | cacgttcttt | aatagtggac | 1440 |
| tcttgttcca | aactggaaca | acactcaacc | ctatctcggt | ctattctttt | gatttataag | 1500 |
| ggattttgcc | gatttcggcc | tattggttaa | aaatgagct | gatttaacaa | aaatttaacg | 1560 |
| cgaattttaa | caaatatta | acgtttacaa | tttcaggtgg | cacttttcgg | ggaaatgtgc | 1620 |
| gcggaacccc | tatttgttta | tttttctaaa | tacattcaaa | tatgtatccg | ctcatgaatt | 1680 |
| aattcttaga | aaaactcatc | gagcatcaaa | tgaaactgca | atttattcat | atcaggatta | 1740 |
| tcaataccat | atttttgaaa | aagccgtttc | tgtaatgaag | gagaaaactc | accgaggcag | 1800 |
| ttccatagga | tggcaagatc | ctggtatcgg | tctgcgattc | cgactcgtcc | aacatcaata | 1860 |
| caacctatta | atttcccctc | gtcaaaaata | aggttatcaa | gtgagaaatc | accatgagtg | 1920 |
| acgactgaat | ccggtgagaa | tggcaaaagt | ttatgcattt | cttccagac | ttgttcaaca | 1980 |
| ggccagccat | tacgctcgtc | atcaaaatca | ctcgcatcaa | ccaaaccgtt | attcattcgt | 2040 |
| gattgcgcct | gagcgagacg | aaatacgcga | tcgctgttaa | aaggacaatt | acaaacagga | 2100 |
| atcgaatgca | accggcgcag | gaacactgcc | agcgcatcaa | caatatttc | acctgaatca | 2160 |
| ggatattctt | ctaatacctg | gaatgctgtt | ttccggggga | tcgcagtggt | gagtaaccat | 2220 |
| gcatcatcag | gagtacggat | aaaatgcttg | atggtcggaa | gaggcataaa | ttccgtcagc | 2280 |
| cagtttagtc | tgaccatctc | atctgtaaca | tcattggcaa | cgctacccttt | gccatgtttc | 2340 |
| agaaacaact | ctggcgcatc | gggcttccca | tacaatcgat | agattgtcgc | acctgattgc | 2400 |
| ccgacattat | cgcgagccca | tttataccca | tataaatcag | catccatgtt | ggaatttaat | 2460 |
| cgcggcctag | agcaagacgt | ttcccgttga | atatggctca | taacaccccct | tgtattactg | 2520 |
| tttatgtaag | cagacagttt | tattgttcat | gaccaaaatc | ccttaacgtg | agttttcgtt | 2580 |
| ccactgagcg | tcagacccccg | tagaaaagat | caaaggatct | tcttgagatc | cttttttct | 2640 |
| gcgcgtaatc | tgctgcttgc | aaacaaaaaa | accaccgcta | ccagcggtgg | tttgtttgcc | 2700 |
| ggatcaagag | ctaccaactc | ttttccgaa | ggtaactggc | ttcagcagag | cgcagatacc | 2760 |
| aaatactgtc | cttctagtgt | agccgtagtt | aggccaccac | ttcaagaact | ctgtagcacc | 2820 |
| gcctacatac | ctcgctctgc | taatcctgtt | accagtggct | gctgccagtg | gcgataagtc | 2880 |

```
gtgtcttacc gggttggact caagacgata gttaccggat aaggcgcagc ggtcgggctg   2940
aacgggggt tcgtgcacac agcccagctt ggagcgaacg acctacaccg aactgagata    3000
cctacagcgt gagctatgag aaagcgccac gcttcccgaa gggagaaagg cggacaggta   3060
tccggtaagc ggcagggtcg gaacaggaga gcgcacgagg gagcttccag ggggaaacgc   3120
ctggtatctt tatagtcctg tcgggtttcg ccacctctga cttgagcgtc gattttgtg    3180
atgctcgtca ggggggcgga gcctatggaa aaacgccagc aacgcggcct ttttacggtt   3240
cctggccttt tgctggcctt ttgctcacat gttctttcct gcgttatccc ctgattctgt   3300
ggataaccgt attaccgcct ttgagtgagc tgataccgct cgccgcagcc gaacgaccga   3360
gcgcagcgag tcagtgagcg aggaagcgga agagcgcctg atgcggtatt ttctccttac   3420
gcatctgtgc ggtatttcac accgcatata tggtgcactc tcagtacaat ctgctctgat   3480
gccgcatagt taagccagta tacactccgc tatcgctacg tgactgggtc atggctgcgc   3540
cccgacaccc gccaacaccc gctgacgcgc cctgacgggc ttgtctgctc ccggcatccg   3600
cttacagaca agctgtgacc gtctccggga gctgcatgtg tcagaggttt tcaccgtcat   3660
caccgaaacg cgcgaggcag ctgcggtaaa gctcatcagc gtggtcgtga agcgattcac   3720
agatgtctgc ctgttcatcc gcgtccagct cgttgagttt ctccagaagc gttaatgtct   3780
ggcttctgat aaagcgggcc atgttaaggg cggttttttc ctgtttggtc actgatgcct   3840
ccgtgtaagg gggatttctg ttcatggggg taatgatacc gatgaaacga gagaggatgc   3900
tcacgatacg ggttactgat gatgaacatg cccggttact ggaacgttgt gagggtaaac   3960
aactggcggt atggatgcgg cgggaccaga gaaaaatcac tcagggtcaa tgccagcgct   4020
tcgttaatac agatgtaggt gttccacagg gtagccagca gcatcctgcg atgcagatcc   4080
ggaacataat ggtgcagggc gctgacttcc gcgtttccag actttacgaa acacggaaac   4140
cgaagaccat tcatgttgtt gctcaggtcg cagacgtttt gcagcagcag tcgcttcacg   4200
ttcgctcgcg tatcggtgat tcattctgct aaccagtaag gcaaccccgc cagcctagcc   4260
gggtcctcaa cgacaggagc acgatcatgc gcacccgtgg ggccgccatg ccggcgataa   4320
tggcctgctt ctcgccgaaa cgtttggtgg cgggaccagt gacgaaggct tgagcgaggg   4380
cgtgcaagat tccgaatacc gcaagcgaca ggccgatcat cgtcgcgctc cagcgaaagc   4440
ggtcctcgcc gaaaatgacc cagagcgctg ccggcacctg tcctacgagt tgcatgataa   4500
agaagacagt cataagtgcg gcgacgatag tcatgccccg cgcccaccgg aaggagctga   4560
ctgggttgaa ggctctcaag ggcatcggtc gagatcccgg tgcctaatga gtgagctaac   4620
ttacattaat tgcgttgcgc tcactgcccg ctttccagtc gggaaacctg tcgtgccagc   4680
tgcattaatg aatcggccaa cgcgcgggga gaggcggttt gcgtattggg cgccagggtg   4740
ttttttcttt tcaccagtga cgggcaac agctgattgc ccttcaccgc ctggccctga    4800
gagagttgca gcaagcggtc cacgctggtt tgccccagca ggcgaaaatc ctgtttgatg   4860
gtggttaacg gcgggatata acatgagctg tcttcggtat cgtcgtatcc cactaccgag   4920
atgtccgcac caacgcgcag cccggactcg gtaatggcgc gcattgcgcc cagcgccatc   4980
tgatcgttgg caaccagcat cgcagtggga acgatgccct cattcagcat ttgcatggtt   5040
tgttgaaaac cggacatggc actccagtcg ccttcccgtt ccgctatcgg ctgaatttga   5100
ttgcgagtga gatatttatg ccagccagcc agacgcagac gcgccgagac agaacttaat   5160
gggcccgcta acagcgcgat ttgctggtga cccaatgcga ccagatgctc cacgcccagt   5220
```

| | |
|---|---|
| cgcgtaccgt cttcatggga gaaaataata ctgttgatgg gtgtctggtc agagacatca | 5280 |
| agaaataacg ccggaacatt agtgcaggca gcttccacag caatggcatc ctggtcatcc | 5340 |
| agcggatagt taatgatcag cccactgacg cgttgcgcga aagattgtg caccgccgct | 5400 |
| ttacaggctt cgacgccgct tcgttctacc atcgacacca ccacgctggc acccagttga | 5460 |
| tcggcgcgag atttaatcgc cgcgacaatt tgcgacggcg cgtgcagggc cagactggag | 5520 |
| gtggcaacgc caatcagcaa cgactgtttg cccgccagtt gttgtgccac gcggttggga | 5580 |
| atgtaattca gctccgccat cgccgcttcc acttttccc gcgttttcgc agaaacgtgg | 5640 |
| ctggcctggt tcaccacgcg ggaaacggtc tgataagaga caccggcata ctctgcgaca | 5700 |
| tcgtataacg ttactggttt cacattcacc accctgaatt gactctcttc cgggcgctat | 5760 |
| catgccatac cgcgaaaggt tttgcgccat tcgatggtgt ccgggatctc gacgctctcc | 5820 |
| cttatgcgac tcctgcatta ggaagcagcc cagtagtagg ttgaggccgt tgagcaccgc | 5880 |
| cgccgcaagg aatggtgcat gcaaggagat ggcgcccaac agtccccgg ccacggggcc | 5940 |
| tgccaccata cccacgccga aacaagcgct catgagcccg aagtggcgag cccgatcttc | 6000 |
| cccatcggtg atgtcggcga tataggcgcc agcaaccgca cctgtggcgc cggtgatgcc | 6060 |
| ggccacgatg cgtccggcgt agaggatcga gatcgatctc gatcccgcga aattaatacg | 6120 |
| actcactata ggggaattgt gagcggataa caattcccct ctagaaataa ttttgtttaa | 6180 |
| ctttaagaag gagatataca t | 6201 |

<210> SEQ ID NO 49
<211> LENGTH: 6063
<212> TYPE: DNA
<213> ORGANISM: Artificial Sequence
<220> FEATURE:
<223> OTHER INFORMATION: Synthetic Construct (plasmid vector with insert of PG0613 of P.gingivalis W50)

<400> SEQUENCE: 49

| | |
|---|---|
| atgcaccatc atcatcatca ttcttctggt ctggtgccac gcggttctgg tatgaaagaa | 60 |
| accgctgctg ctaaattcga acgccagcac atggacagcc cagatctggg taccgatgac | 120 |
| gacgacaaga tgcaaacaac gacgaacagt agccggagtt attttacagg acgaatcgag | 180 |
| aaggtgagtt tgaacttagg ggtcccccc gtaagcacag aggttgggg aatgacccat | 240 |
| gatgcgaacg gtctcccttt cgaaatacct atctctttca gtcgtttcaa cagccaggga | 300 |
| gatatagcta ccacttatta catagcgaat agcgaggcaa ctttgaatga atggtgcgac | 360 |
| tatgcacacc cgggcggcat cgtgagggta gaaggtcgtt tttggaaaat gacttacaac | 420 |
| ataccaacct acaatgcagt ctgcacccgg attacattcg aaaatcaaga aatagaagga | 480 |
| acgatcgtct tgatacccaa gcccaaagtc tcgctgcctc atgtgtcgga atcggtgcct | 540 |
| tgcatccgaa ccgaagccgg gagggaattt atcctttgcg aagaagacga cacctttgtg | 600 |
| tctcacgatg gtaacgaagt aacgataggc ggtaaaccc tcttgctcaa taccaacgta | 660 |
| aagattgtgg gggacgtatc tcaaaagtat gccgtggggg taggagaaat tcgattcctg | 720 |
| cagatttgtg cccaaacagt atcacaacaa aaatgaccgg gcttctcctc aaccatggcg | 780 |
| atatcggatc cgaattcgag ctccgtcgac aagcttgcgg ccgcactcga gcaccaccac | 840 |
| caccaccact gagatccggc tgctaacaaa gcccgaaagg aagctgagtt ggctgctgcc | 900 |
| accgctgagc aataactagc ataaccccctt ggggcctcta aacgggtctt gaggggtttt | 960 |
| ttgctgaaag gaggaactat atccggattg gcgaatggga cgcgccctgt agcggcgcat | 1020 |

```
taagcgcggc gggtgtggtg gttacgcgca gcgtgaccgc tacacttgcc agcgccctag     1080
cgcccgctcc tttcgctttc ttcccttcct ttctcgccac gttcgccggc tttccccgtc     1140
aagctctaaa tcggggcctc cctttagggt tccgatttag tgctttacgg cacctcgacc     1200
ccaaaaaact tgattagggt gatggttcac gtagtgggcc atcgccctga tagacggttt     1260
ttcgcccttt gacgttggag tccacgttct ttaatagtgg actcttgttc caaactggaa     1320
caacactcaa ccctatctcg gtctattctt tgatttata agggattttg ccgatttcgg      1380
cctattggtt aaaaaatgag ctgatttaac aaaaatttaa cgcgaatttt aacaaaatat     1440
taacgtttac aatttcaggt ggcacttttc ggggaaatgt gcgcggaacc cctatttgtt     1500
tattttccta aatacattca aatatgtatc cgctcatgaa ttaattctta gaaaaactca     1560
tcgagcatca aatgaaactg caatttattc atatcaggat tatcaatacc atattttga      1620 aaaagccgtt tctgtaatga aggagaaaac tcaccgaggc agttccatag gatggcaaga    1680
tcctggtatc ggtctgcgat tccgactcgt ccaacatcaa tacaacctat taatttcccc    1740
tcgtcaaaaa taaggttatc aagtgagaaa tcaccatgag tgacgactga atccggtgag    1800
aatggcaaaa gtttatgcat ttcttttccag acttgttcaa caggccagcc attacgctcg    1860
tcatcaaaat cactcgcatc aaccaaaccg ttattcattc gtgattgcgc ctgagcgaga    1920
cgaaatacgc gatcgctgtt aaaaggacaa ttacaaacag gaatcgaatg caaccggcgc    1980
aggaacactg ccagcgcatc aacaatattt tcacctgaat caggatattc ttctaatacc    2040
tggaatgctg ttttcccggg gatcgcagtg gtgagtaacc atgcatcatc aggagtacgg    2100
ataaaatgct tgatggtcgg aagaggcata aattccgtca gccagtttag tctgaccatc    2160
tcatctgtaa catcattggc aacgctacct ttgccatgtt tcagaaacaa ctctggcgca    2220
tcgggcttcc catacaatcg atagattgtc gcacctgatt gcccgacatt atcgcgagcc    2280
catttatacc catataaatc agcatccatg ttggaattta atcgcggcct agagcaagac    2340
gtttcccgtt gaatatggct cataacaccc cttgtattac tgtttatgta agcagacagt    2400
tttattgttc atgaccaaaa tcccttaacg tgagttttcg ttccactgag cgtcagaccc    2460
cgtagaaaag atcaaaggat cttcttgaga tcctttttt ctgcgcgtaa tctgctgctt     2520
gcaaacaaaa aaaccaccgc taccagcggt ggtttgtttg ccggatcaag agctaccaac    2580 tcttttccg aaggtaactg gcttcagcag agcgcagata ccaaatactg tccttctagt      2640
gtagccgtag ttaggccacc acttcaagaa ctctgtagca ccgcctacat acctcgctct    2700
gctaatcctg ttaccagtgg ctgctgccag tggcgataag tcgtgtctta ccgggttgga    2760
ctcaagacga tagttaccgg ataaggcgca gcggtcgggc tgaacggggg gttcgtgcac    2820
acagcccagc ttggagcgaa cgacctacac cgaactgaga tacctacagc gtgagctatg    2880
agaaagcgcc acgcttcccg aagggagaaa ggcggacagg tatccggtaa gcggcagggt    2940
cggaacagga gagcgcacga gggagcttcc agggggaaac gcctggtatc tttatagtcc    3000
tgtcgggttt cgccacctct gacttgagcg tcgatttttg tgatgctcgt caggggggcg    3060
gagcctatgg aaaaacgcca gcaacgcggc ctttttacgg ttcctggcct tttgctggcc    3120
ttttgctcac atgttctttc ctgcgttatc ccctgattct gtggataacc gtattaccgc    3180
ctttgagtga gctgataccg ctcgccgcag ccgaacgacc gagcgcagcg agtcagtgag    3240
cgaggaagcg gaagagcgcc tgatgcggta ttttctcctt acgcatctgt gcggtatttc    3300
acaccgcata tatggtgcac tctcagtaca atctgctctg atgccgcata gttaagccag    3360
tatacactcc gctatcgcta cgtgactggg tcatggctgc gccccgacac ccgccaacac    3420
```

```
ccgctgacgc gccctgacgg gcttgtctgc tcccggcatc cgcttacaga caagctgtga    3480
ccgtctccgg gagctgcatg tgtcagaggt tttcaccgtc atcaccgaaa cgcgcgaggc    3540
agctgcggta aagctcatca gcgtggtcgt gaagcgattc acagatgtct gcctgttcat    3600
ccgcgtccag ctcgttgagt ttctccagaa gcgttaatgt ctggcttctg ataaagcggg    3660
ccatgttaag ggcggttttt tcctgtttgg tcactgatgc ctccgtgtaa gggggatttc    3720
tgttcatggg ggtaatgata ccgatgaaac gagagaggat gctcacgata cgggttactg    3780
atgatgaaca tgcccggtta ctggaacgtt gtgagggtaa acaactggcg gtatggatgc    3840
ggcgggacca gagaaaaatc actcagggtc aatgccagcg cttcgttaat acagatgtag    3900
gtgttccaca gggtagccag cagcatcctg cgatgcagat ccggaacata atggtgcagg    3960
gcgctgactt ccgcgtttcc agactttacg aaacacggaa accgaagacc attcatgttg    4020
ttgctcaggt cgcagacgtt ttgcagcagc agtcgcttca cgttcgctcg cgtatcggtg    4080
attcattctg ctaaccagta aggcaacccc gccagcctag ccgggtcctc aacgacagga    4140
gcacgatcat gcgcacccgt ggggccgcca tgccggcgat aatggcctgc ttctcgccga    4200
aacgtttggt ggcgggacca gtgacgaagg cttgagcgag ggcgtgcaag attccgaata    4260
ccgcaagcga caggccgatc atcgtcgcgc tccagcgaaa gcggtcctcg ccgaaaatga    4320
cccagagcgc tgccggcacc tgtcctacga gttgcatgat aaagaagaca gtcataagtg    4380
cggcgacgat agtcatgccc cgcgcccacc ggaaggagct gactgggttg aaggctctca    4440
agggcatcgg tcgagatccc ggtgcctaat gagtgagcta acttacatta attgcgttgc    4500
gctcactgcc cgctttccag tcgggaaacc tgtcgtgcca gctgcattaa tgaatcggcc    4560
aacgcgcggg gagaggcggt ttgcgtattg ggcgccaggg tggttttttct tttcaccagt    4620 gagacgggca acagctgatt gcccttcacc gcctggccct gagagagttg cagcaagcgg    4680
tccacgctgg tttgccccag caggcgaaaa tcctgtttga tggtggttaa cggcgggata    4740
taacatgagc tgtcttcggt atcgtcgtat cccactaccg agatgtccgc accaacgcgc    4800
agcccggact cggtaatggc gcgcattgcg cccagcgcca tctgatcgtt ggcaaccagc    4860
atcgcagtgg gaacgatgcc ctcattcagc atttgcatgg tttgttgaaa accggacatg    4920
gcactccagt cgccttcccg ttccgctatc ggctgaattt gattgcgagt gagatattta    4980
tgccagccag ccagacgcag acgcgccgag acagaactta atgggcccgc taacagcgcg    5040
atttgctggt gacccaatgc gaccagatgc tccacgccca gtcgcgtacc gtcttcatgg    5100
gagaaaataa tactgttgat gggtgtctgg tcagagacat caagaaataa cgccggaaca    5160
ttagtgcagg cagcttccac agcaatggca tcctggtcat ccagcggata gttaatgatc    5220
agcccactga cgcgttgcgc gagaagattg tgcaccgccg ctttacaggc ttcgacgccg    5280
cttcgttcta ccatcgacac caccacgctg cacccagtt gatcggcgcg agatttaatc    5340
gccgcgacaa tttgcgacgg cgcgtgcagg gccagactgg aggtggcaac gccaatcagc    5400
aacgactgtt tgcccgccag ttgttgtgcc acgcggttgg gaatgtaatt cagctccgcc    5460
atcgccgctt ccactttttc ccgcgttttc gcagaaacgt ggctggcctg gttcaccacg    5520
cgggaaacgg tctgataaga gacaccggca tactctgcga catcgtataa cgttactggt    5580
ttcacattca cccacctgaa ttgactctct tccgggcgct atcatgccat accgcgaaag    5640
gttttgcgcc attcgatggt gtccgggatc tcgacgctct cccttatgcg actcctgcat    5700
taggaagcag cccagtagta ggttgaggcc gttgagcacc ccgccgcaa ggaatggtgc    5760
```

| | |
|---|---|
| atgcaaggag atggcgccca acagtccccc ggccacgggg cctgccacca tacccacgcc | 5820 |
| gaaacaagcg ctcatgagcc cgaagtggcg agcccgatct tccccatcgg tgatgtcggc | 5880 |
| gatataggcg ccagcaaccg cacctgtggc gccggtgatg ccggccacga tgcgtccggc | 5940 |
| gtagaggatc gagatcgatc tcgatcccgc gaaattaata cgactcacta tagggggaatt | 6000 |
| gtgagcggat aacaattccc ctctagaaat aattttgttt aactttaaga aggagatata | 6060 |
| cat | 6063 |

<210> SEQ ID NO 50
<211> LENGTH: 6888
<212> TYPE: DNA
<213> ORGANISM: Artificial Sequence
<220> FEATURE:
<223> OTHER INFORMATION: Synthetic Construct (plasmid vector with insert of PG0186 of P.gingivalis W50)

<400> SEQUENCE: 50

| | |
|---|---|
| atgcaccatc atcatcatca ttcttctggt ctggtgccac gcggttctgg tatgaaagaa | 60 |
| accgctgctg ctaaattcga acgccagcac atggacagcc cagatctggg taccgatgac | 120 |
| gacgacaaga tgtgcgagct tgaccgcgac cccgaaggaa aagatttcca acagccatat | 180 |
| acttctttcg tgcagacgaa acaaaacaga gatggtcttt acgcactttt gcgtaatact | 240 |
| gaaaatccac gaatgcattt ttatcaggaa cttcaatccg atatgtattg cactaccatt | 300 |
| actgatggta actccttagc tccgttcgtg aattgggatt taggcatact taacgaccat | 360 |
| ggacgtgctg atgaggacga agtctccggt atagctggct actatttcgt atacaatcga | 420 |
| ctaaatcagc aagcgaatgc ttttgttaac aatacggaag ctgcgttgca gaatcaagtg | 480 |
| tataaaaatt ccaccgagat cgccaatgct aagagctttt tggcggaagg aaaagttttta | 540 |
| caagcattgg ctatttggcg actgatggat cgttttagct tccatgaaag cgtgacagaa | 600 |
| gttaattccg gtgcgaaaga tcttggcgtt attctgttga agaatataaa tcctggttat | 660 |
| atcggtcccc gtgcaacgaa ggcacaatgt tatgattaca ttttgtcacg tttgtctgag | 720 |
| gctattgaag ttttgcccga aaacagggaa agcgttcttt atgtgagccg tgattacgcc | 780 |
| tatgccctcc gagcaagaat ttacctcgcg ttgggtgaat atggaaaagc tgcagcagat | 840 |
| gctaagatgg ttgttgataa gtatcctttg attggtgcag cagatgcttc tgagtttgag | 900 |
| aatatttatc gatcagatgc taataatccc gaaattattt tcgtggtttt gcttctgcg | 960 |
| actcttggct cgtttactgc tacgacacta atggtgctg cgccagcagg taaggatata | 1020 |
| aaatataatc gagcgcagt ccctttccaa tgggtagtgg atctttatga aaacgaagat | 1080 |
| ttccgcaaat ccgtatatat cgcgaaagtt gtgaaaaagg ataagggggta tttagtaaat | 1140 |
| aaattccttg aggacaaggc ttatcgtgat gttcaggata agccaaacct taagtcgga | 1200 |
| gctcgttatt ttagcgttgc tgaggtctac ttaattttgg tagagtctgc tcttcagact | 1260 |
| ggagataccc caacagccga aaaatatctc aaggctttga gtaaagctcg tggagcagaa | 1320 |
| gtttcagtcg ttaatatgga agcactgcaa gcagagcgta cgcgtgagct tataggtgag | 1380 |
| ggtagtcgtt tgcgtgatat ggtccgctgg agtatcccta ataatcatga tgctttttgag | 1440 |
| actcagcctg gttagaaagg ttttgcaaat actactcctt tgaaagctca agctcctgta | 1500 |
| ggcttttatg catatacttg ggagttccca cagcgagatc gacaaactaa tccgcagtta | 1560 |
| ataaagaact ggccgatata accgggcttc tcctcaacca tggcgatatc ggatccgaat | 1620 |
| tcgagctccg tcgacaagct tgcggccgca ctcgagcacc accaccacca ccactgagat | 1680 |

```
ccggctgcta acaaagcccg aaaggaagct gagttggctg ctgccaccgc tgagcaataa    1740
ctagcataac cccttggggc tctaaacgg gtcttgaggg gttttttgct gaaaggagga     1800
actatatccg gattggcgaa tgggacgcgc cctgtagcgg cgcattaagc gcggcgggtg    1860
tggtggttac gcgcagcgtg accgctacac ttgccagcgc cctagcgccc gctccttccg    1920
ctttcttccc ttcctttctc gccacgttcg ccggctttcc ccgtcaagct ctaaatcggg    1980
ggctcccttt agggttccga tttagtgctt tacggcacct cgaccccaaa aaacttgatt    2040
agggtgatgg ttcacgtagt gggccatcgc cctgatagac ggttttttcgc cctttgacgt   2100
tggagtccac gttctttaat agtggactct tgttccaaac tggaacaaca ctcaacccta   2160
tctcggtcta ttcttttgat ttataaggga ttttgccgat ttcggcctat tggttaaaaa    2220
atgagctgat ttaacaaaaa tttaacgcga attttaacaa atattaacg tttacaattt     2280
caggtggcac ttttcgggga aatgtgcgcg gaacccctat ttgtttattt ttctaaatac    2340
attcaaatat gtatccgctc atgaattaat tcttagaaaa actcatcgag catcaaatga    2400
aactgcaatt tattcatatc aggattatca ataccatatt tttgaaaaag ccgtttctgt     2460
aatgaaggag aaaactcacc gaggcagttc cataggatgg caagatcctg gtatcggtct     2520
gcgattccga ctcgtccaac atcaatacaa cctattaatt tcccctcgtc aaaaataagg    2580
ttatcaagtg agaaatcacc atgagtgacg actgaatccg gtgagaatgg caaaagttta    2640
tgcatttctt tccagacttg ttcaacaggc cagccattac gctcgtcatc aaaatcactc    2700
gcatcaacca aaccgttatt cattcgtgat tgcgcctgag cgagacgaaa tacgcgatcg    2760
ctgttaaaag acaattaca aacaggaatc gaatgcaacc ggcgcaggaa cactgccagc     2820
gcatcaacaa tattttcacc tgaatcagga tattcttcta atacctggaa tgctgttttc    2880
ccggggatcg cagtggtgag taaccatgca tcatcaggag tacggataaa atgcttgatg    2940
gtcggaagag gcataaattc cgtcagccag tttagtctga ccatctcatc tgtaacatca    3000
ttggcaacgc taccctttgcc atgtttcaga acaactctg gcgcatcggg cttcccatac    3060
aatcgataga ttgtcgcacc tgattgcccg acattatcgc gagcccattt atacccatat    3120
aaatcagcat ccatgttgga atttaatcgc ggcctagagc aagacgtttc ccgttgaata    3180
tggctcataa caccccttgt attactgttt atgtaagcag acagttttat tgttcatgac    3240
caaaatccct taacgtgagt tttcgttcca ctgagcgtca gaccccgtag aaaagatcaa    3300
aggatcttct tgagatcctt ttttctgcg cgtaatctgc tgcttgcaaa caaaaaaacc    3360
accgctacca gcggtggttt gtttgccgga tcaagagcta ccaactcttt ttccgaaggt    3420
aactggcttc agcagagcgc agataccaaa tactgtcctt ctagtgtagc cgtagttagg    3480
ccaccacttc aagaactctg tagcaccgcc tacatacctc gctctgctaa tcctgttacc    3540
agtggctgct gccagtggcg ataagtcgtg tcttaccggg ttggactcaa gacgatagtt    3600
accggataag gcgcagcggt cgggctgaac ggggggttcg tgcacacagc ccagcttgga    3660
gcgaacgacc tacaccgaac tgagatacct acagcgtgag ctatgagaaa gcgccacgct    3720
tcccgaaggg agaaaggcgg acaggtatcc ggtaagcggc agggtcggaa caggagagcg    3780
cacgagggag cttccagggg gaaacgcctg gtatctttat agtcctgtcg gtttcgcca    3840
cctctgactt gagcgtcgat ttttgtgatg ctcgtcaggg gggcggagcc tatggaaaaa    3900
cgccagcaac gcggcctttt tacggttcct ggccttttgc tggccttttg ctcacatgtt    3960
ctttcctgcg ttatccctg attctgtgga taaccgtatt accgcctttg agtgagctga    4020
taccgctcgc cgcagccgaa cgaccgagcg cagcgagtca gtgagcgagg aagcggaaga    4080
```

```
gcgcctgatg cggtattttc tccttacgca tctgtgcggt atttcacacc gcatatatgg    4140
tgcactctca gtacaatctg ctctgatgcc gcatagttaa gccagtatac actccgctat    4200
cgctacgtga ctgggtcatg gctgcgcccc gacacccgcc aacacccgct gacgcgccct    4260
gacgggcttg tctgctcccg gcatccgctt acagacaagc tgtgaccgtc tccgggagct    4320
gcatgtgtca gaggttttca ccgtcatcac cgaaacgcgc gaggcagctg cggtaaagct    4380
catcagcgtg gtcgtgaagc gattcacaga tgtctgcctg ttcatccgcg tccagctcgt    4440
tgagtttctc cagaagcgtt aatgtctggc ttctgataaa gcgggccatg ttaagggcgg    4500
ttttttcctg tttggtcact gatgcctccg tgtaagggggg atttctgttc atggggtaa    4560 tgataccgat gaaacgagag aggatgctca cgatacgggt tactgatgat gaacatgccc    4620
ggttactgga acgttgtgag ggtaaacaac tggcggtatg gatgcggcgg gaccagagaa    4680
aaatcactca gggtcaatgc cagcgcttcg ttaatacaga tgtaggtgtt ccacagggta    4740
gccagcagca tcctgcgatg cagatccgga acataatggt gcagggcgct gacttccgcg    4800
tttccagact ttacgaaaca cggaaaccga agaccattca tgttgttgct caggtcgcag    4860
acgttttgca gcagcagtcg cttcacgttc gctcgcgtat cggtgattca ttctgctaac    4920
cagtaaggca accccgccag cctagccggg tcctcaacga caggagcacg atcatgcgca    4980
cccgtggggc cgccatgccg gcgataatgg cctgcttctc gccgaaacgt ttggtggcgg    5040
gaccagtgac gaaggcttga gcgagggcgt gcaagattcc gaataccgca agcgacaggc    5100
cgatcatcgt cgcgctccag cgaaagcggt cctcgccgaa aatgacccag agcgctgccg    5160
gcacctgtcc tacgagttgc atgataaaga agacagtcat aagtgcggcg acgatagtca    5220
tgccccgcgc ccaccggaag gagctgactg ggttgaaggc tctcaagggc atcggtcgag    5280
atcccggtgc ctaatgagtg agctaactta cattaattgc gttgcgctca ctgcccgctt    5340
tccagtcggg aaacctgtcg tgccagctgc attaatgaat cggccaacgc gcggggagag    5400
gcggtttgcg tattgggcgc cagggtggtt tttcttttca ccagtgagac gggcaacagc    5460
tgattgccct tcaccgcctg gccctgagag agttgcagca agcggtccac gctggtttgc    5520
cccagcaggc gaaaatcctg tttgatggtg gttaacggcg ggatataaca tgagctgtct    5580
tcggtatcgt cgtatcccac taccgagatg tccgcaccaa cgcgcagccc ggactcggta    5640
atggcgcgca ttgcgcccag cgccatctga tcgttggcaa ccagcatcgc agtgggaacg    5700
atgccctcat tcagcatttg catggtttgt tgaaaaccgg acatggcact ccagtcgcct    5760
tcccgttccg ctatcggctg aatttgattg cgagtgagat atttatgcca gccagccaga    5820
cgcagacgcg ccgagacaga acttaatggg cccgctaaca gcgcgatttg ctggtgaccc    5880
aatgcgacca gatgctccac gcccagtcgc gtaccgtctt catgggagaa ataatactg    5940 ttgatgggtg tctggtcaga gacatcaaga ataacgccg gaacattagt gcaggcagct    6000
tccacagcaa tggcatcctg gtcatccagc ggatagttaa tgatcagccc actgacgcgt    6060
tgcgcgagaa gattgtgcac cgccgcttta caggcttcga cgccgcttcg ttctaccatc    6120
gacaccacca cgctggcacc cagttgatcg gcgcgagatt taatcgccgc gacaatttgc    6180
gacggcgcgt gcagggccag actggaggtg gcaacgccaa tcagcaacga ctgtttgccc    6240
gccagttgtt gtgccacgcg gttgggaatg taattcagct ccgccatcgc cgcttccact    6300
ttttcccgcg ttttcgcaga aacgtggctg gcctggttca ccacgcggga aacggtctga    6360
taagagacac cggcatactc tgcgacatcg tataacgtta ctggtttcac attcaccacc    6420
```

```
ctgaattgac tctcttccgg gcgctatcat gccataccgc gaaaggtttt gcgccattcg    6480
atggtgtccg ggatctcgac gctctcccct tatgcgactcc tgcattagga agcagcccag   6540
tagtaggttg aggccgttga gcaccgccgc cgcaaggaat ggtgcatgca aggagatggc    6600
gcccaacagt cccccggcca cggggcctgc caccataccc acgccgaaac aagcgctcat    6660
gagcccgaag tggcgagccc gatcttcccc atcggtgatg tcggcgatat aggcgccagc    6720
aaccgcacct gtggcgccgg tgatgccggc cacgatgcgt ccggcgtaga ggatcgagat    6780
cgatctcgat cccgcgaaat taatacgact cactataggg gaattgtgag cggataacaa    6840
ttcccctcta gaaataattt tgtttaactt taagaaggag atatacat                 6888
```

<210> SEQ ID NO 51
<211> LENGTH: 43
<212> TYPE: PRT
<213> ORGANISM: Artificial Sequence
<220> FEATURE:
<223> OTHER INFORMATION: Synthetic Construct (vector encoded Tag)

<400> SEQUENCE: 51

```
Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Asp Lys
        35                  40
```

<210> SEQ ID NO 52
<211> LENGTH: 19
<212> TYPE: PRT
<213> ORGANISM: Porphyromonas gingivalis

<400> SEQUENCE: 52

```
Met Lys Lys Ile Ile Tyr Trp Val Ala Thr Val Phe Leu Ala Ala Ser
1               5                   10                  15

Val Ser Ser
```

<210> SEQ ID NO 53
<211> LENGTH: 26
<212> TYPE: PRT
<213> ORGANISM: Porphyromonas gingivalis

<400> SEQUENCE: 53

```
Met Arg Lys Ile Ile Met Lys Lys Leu Phe Leu Ala Ser Val Ala Phe
1               5                   10                  15

Leu Cys Ala Trp Ile Trp Ser Ala Asn Ala
            20                  25
```

<210> SEQ ID NO 54
<211> LENGTH: 22
<212> TYPE: PRT
<213> ORGANISM: Porphyromonas gingivalis

<400> SEQUENCE: 54

```
Met Met Lys Lys Ala Phe Val Phe Val Leu Leu Val Cys Leu Phe Ser
1               5                   10                  15

Ser Phe Ser Ser Ser Ala
            20
```

<210> SEQ ID NO 55
<211> LENGTH: 21

```
<212> TYPE: PRT
<213> ORGANISM: Porphyromonas gingivalis

<400> SEQUENCE: 55

Met Lys Arg Leu Leu Pro Phe Leu Leu Leu Ala Gly Leu Val Ala Val
1               5                   10                  15

Gly Asn Val Ser Ala
            20

<210> SEQ ID NO 56
<211> LENGTH: 23
<212> TYPE: PRT
<213> ORGANISM: Porphyromonas gingivalis

<400> SEQUENCE: 56

Met Lys Leu Ser Ser Lys Lys Ile Leu Ala Ile Ile Ala Leu Leu Thr
1               5                   10                  15

Met Gly His Ala Val Gln Ala
            20

<210> SEQ ID NO 57
<211> LENGTH: 20
<212> TYPE: PRT
<213> ORGANISM: Porphyromonas gingivalis

<400> SEQUENCE: 57

Met Lys Lys Ala Leu Leu Ile Gly Ala Ala Leu Leu Gly Ala Val Ser
1               5                   10                  15

Phe Ala Ser Ala
            20

<210> SEQ ID NO 58
<211> LENGTH: 20
<212> TYPE: PRT
<213> ORGANISM: Porphyromonas gingivalis

<400> SEQUENCE: 58

Met Lys Lys Thr Thr Ile Ile Ser Leu Ile Val Phe Gly Ala Phe Phe
1               5                   10                  15

Ala Ala Val Gly
            20

<210> SEQ ID NO 59
<211> LENGTH: 28
<212> TYPE: PRT
<213> ORGANISM: Porphyromonas gingivalis

<400> SEQUENCE: 59

Met Asn Lys Lys Thr Lys Arg Asn Met Arg Lys Ile Phe Ile Ser Ile
1               5                   10                  15

Ala Leu Leu Ala Gly Phe Ile Ala Ala Leu Asn Ala
            20                  25

<210> SEQ ID NO 60
<211> LENGTH: 35
<212> TYPE: DNA
<213> ORGANISM: artificial sequence
<220> FEATURE:
<223> OTHER INFORMATION: synthetic construct (primer)

<400> SEQUENCE: 60
gacgacgaca agatgtgcga gcttgaccgc gaccc                              35
```

<210> SEQ ID NO 61
<211> LENGTH: 49
<212> TYPE: DNA
<213> ORGANISM: artificial sequence
<220> FEATURE:
<223> OTHER INFORMATION: synthetic construct (primer)

<400> SEQUENCE: 61
gaggagaagc ccggttatat cggccagttc tttattaact gcggattag          49

<210> SEQ ID NO 62
<211> LENGTH: 40
<212> TYPE: DNA
<213> ORGANISM: artificial sequence
<220> FEATURE:
<223> OTHER INFORMATION: primer

<400> SEQUENCE: 62
gacgacgaca agatgcagac aatggctcca aattacttcc                    40

<210> SEQ ID NO 63
<211> LENGTH: 46
<212> TYPE: DNA
<213> ORGANISM: artificial sequence
<220> FEATURE:
<223> OTHER INFORMATION: primer

<400> SEQUENCE: 63
gaggagaagc ccggttattg aacgatcact ctttctgtaa tatcac             46

<210> SEQ ID NO 64
<211> LENGTH: 37
<212> TYPE: DNA
<213> ORGANISM: artificial sequence
<220> FEATURE:
<223> OTHER INFORMATION: primer

<400> SEQUENCE: 64
gacgacgaca agatgcaaac aacgacgaac agtagcc                       37

<210> SEQ ID NO 65
<211> LENGTH: 40
<212> TYPE: DNA
<213> ORGANISM: artificial sequence
<220> FEATURE:
<223> OTHER INFORMATION: primer

<400> SEQUENCE: 65
gaggagaagc ccggtcattt ttgttgtgat actgtttggg                    40

<210> SEQ ID NO 66
<211> LENGTH: 37
<212> TYPE: DNA
<213> ORGANISM: artificial sequence
<220> FEATURE:
<223> OTHER INFORMATION: primer

<400> SEQUENCE: 66
gacgacgaca agatgcagtc accccgaatc cctcaag                       37

<210> SEQ ID NO 67
<211> LENGTH: 42
<212> TYPE: DNA
<213> ORGANISM: artificial sequence
<220> FEATURE:
<223> OTHER INFORMATION: primer

<400> SEQUENCE: 67
gaggagaagc ccggttatct gagcgatact tttgcacgta tg                        42

<210> SEQ ID NO 68
<211> LENGTH: 40
<212> TYPE: DNA
<213> ORGANISM: artificial sequence
<220> FEATURE:
<223> OTHER INFORMATION: primer

<400> SEQUENCE: 68
gacgacgaca agatgttgtg tgaaaatacc cttgcacaac                           40

<210> SEQ ID NO 69
<211> LENGTH: 46
<212> TYPE: DNA
<213> ORGANISM: artificial sequence
<220> FEATURE:
<223> OTHER INFORMATION: primer

<400> SEQUENCE: 69
gaggagaagc ccggttattg gatttggatt ttctcagtat agacag                    46

<210> SEQ ID NO 70
<211> LENGTH: 35
<212> TYPE: DNA
<213> ORGANISM: artificial sequence
<220> FEATURE:
<223> OTHER INFORMATION: primer

<400> SEQUENCE: 70
gacgacgaca agatgcagtt tgttccggct cccac                                35

<210> SEQ ID NO 71
<211> LENGTH: 47
<212> TYPE: DNA
<213> ORGANISM: artificial sequence
<220> FEATURE:
<223> OTHER INFORMATION: primer

<400> SEQUENCE: 71
gaggagaagc ccggttactg tttgatgagc ttagtggtat agttatc                   47

<210> SEQ ID NO 72
<211> LENGTH: 42
<212> TYPE: DNA
<213> ORGANISM: artificial sequence
<220> FEATURE:
<223> OTHER INFORMATION: primer

<400> SEQUENCE: 72
gacgacgaca agatgcagtc tttgagcaca atcaaagtac ag                        42

<210> SEQ ID NO 73
<211> LENGTH: 36
<212> TYPE: DNA
<213> ORGANISM: artificial sequence
<220> FEATURE:
<223> OTHER INFORMATION: primer

<400> SEQUENCE: 73
gaggagaagc ccggttagat agccagcttg atgctc                               36

<210> SEQ ID NO 74

```
<211> LENGTH: 43
<212> TYPE: DNA
<213> ORGANISM: artificial sequence
<220> FEATURE:
<223> OTHER INFORMATION: primer

<400> SEQUENCE: 74
gacgacgaca agatgcaaac caaggacaat tcttcttaca aac          43

<210> SEQ ID NO 75
<211> LENGTH: 38
<212> TYPE: DNA
<213> ORGANISM: artificial sequence
<220> FEATURE:
<223> OTHER INFORMATION: primer

<400> SEQUENCE: 75
gaggagaagc ccggtcatcg aatcacgact tttctcac               38

<210> SEQ ID NO 76
<211> LENGTH: 37
<212> TYPE: DNA
<213> ORGANISM: artificial sequence
<220> FEATURE:
<223> OTHER INFORMATION: primer

<400> SEQUENCE: 76
gacgacgaca agatgcaagt tgtgatcaag gtgggag                37

<210> SEQ ID NO 77
<211> LENGTH: 43
<212> TYPE: DNA
<213> ORGANISM: artificial sequence
<220> FEATURE:
<223> OTHER INFORMATION: primer

<400> SEQUENCE: 77
gaggagaagc ccggttactt aatcagatac ttctgaacaa acg          43

<210> SEQ ID NO 78
<211> LENGTH: 7
<212> TYPE: PRT
<213> ORGANISM: Porphyromonas gingivalis

<400> SEQUENCE: 78

Thr Glu Arg Val Ile Val Gln
1               5

<210> SEQ ID NO 79
<211> LENGTH: 7
<212> TYPE: PRT
<213> ORGANISM: Porphyromonas gingivalis

<400> SEQUENCE: 79

Thr Glu Arg Val Ile Val Gln
1               5
```